US009695212B2

(12) United States Patent
Dubensky, Jr. et al.

(10) Patent No.: US 9,695,212 B2
(45) Date of Patent: Jul. 4, 2017

(54) COMPOSITIONS COMPRISING CYCLIC PURINE DINUCLEOTIDES HAVING DEFINED STEREOCHEMISTRIES AND METHODS FOR THEIR PREPARATION AND USE

(71) Applicant: Aduro Biotech, Inc., Berkeley, CA (US)

(72) Inventors: Thomas W. Dubensky, Jr., Piedmont, CA (US); David B. Kanne, Corte Madera, CA (US); Meredith Lai Ling Leong, Oakland, CA (US); Edward Emile Lemmens, Walnut Creek, CA (US); Laura Hix Glickman, Oakland, CA (US)

(73) Assignee: Aduro Biotech, Inc., Berkeley, CA (US)

( * ) Notice: Subject to any disclaimer, the term of this patent is extended or adjusted under 35 U.S.C. 154(b) by 115 days.

(21) Appl. No.: 14/106,687

(22) Filed: Dec. 13, 2013

(65) Prior Publication Data

US 2014/0205653 A1 Jul. 24, 2014

Related U.S. Application Data

(60) Provisional application No. 61/737,006, filed on Dec. 13, 2012, provisional application No. 61/790,514, filed on Mar. 15, 2013.

(51) Int. Cl.

| A61K 31/7084 | (2006.01) |
|---|---|
| C07H 21/02 | (2006.01) |
| C07H 21/04 | (2006.01) |
| C07H 19/213 | (2006.01) |
| C07H 21/00 | (2006.01) |
| A61K 39/00 | (2006.01) |
| A61K 39/02 | (2006.01) |
| A61K 39/12 | (2006.01) |
| A61K 39/39 | (2006.01) |

(52) U.S. Cl.
CPC ......... *C07H 21/02* (2013.01); *A61K 31/7084* (2013.01); *A61K 39/0005* (2013.01); *A61K 39/02* (2013.01); *A61K 39/12* (2013.01); *A61K 39/39* (2013.01); *C07H 19/213* (2013.01); *C07H 21/00* (2013.01); *C07H 21/04* (2013.01)

(58) Field of Classification Search
None
See application file for complete search history.

(56) References Cited

U.S. PATENT DOCUMENTS

| 5,547,941 | A | * | 8/1996 | Battistini | ............... | C07H 19/20 |
| | | | | | | 514/44 R |
| 5,637,483 | A | | 6/1997 | Dranoff et al. | | |
| 5,698,432 | A | | 12/1997 | Oxford | | |
| 5,904,920 | A | | 5/1999 | Dranoff et al. | | |
| 5,985,290 | A | | 11/1999 | Jaffee et al. | | |
| 6,033,674 | A | | 3/2000 | Jaffee et al. | | |
| 6,090,611 | A | | 7/2000 | Covacci et al. | | |
| 6,277,368 | B1 | | 8/2001 | Hiserodt et al. | | |
| 6,350,445 | B1 | | 2/2002 | Jaffee et al. | | |
| 6,464,973 | B1 | | 10/2002 | Levitsky et al. | | |
| 6,558,670 | B1 | * | 5/2003 | Friede | .................... | A61K 39/39 |
| | | | | | | 424/184.1 |
| 6,780,429 | B1 | | 8/2004 | Matsuyama et al. | | |
| 7,569,555 | B2 | | 8/2009 | Karaolis | | |
| 7,592,326 | B2 | * | 9/2009 | Karaolis | ............ | A61K 31/7076 |
| | | | | | | 514/45 |
| 7,709,458 | B2 | | 5/2010 | Karaolis et al. | | |
| 8,012,469 | B2 | | 9/2011 | Levitsky et al. | | |
| 8,283,328 | B2 | | 10/2012 | Krieg et al. | | |
| 8,304,396 | B2 | | 11/2012 | Krieg et al. | | |
| 8,367,716 | B2 | | 2/2013 | Karaolis | | |
| 8,450,293 | B2 | | 5/2013 | Jones et al. | | |
| 9,061,048 | B2 | | 6/2015 | Portnoy et al. | | |
| 2001/0041682 | A1 | | 11/2001 | Stutts et al. | | |
| 2002/0140414 | A1 | | 10/2002 | Sohn et al. | | |
| 2002/0150588 | A1 | | 10/2002 | Allison et al. | | |

(Continued)

FOREIGN PATENT DOCUMENTS

| WO | 2005030186 A2 | 4/2005 |
| WO | 2005039535 A1 | 5/2005 |

(Continued)

OTHER PUBLICATIONS

Burger's Medicinal Chemistry and Drug Discovery, Fifth Edition, published 1994 by Wiley-Interscience, edited by Manfred E. Wolff, pp. 975-977.*
Richard B. Silverman, The Organic Chemistry of Drug Design and Drug Action, Published 1992 by Academic Press, pp. 352-397.*
Testa et al., "Prodrug Resarch: futile or fertile?" Biochemical Pharmacology (2004) vol. 68 pp. 2097-2106.*
Stella, "Prodrugs as Therapeutics" Expert Opinion on Therapeutic Patents (2004) vol. 14 No. 3 pp. 277-280.*
Ettmayer et al., "Lessons Learned from Marketed and Investigational Prodrugs" Journal of Medicinal Chemistry (2004) vol. 47 No. 10 pp. 2393-2404.*
De Grujil et al., "Whole-cell cancer vaccination: from autologous to allogeneic tumor- and dendritic cell-based vaccines" Cancer Immunol Immunother (2008) vol. 57 pp. 1569-1577.*

(Continued)

*Primary Examiner* — Eric Olson
(74) *Attorney, Agent, or Firm* — Acuity Law Group, P.C.; Michael A. Whittaker

(57) ABSTRACT

It is an object of the present invention to provide novel and highly active cyclic-di-nucleotide (CDN) immune stimulators that activates DCs via a recently discovered cytoplasmic receptor known as STING (Stimulator of Interferon Genes). In particular, the CDNs of the present invention are provided in the form of a composition comprising one or more cyclic purine dinucleotides that induce STING-dependent TBK1 activation, wherein the cyclic purine dinuclotides present in the composition are substantially pure Rp,Rp or Rp,Sp stereoisomers, and particularly substantially pure Rp,Rp, or RpSp CDN thiophosphate diastereomers.

11 Claims, 17 Drawing Sheets

(56) References Cited

U.S. PATENT DOCUMENTS

| | | | |
|---|---|---|---|
| 2003/0138413 A1 | 7/2003 | Vicari et al. | |
| 2005/0281783 A1 | 12/2005 | Kinch et al. | |
| 2006/0040887 A1 | 2/2006 | Karaolis | |
| 2006/0286549 A1 | 12/2006 | Sohn et al. | |
| 2007/0059683 A1 | 3/2007 | Barber et al. | |
| 2007/0224210 A1 | 9/2007 | Krieg et al. | |
| 2007/0244059 A1 | 10/2007 | Karaolis | |
| 2007/0281897 A1 | 12/2007 | Karaolis | |
| 2008/0076778 A1 | 3/2008 | Ossovskaya et al. | |
| 2008/0286296 A1* | 11/2008 | Ebensen | A61K 31/7084 424/194.1 |
| 2010/0150946 A1 | 6/2010 | Jooss et al. | |
| 2010/0310602 A1 | 12/2010 | Reed et al. | |
| 2011/0081674 A1 | 4/2011 | Han et al. | |
| 2011/0262485 A1 | 10/2011 | Barber | |
| 2011/0287948 A1 | 11/2011 | Suresh et al. | |
| 2012/0041057 A1 | 2/2012 | Jones et al. | |
| 2012/0164107 A1 | 6/2012 | Portnoy et al. | |
| 2012/0178710 A1 | 7/2012 | Jones et al. | |
| 2014/0205653 A1 | 7/2014 | Dubensky et al. | |
| 2014/0329889 A1 | 11/2014 | Vance et al. | |
| 2014/0341976 A1 | 11/2014 | Dubensky et al. | |
| 2015/0056224 A1* | 2/2015 | Dubensky, Jr. | A61K 31/7084 424/184.1 |

FOREIGN PATENT DOCUMENTS

| | | |
|---|---|---|
| WO | 2005087238 A2 | 9/2005 |
| WO | 2005089777 A1 | 9/2005 |
| WO | 2007054279 A2 | 5/2007 |
| WO | 2007064945 A2 | 6/2007 |
| WO | 2010017248 A2 | 2/2010 |
| WO | 2010067262 A1 | 6/2010 |
| WO | 2010104883 A1 | 9/2010 |
| WO | 2011003025 A1 | 1/2011 |
| WO | 2011136828 A1 | 11/2011 |
| WO | 2011139769 A2 | 11/2011 |
| WO | 2012068360 A1 | 5/2012 |
| WO | 2012088155 A1 | 6/2012 |
| WO | 2012139209 A1 | 10/2012 |
| WO | 2013086331 A1 | 6/2013 |
| WO | 2013166000 A1 | 11/2013 |
| WO | 2013185052 A1 | 12/2013 |
| WO | 2014093936 A1 | 6/2014 |
| WO | 2014099824 A1 | 6/2014 |
| WO | 2014179335 A1 | 11/2014 |
| WO | 2014179760 A1 | 11/2014 |
| WO | 2014189805 A1 | 11/2014 |
| WO | 2014189806 A1 | 11/2014 |
| WO | 2015017652 A1 | 2/2015 |
| WO | 2015061294 A2 | 4/2015 |
| WO | 2015074145 A1 | 5/2015 |
| WO | 2015077354 A1 | 5/2015 |
| WO | 2015108595 A1 | 7/2015 |
| WO | 2015085565 A1 | 12/2015 |

OTHER PUBLICATIONS

Krishnamachari et al., "Nanoparticle Delivery Systems in Cancer Vaccines" Pharm Res (2011) vol. 28 pp. 215-236.*

International Search Report and Written Opinion issued in PCT/US2013/075189 dated Mar. 11, 2014.

Shu et al., Structure of STING bound to cyclic di-GMP reveals the mechanism of cyclic dinucleotide recognition by the immune system. Nat Struct Mol Biol. Jun. 24, 2012;19(7):722-724.

Tanaka and Chen, STING Specifies IRF3 phosphorylation by TBK1 in the Cytosolic DNA Signaling Pathway. Sci Signal. Mar. 6, 2012;5(214):ra20 (19 pages).

Suzuki et al., Identification of Natural Antigenic Peptides of a Human Gastric Signet Ring Cell Carcinoma Recognized by HLA-A31-Restricted Cytotoxic T Lymphocytes. J Immunol. Sep. 1, 1999;163(5):2783-2791.

Suzuki et al., Practical Synthesis of Cyclic Bis(3'-5')diadenylic Acid (c-di-AMP). Chem Lett. 2011;40(10):1113-1114.

Takahashi et al., 707-AP Peptide Recognized by Human Antibody Induces Human Leukocyte Antigen A2-Restricted Cytotoxic T Lymphocyte Killing of Melanoma. Clin Cancer Res. Aug. 1997;3(8):1363-1370.

Tamayo et al., Roles of Cyclic Diguanylate in the Regulation of Bacterial Pathogenesis. Annu Rev Microbiol. 2007;61:131-148.

Tamura et al., Identification of Cyclophilin B-derived Peptides Capable of Inducing Histocompatibility Leukocyte Antigen-A2-restricted and Tumor-specific Cytotoxic T Lymphocytes. Jpn J Cancer Res. Jul. 2001;92(7):762-767.

Tanaka and Chen, STING Specifies IRF3 Phosphorylation by TBK1 in the Cytosolic DNA Signaling Pathway. Sci Signal. Mar. 6, 2012;5(214):ra20.

Tanaka et al., Expression of Tumor-Rejection Antigens in Gynecologic Cancers. Jpn J Cancer Res. Nov. 2000;91(11):1177-1184.

Tannapfel et al., BRAF Gene Mutations are Rare Events in Gastroenteropancreatic Neuroendocrine Tumors. Am J Clin Pathol. Feb. 2005;123(2):256-2601.

Tewari et al., Poly(I:C) is an effective adjuvant for antibody and multi-functional CD4+ T cell responses to Plasmodium falciparum circumsporozoite protein (CSP) and αDEC-CSP in Non Human Primates. Vaccine. Oct. 21, 2010;28(45):7256-7266.

Treurnicht et al., HHV-8 subtypes in South Africa: identification of a case suggesting a novel B variant. J Med Virol. Feb. 2002;66(2):235-240.

Trimble et al., Comparison of the CD8+ T cell responses and antitumor effects generated by DNA vaccine administered through gene gun, biojector, and syringe. Vaccine. Sep. 8, 2003;21(25-26):4036-4042.

Trincado et al., Human Cytomegalovirus Strains Associated With Congenital and Perinatal Infections. J Med Virol. Aug. 2000;61(4):481-487.

Tsang et al., Phenotypic Stability of a Cytotoxic T-Cell Line Directed Against an Immunodominant Epitope of Human Carcinoembryonic Antigen. Clin Cancer Res. Dec. 1997;3(12 Pt 1):2439-2449.

Tsao and Sober, Melanoma Treatment Update. Dermatol Clin. Apr. 2005;23(2):323-333.

Tsuruma et al., Phase I clinical study of anti-apoptosis protein, survivin-derived peptide vaccine therapy for patients with advanced or recurrent colorectal cancer. J Transl Med. Jun. 13, 2004;2(1):19 (11 pages).

Vallejo et al., Nucleotide Sequence and Restriction Fragment-Length Polymorphism Analysis of Human T-Cell Lymphotropic Virus Type II (HTLV-II) in Southern Europe: Evidence for the HTLV-IIa and HTLV-IIb Subtypes. J Acquir Immune Defic Syndr Hum Retrovirol. Dec. 1, 1996;13(4):384-391.

Van Den Eynde et al., A New Antigen Recognized by Cytolytic T Lymphocytes on a Human Kidney Tumor Results From Reverse Strand Transcription. J Exp Med. Dec. 20, 1999;190(12):1793-1800.

Van Erp et al., Application of a sol particle immunoassay to the determination of affinity constants of monoclonal antibodies. J Immunoassay. 1991;12(3):425-443.

Vance et al., Patterns of Pathogenesis: Discrimination of Pathogenic and Nonpathogenic Microbes by the Innate Immune System. Cell Host Microbe. Jul. 23, 2009;6(1):10-21.

Vandamme et al., African Origin of Human T-Lymphotropic Virus Type 2 (HTLV-2) Supported by a Potential New HTLV-2d Subtype in Congolese Bambuti Efe Pygmies. J Virol. May 1998;72(5):4327-4340.

Vilas Boas et al., Cytomegalovirus Glycoprotein B Genotypes and Central Nervous System Disease in AIDS Patients. J Med Virol. Nov. 2003;71(3):404-407.

Vilchez and Butel, Emergent Human Pathogen Simian Virus 40 and Its Role in Cancer. Clin Microbiol Rev. Jul. 2004;17(3):495-508.

Virok et al., Chlamydial Infection Induces Pathobiotype-Specific Protein Tyrosine Phosphorylation in Epithelial Cells. Infect Immun. Apr. 2005;73(4):1939-1946.

(56) References Cited

OTHER PUBLICATIONS

Von Lindern et al., The Translocation (6;9), Associated with a Specific Subtype of Acute Myeloid Leukemia, Results in the Fusion of Two Genes, dek and can, and the Expression of a Chimeric, Leukemia-Specific dek-can mRNA. Mol Cell Biol. Apr. 1992;12(4):1687-1697.

Waltregny et al., Screening of histone deacetylases (HDAC) expression in human prostate cancer reveals distinct class I HDAC profiles between epithelial and stromal cells. Eur J Histochem. Jul.-Sep. 2004;48(3):273-290.

Wang et al., Alterations of APC, c-met, and p53 Genes in Tumor Tissue and Serum of Patients with Gastric Cancers. J Surg Res. Aug. 2004;120(2):242-248.

Wang et al., Cloning Genes Encoding MHC Class II—Restricted Antigens: Mutated CDC27 as a Tumor Antigen. Science. May 21, 1999;284(5418):1351-1354.

Wang et al., Identification of a Novel Major Histocompatibility Complex Class II—restricted Tumor Antigen Resulting from a Chromosomal Rearrangement Recognized by CD4+ T Cells. J Exp Med. May 17, 1999;189(10):1659-1668.

Ward et al., Binding activities of a repertoire of single immunoglobulin variable domains secreted from *Escherichia coli*. Nature. Oct. 12, 1989;341(6242):544-546.

Weaver et al., Genetic determinants of Venezuelan equine encephalitis emergence. Arch Virol Suppl. 2004; (18):43-64.

Weaver et al., Venezuelan Equine Encephalitis. Annu Rev Entomol. 2004;49:141-174.

Wells et al., Swine Influenza Virus Infections Transmission. From III Pigs to Humans at a Wisconsin Agricultural Fair and Subsequent Probable Person-to-Person Transmission. JAMA. Jan. 23-30, 1991;265(4):478-481.

Wentworth et al., An Influenza A (HINI) Virus, Closely Related to Swine Influenza Virus, Responsible for a Fatal Case of Human Influenza. J Virol. Apr. 1994;68(4):2051-2058.

Wille-Reece et al., HIV Gag protein conjugated to a Toll-like receptor 7/8 agonist improves the magnitude and quality of Th1 and CD8+ T cell responses in nonhuman primates. Proc Natl Acad Sci U S A. Oct. 18, 2005;102(42):15190-15194.

Wille-Reece et al., Immunization with HIV-1 Gag Protein Conjugated to a TLR7/8 Agonist Results in the Generation of HIV-1 Gag-Specific Th1 and CD8+ T Cell Responses. J Immunol. Jun. 15, 2005;174(12):7676-7683.

Wille-Reece et al., Toll-like receptor agonists influence the magnitude and quality of memory T cell responses after prime-boost immunization in nonhuman primates. J Exp Med. May 15, 2006;203(5):1249-1258.

Wilson et al., Simplified conjugation chemistry for coupling peptides to F(ab') fragments: autologous red cell agglutination assay for HIV-1 antibodies. J Immunol Methods. Oct. 14, 1994;175(2):267-273.

Witte et al., Innate Immune Pathways Triggered by Listeria monocytogenes and Their Role in the Induction of Cell-Mediated Immunity. Adv Immunol. 2012;113:135-156.

Woodward et al., c-di-AMP secreted by intracellular Listeria monocytogenes activates a host type I interferon response. Science. Jun. 25, 2010;328(5986):1703-1705.

Woycechowsky and Raines, Native Disulfide Bond Formation in Proteins. Curr Opin Chem Biol. Oct. 2000;4(5):533-539.

Yan et al., Synthesis and immunostimulatory properties of the phosphorothioate analogues of cdiGMP. Bioorg Med Chem Lett. Oct. 15, 2008;18(20):5631-5634.

Yarmush et al., Coupling of antibody-binding fragments to solid-phase supports: site-directed binding of F(ab')2 fragments. J Biochem Biophys Methods. Dec. 1992;25(4):285-297.

Yi et al., Single Nucleotide Polymorphisms of Human STING Can Affect Innate Immune Response to Cyclic Dinucleotides. PLoS One. Oct. 21, 2013;8(10):e77846.

Yin et al., Cyclic di-GMP Sensing via the Innate Immune Signaling Protein STING. Mol Mol Cell. Jun. 29, 2012;46(6):735-745.

Zaremba et al., Identification of an Enhancer Agonist Cytotoxic T Lymphocyte Peptide from Human Carcinoembryonic Antigen. Cancer Res. Oct. 15, 1997;57(20):4570-4577.

Zeier et al., New Ecological Aspects of Hantavirus Infection: A Change of a Paradigm and a Challenge of Prevention—A Review. Virus Genes. Mar. 2005;30(2):157-180.

Zhang et al., c-di-GMP Displays a Monovalent Metal Ion-Dependent Polymorphism. J Am Chem Soc. Dec. 29, 2004;126(51):16700-16701.

Zhao et al., Thiophosphate Analogs of c-di-GMP: Impact on Polymorphism. Nucleosides Nucleotides Nucleic Acids. May 2009;28(5):352-378.

Zhou et al., Endo-S-c-di-GMP Analogues—Polymorphism and Binding Studies with Class I Riboswitch. Molecules. Nov. 9, 2012;17(11):13376-13389.

Zhou et al., Potent suppression of c-di-GMP synthesis via I-site allosteric inhibition of diguanylate cyclases with 2'-F-c-di-GMP. Bioorg Med Chem. Jul. 15, 2013;21(14):4396-4404.

O'Neill, Immunology. Sensing the dark side of DNA. Science. Feb. 15, 2013;339(6121):763-764.

Ora et al., Hydrolytic reactions of cyclic bis(3'-5')diadenylic acid (c-di-AMP). J Physical Organic Chem. 2013; 26(3)218-225.

Pardoll and Drake, Immunotherapy earns its spot in the ranks of cancer therapy. J Exp Med. Feb. 13, 2012;209(2):201-209.

Pardoll, The blockade of immune checkpoints in cancer immunotherapy. Nat Rev Cancer. Mar. 22, 2012;12(4):252-264.

Parvatiyar et al., DDX41 recognizes the bacterial secondary messengers cyclic di-GMP and cyclic di-AMP to activate a type I interferon immune response. Nat Immunol. Dec. 2012;13(12):1155-1161.

Prantner et al., 5,6-Dimethylxanthenone-4-acetic Acid (DMXAA) Activates Stimulator of Interferon Gene (STING)-dependent Innate Immune Pathways and is Regulated by Mitochondrial Membrane Potential. J Biol Chem. Nov. 16, 2012;287(47):39776-39788.

Roembke et al., A cyclic dinucleotide containing 2-aminopurine is a general fluorescent sensor for c-di-GMP and 3',3'-cGAMP. Mol Biosyst. Jun. 2014;10(6):1568-1575.

Sawai et al., Preparation and Properties of Oligocytidylates with 2'-5' Internucleotide Linkage. Bull Chem Soc Jpn 1985;58(1):361-366.

Sawai et al., Synthesis of 2'-5' Linked Oligouridylates in Aqueous Medium Using the Pd2+ Ion. Chem Pharm Bull. 1981;29(8):2237-2245.

Shanahan et al., Identification of c-di-GMP Derivatives Resistant to an EAL Domain Phosphodiesterase. Biochemistry. Jan. 15, 2013;52(2):365-377.

Silverman, the Organic Chemistry of Drug Design and Drug Action, Published 1992 by Academic Press, pp. 352-397.

Stella, Prodrugs and Therapeutics. Expert Opinion on Therapeutic Patents 2004;14(3):277-280.

Sun and Bevan, Defective CD8 T Cell Memory Following Acute Infection Without CD4 T Cell Help. Science. Apr. 11, 2003;300(5617):339-342.

Tannock et al., Docetaxel plus Prednisone or Mitoxantrone plus Prednisone for Advanced Prostate Cancer. N Engl J Med. Oct. 7, 2004;351(15):1502-1512.

Testa et al., Prodrug Research: futile or fertile? Biochem Pharmacol. Dec. 1, 2004;68(11):2097-2106.

Tezuka et al., Synthesis of 2'-Modified Cyclic Bis(3'-5')diadenylic Acids (c-di-AMPs) and Their Promotion of Cell Division in a freshwater Green Alga. Chem Lett. 41: 1723-25, 2012.

Tijono et al., Identification of human-selective analogues of the vascular-disrupting agent 5,6-dimethylxanthenone-4-acetic acid (DMXAA). Br J Cancer. Apr. 2, 2013;108(6):1306-1315.

Topalian et al., Cancer Immunotherapy Comes of Age. J Clin Oncol 2011.

Urata et al., Regio- and Diastereo-Selectivity of Montmorillonite-Catalyzed Oligomerization of Racemic Adenosine 5'-Phosphorimidazolide. Nucleosides Nucleotides Nucleic Acids. Apr. 2008;27(4):421-430.

(56) References Cited

OTHER PUBLICATIONS

Van Elsas et al., Elucidating the Autoimmune and Antitumor Effector Mechnaisms of a Treatment Based on Cytotoxic T Lymphocyte Antigen-4 Blockade in Combination with a B16 Melanoma Vaccine: Comparison of Prophylaxis and Therapy. J Exp Med. Aug. 20, 2001,194(4):481-489.
Waitz et al., Potent Induction of Tumor Immunity by Combining Tumor Cryoablation with Anti-CTLA-4 Therapy. Cancer Res. Jan. 15, 2012;72(2):430-439.
Woodward et al., Supporting Online Material for c-di-AMP Secreted by Intracellular Listeria monocytogenes Activates a Host Type I Interferon Response. May 27, 2010 on Science Express May 27, 2010;DOI:10.1126/science.1189801 (15 pages).
Wu et al., Cyclic GMP-AMP is an Endogenous Second Messenger in Innate Immune Signaling by Cytosolic DNA. Science. Feb. 15, 2013;339(6121):826-830.
Yan and Aguilar, Synthesis of 3',5'-cyclic diguanylic acid (cdiGMP) using 1-(4-chlorophenyl)-4-ethoxypiperidin-4-yl as a protecting group for 2'-hydroxy functions of ribonucleosides. Nucleosides Nucleotides Nucleic Acids. 2007;26 (2):189-204.
Zhang et al., Cyclic GMP-AMP Containing Mixed Phosphodiester Linkages is an Endogenous High-Affinity Ligand for STING. Mol Cell. Jul. 25, 2013;51(2):226-235.
International Search Report and Written Opinion issued in PCT/US2013/044744 dated Nov. 7, 2013.
Extended European Search Report and Written Opinion issued in PCT/US2013/044744 (EP 13799826) dated Nov. 20, 2015.
Burdette et al., STING is a direct innate immune sensor of cyclic-di-GMP. Nature. Sep. 25, 2011;478(7370):515-518.
Search Report and Written Opinion issued by IPOS in Singapore patent application No. 11201407875U dated Sep. 15, 2015.
Non Final Office Action issued in U.S. Appl. No. 13/912,960 dated Jul. 15, 2015.
Non Final Office Action issued in U.S. Appl. No. 14/280,667 dated Nov. 19, 2015.
Non Final Office Action issued in U.S. Appl. No. 14/280,668 dated Dec. 3, 2015.
Non Final Office Action issued in U.S. Appl. No. 14/268,967 dated Nov. 9, 2015.
Search Report and Written Opinion issued by IPOS in Singapore patent application No. 11201502796R dated Jan. 8, 2016.
Abutaily et al., Cadherins, catenins and APC in pleural malignant mesothelioma. J Pathol. Nov. 2003;201(3):355-362.
Adler-Moore et al., Characterization of the murine Th2 response to immunization with liposomal M2e influenza vaccine. Vaccine. Jun. 15, 2011;29(27):4460-4468.
Aguilar et al., Endemic Venezuelan Equine Encephalitis in Northern Peru. Emerg Infect Dis. May 2004;10(5):880-888.
Ahmed et al., Assessing the Safety of Adjuvanted Vaccines. Sci Transl Med. Jul. 27, 2011;3(93):93rv2.
Ahn et al., All CVB Serotypes and Clinical Isolates Induce Irreversible Cytopathic Effects in Primary Cardiomyocytes. J Med Virol. Feb. 2005;75(2):290-294.
Altwein and Luboldt, Prognostic Factors for Carcinoma of the Prostate. Urol Int. 1999:63(1):62-71.
Alvarez-Lafuente et al., Human parvovirus B19, varicella zoster virus, and human herpes virus 6 in temporal artery biopsy specimens of patients with giant cell arteritis: analysis with quantitative real time polymerase chain reaction. Ann Rheum Dis. May 2005;64(5):780-782.
Andersen and thor Straten, Survivin—a universal tumor antigen. Histol Histopathol. Apr. 2002;17(2):669-675.
Argani et al., Discovery of New Markers of Cancer through Serial Analysis of Gene Expression Prostate Stem Cell Antigen is Overexpressed in Pancreatic Adenocarcinoma. Cancer Res. Jun. 1, 2001;61(11):4320-4324.
Arora et al., Identification of Differentially Expressed Genes in Oral Squamous Cell Carcinoma. Mol Carcinog. Feb. 2005;42(2):97-108.

Attoui et al., Comparative sequence analysis of American, European and Asian isolates of viruses in the genus Coltivirus. J Gen Virol. Oct. 1998;79 ( Pt 10):2481-2489.
Badovinac et al., Accelerated CD8+ T-cell memory and prime-boost response after dendritic-cell vaccination. Nat Med. Jul. 2005;11(7):748-756.
Bahjat et al., Cytosolic Entry Controls CD8+-T-Cell Potency during Bacterial Infection. Infect Immun. Nov. 2006;74(11):6387-6397.
Bahjat et al., Suppression of Cell-Mediated Immunity following Recognition of Phagosome-Confined Bacteria. PLoS Pathog. Sep. 2009;5(9):e1000568.
Bala et al., PLGA Nanoparticles in Drug Delivery: The State of the Art. Crit Rev Ther Drug Carrier Syst. 2004;21(5):387-422.
Baldwin et al., The Importance of Adjuvant Formulation in the Development of a Tuberculosis Vaccine. J Immunol. Mar. 1, 2012;188(5):2189-2197.
Barbanti-Brodano et al., Simian virus 40 infection in humans and association with human diseases: results and hypotheses. Virology. Jan. 5, 2004;318(1):1-9.
Barber, Cytoplasmic DNA innate immune pathways. Immunol Rev. Sep. 2011;243(1):99-108.
Barber, Sting-dependent signaling. Nat Immunol. Sep. 20, 2011;12(10):929-930.
Barthold et al., Infectivity, disease patterns, and serologic profiles of reovirus serotypes 1, 2, and 3 in infant and weanling mice. Lab Anim Sci. Oct. 1993;43(5):425-430.
Battistini et al., Stereoselective Synthesis of Cyclic Dinucleotide Phosphorothioates. Tetrahedron, 1993;49(5):1115-1132.
Baurain et al., High Frequency of Autologous Anti-Melanoma CTL Directed Against an Antigen Generated by a Point Mutation in a New Helicase Gene. J Immunol. Jun. 1, 2000;164(11):6057-6066.
Bevanger et al., Competitive Enzyme Immunoassay for Antibodies to a 43,000-Molecular-Weight Francisella tularensis Outer Membrane Protein for the Diagnosis of Tularemia. J Clin Microbiol. May 1989;27(5):922-926.
Bhigjee et al., Sequence of the env gene of some KwaZulu-Natal, South African strains of HTLV type I. AIDS Res Hum Retroviruses. Sep. 1, 1999;15(13):1229-1233.
Biagini et al., Simultaneous measurement of specific serum IgG responses to five select agents. Anal Bioanal Chem. Jun. 2005;382(4):1027-1034.
Bondurant et al., Definition of an Immunogenic RegionWithin the OvarianTumor Antigen Stratum Corneum Chymotryptic Enzyme. Clin Cancer Res. May 1, 2005;11(9):3446-3454.
Brezniceanu et al., HMGB1 inhibits cell death in yeast and mammalian cells and is abundantly expressed in human breast carcinoma. FASEB J. Jul. 2003;17(10):1295-1297.
Brian and Baric, Coronavirus Genome Structure and Replication. Curr Top Microbiol Immunol. 2005;287:1-30.
Brinkmann et al., Novel Genes in the PAGE and GAGE Family of Tumor Antigens Found by Homology Walking in the dbEST Database. Cancer Res. Apr. 1, 1999;59(7):1445-1448.
Brockstedt et al., Killed but metabolically active microbes: a new vaccine paradigm for eliciting effector T-cell responses and protective immunity. Nat Med. Aug. 2005;11(8):853-860.
Bronte et al., Genetic Vaccination with "Self" Tyrosinase-related Protein 2 Causes Melanoma Eradication but not Vitiligo. Cancer Res. Jan. 15, 2000;60(2):253-258.
Brown et al., Complete Genomic Sequencing Shows that Polioviruses and Members of Human Enterovirus Species C are Closely Related in the Noncapsid Coding Region. J Virol. Aug. 2003;77(16):8973-8984.
Brown, Variants of B19. Dev Biol (Basel). 2004;118:71-77.
Burdette and Vance, STING and the innate immune response to nucleic acids in the cytosol. Nat Immunol. Jan. 2013;14(1):19-26.
Burdette et al., STING is a direct innate immune sensor of cyclic di-GMP. Nature. Sep. 25, 2011;478(7370):515-518 doi:10.1038/nature10429.
Capdepont et al., New Insights in HTLV-I Phylogeny by Sequencing and Analyzing the Entire Envelope Gene. AIDS Res Hum Retroviruses. Jan. 2005;21(1):28-42.

(56) References Cited

OTHER PUBLICATIONS

Capurro et al., Glypican-3: A Novel Serum and Histochemical Marker for Hepatocellular Carcinoma. Gastroenterology. Jul. 2003;125(1):89-97.

Carbone et al., New developments about the association of SV40 with human mesothelioma. Oncogene. Aug. 11, 2003;22(33):5173-5180.

Chan et al., In Situ Hybridization Study of PSP94 (Prostatic Secretory Protein of 94 Amino Acids) Expression in Human Prostates. Prostate. Oct. 1, 1999;41(2):99-109.

Chang et al., A Phase I Trial of Tumor Lysate-Pulsed Dendritic Cells in the Treatment of Advanced Cancer. Clin Cancer Res. Apr. 2002;8(4):1021-1032.

Chen et al., Immunodominant CD41 responses identified in a patient vaccinated with full-length NY-ESO-1 formulated with ISCOMATRIX adjuvant. Proc Natl Acad Sci USA. Jun. 22, 2004;101(25):9363-9368.

Chern et al., Glycoprotein B Subtyping of Cytomegalovirus (CMV) in the Vitreous of Patients with AIDS and CMV Retinitis. J Infect Dis. Oct. 1998;178(4):1149-1153.

Chiari et al., Two Antigens Recognized by Autologous Cytolytic T Lymphocytes on a Melanoma Result from a Single Point Mutation in an Essential Housekeeping Gene. Cancer Res. Nov. 15, 1999;59(22):5785-5792.

Christiansen et al., Polarity of Prostate Specific Membrane Antigen, Prostate Stem Cell Antigen, and Prostate Specific Antigen in Prostate Tissue and in a Cultured Epithelial Cell Line. Prostate. Apr. 1, 2003;55(1):9-19.

Clements et al., Adenomatous Polyposis Coli/β-Catenin Interaction and Downstream Targets: Altered Gene Expression in Gastrointestinal Tumors. Clin Colorectal Cancer. Aug. 2003;3(2):113-120.

Clifton et al., A chlamydial type III translocated protein is tyrosine-phosphorylated at the site of entry and associated with recruitment of actin. Proc Natl Acad Sci USA. Jul. 6, 2004;101(27):10166-10171.

Clinton et al., A Comparative Study of Four Serological Tumor Markers for the Detection of Breast Cancer. Biomed Sci Instrum. 2003;39:408-414.

Cobaleda et al., A primitive hematopoietic cell is the target for the leukemic transformation in human Philadelphia-positive acute lymphoblastic leukemia. Blood. Feb. 1, 2000;95(3):1007-1013.

Codrington et al., Analysis of ETV6/AML1 abnormalities in acute lymphoblastic leukaemia: incidence, alternative spliced forms and minimal residual disease value. Br J Haematol. Dec. 2000;111(4):1071-1079.

Coffman et al., Vaccine adjuvants: putting innate immunity to work. Immunity. Oct. 29, 2010;33(4):492-503.

Gulmann et al., Adenomatous Polyposis Coli Gene, beta-Catenin, and E-Cadherin Expression in Proximal and Distal Gastric Cancers and Precursor Lesions. Appl Immunohistochem Mol Morphol. Sep. 2003;11(3):230-237.

Gupta et al., Refolding, purification, and crystallization of apical membrane antigen 1 from Plasmodium falciparum. Protein Expr Puruf. May 2005;41(1):186-198.

Haddad et al., Novel antigen identification method for discovery of protective malaria antigens by rapid testing of DNA vaccines encoding exons from the parasite genome. Infect Immun. Mar. 2004;72(3):1594-1602.

Hakansson et al., Establishment and phenotypic characterization of human U937 cells with inducible P210 BCR/ABL expression reveals upregulation of CEACAM1 (CD66a). (2004) Leukemia 18:538-547.

Harris et al., The Biological and Therapeutic Importance of Gastrin Gene Expression in Pancreatic Adenocarcinomas. Cancer Res. Aug. 15, 2004;64(16):5624-5631.

Harty and Badovinac, Shaping and reshaping CD8+ T-cell memory. Nat Rev Immunol. Feb. 2008;8(2):107-19-119.

Hashido et al., Evaluation of an Enzyme-Linked Immunosorbent Assay Based on Binding Inhibition for Type-Specific Quantification of Poliovirus Neutralization-Relevant Antibodies. Microbiol Immunol. 1999;43(1):73-77.

Hassan et al., Mesothelin: A New Target for Immunotherapy. Clin Cancer Res. Jun. 15 2004;10(12 Pt 1):3937-3942.

Havlasova et al., Mapping of immunoreactive antigens of Francisella tularensis live vaccine strain. Proteomics. Jul. 2002;2(7):857-867.

Havlasova et al., Proteomic analysis of anti-Francisella tularensis LVS antibody response in murine model of tularemia. Proteomics. May 2005;5(8):2090-2103.

Hayakawa, A facile synthesis of cyclic bis(30!50)diguanylic acid. Tetrahedron 2003;59:6465-6471.

He et al., Complexes of Poliovirus Serotypes with Their Common Cellular Receptor, CD155. J Virol. Apr. 2003;77(8):4827-4835.

Hirose et al., Incidence of Diffuse Large B-Cell Lymphoma of Germinal Center B-Cell Origin in Whole Diffuse Large B-Cell Lymphoma: Tissue Fluorescence In Situ Hybridization Using t(14;18) Compared with Immunohistochemistry. Int J Hematol. Jan. 2005;81(1):48-57.

Hoffman et al., Strategy for development of a pre-erythrocytic Plasmodium falciparum DNA vaccine for human use. Vaccine. Jun. 1997;15(8):842-845.

Hoke, History of U.S. Military Contributions to the Study of Viral Encephalitis. Mil Med. Apr. 2005;170(4 Suppl):92-105.

Hu et al., c-di-GMP as a vaccine adjuvant enhances protection against systemic methicillin-resistant Staphylococcus aureus (MRSA) infection. Vaccine. Jul. 30, 2009;27(35):4867-4873.

Hughes, Nanostructure-mediated drug delivery. Nanomedicine. Mar. 2005;1(1):22-30.

Hussain and Paterson, What is needed for effective antitumor immunotherapy? Lessons learned using Listeria monocytogenes as a live vector for HPV-associated tumors. Cancer Immunol Immunother. Jun. 2005;54(6):577-586.

Hutchinson et al., Multiplex Analysis of Cytokines in the Blood of Cynomolgus Macaques Naturally Infected With Ebola Virus (Reston Serotype). J Med Virol. Nov. 2001;65(3):561-566.

Hyodo et al., Synthesis of cyclic bis(3'-5')diguanylic acid (c-di-GMP) analogs. Tetrahedron 2006;62:3089-3094.

Iacobuzio-Donahue et al., Highly Expressed Genes in Pancreatic Ductal Adenocarcinomas: A Comprehensive Characterization and Comparison of the Transcription Profiles Obtained from Three Major Technologies. Cancer Res. Dec. 15, 2003;63(24):8614-8622.

Iqbal et al., BCL2 Translocation Defines a Unique Tumor Subset within the Germinal Center B-Cell-Like Diffuse Large B-Cell Lymphoma. Am J Pathol. Jul. 2004;165(1):159-166.

Isherwood et al., Vaccination strategies for Francisella tularensis. Adv Drug Deliv Rev. Jun. 17, 2005;57(9):1403-1414.

Ishikawa and Barber, STING an Endoplasmic Reticulum Adaptor that Facilitates Innate Immune Signaling. Nature. Oct. 2, 2008;455(7213):674-678.

Ito et al., Prostate Carcinoma Detection and Increased Prostate-Specific Antigen Levels after 4 Years in Dutch and Japanese Males Who Had no Evidence of Disease at Initial Screening. Cancer. Jan. 15, 2005;103(2):242-250.

Iwasaki and Medzhitov, Regulation of adaptive immunity by the innate immune system. Science. Jan. 15, 2010;327(5963):291-295.

Jainkittivong and Langlais, Herpes B virus infection. Oral Surg Oral Med Oral Pathol Oral Radiol Endod. Apr. 1998;85(4):399-403.

Jamieson et al., Human Torovirus: A New Nosocomial Gastrointestinal Pathogen. J Infect Dis. Nov. 1998;178(5):1263-1269.

Jansen and Shaw, Human Papillomavirus Vaccines and Prevention of Cervical Cancer. Annu Rev Med. 2004;55:319-331.

Jin et al., Identification and characterization of a loss-of-function human MPYS variant. Genes Immun. Jun. 2011;12(4):263-269.

Jin et al., MPYS is Required for IFN Response Factor 3 Activation and Type I IFN Production in the Response of Cultured Phagocytes to Bacterial Second Messengers Cyclic-di-AMP and Cyclic-di-GMP. J Immunol. Sep. 1, 2011;187(5):2595-2601.

Jung et al., Strategies Against Human Papillomavirus Infection and Cervical Cancer. J Microbiol. Dec. 2004;42(4):255-266.

(56) References Cited

OTHER PUBLICATIONS

Jungck et al., E-cadherin expression is homogeneously reduced in adenoma from patients with familial adenomatous polyposis: an immunohistochemical study of E-cadherin, beta-catenin and cyclooxygenase-2 expression. Int J Colorectal Dis. Sep. 2004;19(5):438-445.

Karaolis et al., Bacterial c-di-GMP is an Immunostimulatory Molecule. J Immunol. Feb. 15, 2007;178(4):2171-2181.

Karaolis et al., Cyclic Di-GMP Stimulates protective Innate Immunity in Bacterial Pneumonia. Infect Immun. Oct. 2007;75(10):4942-4950.

Kastenmuller et al., Protective T cell immunity in mice following protein-TLR7/8 agonist-conjugate immunization requires aggregation, type I IFN, and multiple DC subsets. J Clin Invest. May 2011;121(5):1782-1796.

Kaufman et al., Parvovirus B19 does not bind to membrane-associated globoside in vitro. Virology. Feb. 5, 2005;332(1):189-198.

Kawai and Akira, The role of pattern-recognition receptors in innate immunity: update on Toll-like receptors. Nat Immunol. May 2010;11(5):373-384.

Kedl et al., Comparative Sequence Analysis of the Reovirus S4 Genes from 13 Serotype 1 and Serotype 3 Field Isolates. J Virol. Jan. 1995;69(1):552-559.

Kim et al., Co-Crystal Structures of PKG Iβ (92-227) with cGMP and cAMP Reveal the Molecular Details of Cyclic-Nucleotide Binding. PLoS One. Apr. 19, 2011;6(4):e18413.

Kim et al., Comparison of HPV DNA vaccines employing intracellular targeting strategies. Gene Ther. Jun. 2004;11(12):1011-1018.

Krzych et al., T lymphocytes from volunteers immunized with irradiated Plasmodium falciparum sporozoites recognize liver and blood stage malaria antigens. J Immunol. Oct. 15, 1995;155(8):4072-4077.

Kubuschok et al., Expression of cancer testis antigens in pancreatic carcinoma cell lines, pancreatic adenocarcinoma and chronic pancreatitis. Int J Cancer. Apr. 20, 2004;109(4):568-575.

Kumamuru et al., T-cell receptor Vbeta gene usage by T cells reactive with the tumor-rejection antigen SART-1 in oral squamous cell carcinoma. Int J Cancer. Feb. 20, 2004;108(5):686-695.

Laheru and Jaffee, Immunotherapy for pancreatic cancer—science driving clinical progress. Nat Rev Cancer. Jun. 2005;5(6):459-467.

Lauvau et al., Priming of Memory But not Effector CD8 T Cells by a Killed Bacterial Vaccine. Science. Nov. 23, 2001;294(5547):1735-1739.

Leber et al., Distinct TLR- and NLR-Mediated Transcriptional Responses to an Intracellular Pathogen. PLoS Pathog. Jan. 2008;4(1):e6.

Lee et al., A clinical grade cocktail of cytokines and PGE2 results in uniform maturation of human monocyte-derived dendritic cells: implications for immunotherapy. Vaccine. Dec. 19, 2002;20 Suppl 4:A8-A22.

Lee et al., Immunomic analysis of human sarcoma. Proc Natl Acad Sci U S A. Mar. 4, 2003;100(5):2651-2656.

Li et al., Advanced Glycation End Products Induce Tubular Epithelial-Myofibroblast Transition through the RAGE-ERK1/2 MAP Kinase Signaling Pathway. Am J Pathol. Apr. 2004;164(4):1389-1397.

Li et al., Expression Profile of Cancer-Testis Genes in 121 Human Colorectal Cancer Tissue and Adjacent Normal Tissue. Clin Cancer Res. Mar. 1, 2005;11(5):1809-1814.

Liang et al., Microvessel density, cyclo-oxygenase 2 expression, K-ras mutation and p53 overexpression in colonic cancer. Br J Surg. Mar. 2004;91(3):355-361.

Libanova et al., The member of the cyclic di-nucleotide family bis-(3′, 5′)-cyclic dimeric inosine monophosphate exerts potent activity as mucosal adjuvant Vaccine. Mar. 2, 2010;28(10):2249-2258.

Lim et al., Molecular and phenotypic spectrum of de novo Philadelphia positive acute leukemia. Int J Mol Med. Dec. 1999;4(6):665-667.

Lin et al., Melanoma-Associated Antigens in Esophageal Adenocarcinoma Identification of Novel MAGE-A10 Splice Variants. Clin Cancer Res. Sep. 1, 2004;10(17):5708-5716.

Lubong Sabado et al., In Vitro Priming Recapitulates In Vivo HIV-1 Specific T Cell Responses, Revealing Rapid Loss of Virus Reactive CD4+ T Cells in Acute HIV-1 Infection. PLoS One. 2009;4(1):e4256 (13 pages).

Lucas et al., MAGE-B5, MAGE-B6, MAGE-C2, and MAGE-C3: four new members of the MAGE family with tumor-specific expression. Int J Cancer. Jul. 1, 2000;87(1):55-60.

Machlenkin et al., Human CTL Epitopes Prostatic Acid Phosphatase-3 and Six-Transmembrane Epithelial Antigen of Prostate-3 as Candidates for Prostate Cancer Immunotherapy. Cancer Res. Jul. 15, 2005;65(14):6435-6442.

Madhun et al., Intranasal c-di-GMP-adjuvanted plant-derived H5 influenza vaccine induces multifunctional Th1 CD4+ cells and strong mucosal and systemic antibody responses in mice. Vaccine. Jul. 12, 2011;29(31):4973-4982.

Mandruzzato et al., A CASP-8 Mutation Recognized by Cytolytic T Lymphocytes on a Human Head and Neck Carcinoma. J Exp Med. Aug. 29, 1997;186(5):785-793.

Matsumoto et al., Expression of the SART-1 antigens in uterine cancers. Jpn J Cancer Res. Dec. 1998;89(12):1292-1295.

Matsushita et al., Preferentially Expressed Antigen of Melanoma (PRAME) in the Development of Diagnostic and Therapeutic Methods for Hematological Malignancies. Leuk Lymphoma. Mar. 2003;44(3):439-444.

Mayo et al., Mdm-2 Phosphorylation by DNA-dependent Protein Kinase Prevents Interaction with p53. Cancer Res. Nov. 15, 1997;57(22):5013-5016.

McCool et al., Roles of calreticulin and calnexin during mucin synthesis in LS180 and HT29/A1 human colonic adenocarcinoma cells. Biochem J. Aug. 1, 1999;341 ( Pt 3):593-600.

McCune et al., Active specific immunotherapy with tumor cells and Cornebacterium parvum: A phase I study. Cancer. May 1979;43(5):1619-1623.

McWhirter et al., A host type I interferon response is induced by cytosolic sensing of the bacterial second messenger cyclic-di-GMP. J Exp Med. Aug. 31, 2009;206(9):1899-1911.

Millon et al., Detection of Prostate-Specific Antigen- or Prostate-Specific Membrane Antigen-Positive Circulating Cells in Prostatic Cancer Patients: Clinical Implications. Eur Urol. Oct. 1999;36(4):278-285.

Molijn et al., Molecular diagnosis of human papillomavirus (HPV) infections. J Clin Virol. Mar. 2005;32 Suppl 1: S43-51.

Moreau-Aubry et al., A Processed Pseudogene Codes for a New Antigen Recognized by a Cd8+ T Cell Clone on Melanoma. J Exp Med. May 1, 2000;191(9):1617-1624.

Morse et al., A Phase I Study of Active Immunotherapy with Carcinoembryonic Antigen Peptide (CAP-1)-pulsed Autologous Human Cultured Dendritic Cells in Patients with Metastatic Malignancies Expressing Carcinoembryonic Antigen. Clin Cancer Res. Jun. 1999;5(6):1331-1338.

Muderhwa et al., Oil-in-water liposomal emulsions: Characterization and potential use in vaccine delivery. J Pharm Sci. Dec. 1999;88(12):1332-1339.

Mukhopadhyay et al., A structural perspective of the flavivirus life cycle. Nat Rev Microbiol. Jan. 2005;3(1):13-22.

Mulders et al., Tumor antigens and markers in renal cell carcinoma. Urol Clin North Am. Aug. 2003;30(3):455-465.

Muller et al., MeCP2 and MBD2 expression in human neoplastic and non-neoplastic breast tissue and its association with oestrogen receptor status. Br J Cancer. Nov. 17, 2003;89(10):1934-1939.

Muminova et al., Characterization of human mesothelin transcripts in ovarian and pancreatic cancer. BMC Cancer. May 12, 2004;4:19.

Nair et al., Induction of cytotoxic T cell responses and tumor immunity against unrelated tumors using telomerase reverse transcriptase RNA transfected dendritic cells. Nat Med. Sep. 2000;6(9):1011-1017.

Nakatsura et al., Cellular and humoral immune responses to a human pancreatic cancer antigen, coactosin-like protein, originally defined by the SEREX method. Eur J Immunol. Mar. 2002;32(3):826-836.

(56) References Cited

OTHER PUBLICATIONS

Nakatsura et al., Glypican-3, overexpressed specifically in human hepatocellular carcinoma, is a novel tumor marker. Biochem Biophys Res Commun. Jun. 20, 2003;306(1):16-25.

Nakatsura et al., Identification of Glypican-3 as a Novel Tumor Marker for Melanoma. Clin Cancer Res. Oct. 1, 2004;10(19):6612-6621.

Nelson and Griswold, A computer program for calculating antibody affinity constants. Comput Methods Programs Biomed. Jul.-Aug. 1988;27(1):65-68.

Neumann et al., Identification of an HLA-DR-restricted peptide epitope with a promiscuous binding pattern derived from the cancer testis antigen HOM-MEL-40/SSX2. Int J Cancer. Nov. 20, 2004;112(4):661-668.

Nicoletto et al., BRCA-1 and BRCA-2 mutations as prognostic factors in clinical practice and genetic counselling. Cancer Treat Rev. Oct. 2001;27(5):295-304.

Oberste et al., Evidence for Frequent Recombination within Species Human Enterovirus B Based on Complete Genomic Sequences of All Thirty-Seven Serotypes. J Virol. Jan. 2004;78(2):855-867.

Oberthuer et al., The Tumor-Associated Antigen Prame is Universally Expressed in High-Stage Neuroblastoma and Associated with Poor Outcome. Clin Cancer Res. Jul. 1, 2004;10(13):4307-4313.

Ogunniyi et al., c-di-GMP is an Effective Immunomodulator and Vaccine Adjuvant Against Pneumococcal Infection. Vaccine. Aug. 26, 2008;26(36):4676-4685.

Oliveira-Ferreira and Daniel-Ribeiro, Protective CD8+ T Cell Responses against the Pre-erythrocytic Stages of Malaria Parasites: an Overview. Mem Inst Oswaldo Cruz. Feb. 2001;96(2):221-227.

O'Riordan et al., Innate recognition of bacteria by a macrophage cytosolic surveillance pathway. Proc Natl Acad Sci U S A. Oct. 15, 2002;99(21):13861-13866.

Orvell et al., Antigenic relationships between six genotypes of the small hydrophobic protein gene of mumps virus. J Gen Virol. Oct. 2002;83(Pt 10):2489-2496.

Otte et al., MAGE-A Gene Expression Pattern in Primary Breast Cancer. Cancer Res. Sep. 15, 2001;61(18):6682-6687.

Ouyang et al., Structural Analysis of the STING Adaptor Protein Reveals a Hydrophobic Dimer Interface and Mode of Cyclic di-GMP Binding. Immunity. Jun. 29, 2012;36(6):1073-1086.

Oyston and Quarry, Tularemia vaccine: past, present and future. Antonie Van Leeuwenhoek. May 2005;87(4):277-281.

Padilla et al., Imaging of the varicella zoster virion in the viral highways: Comparison with herpes simplex viruses 1 and 2, cytomegalovirus, pseudorabies virus, and human herpes viruses 6 and 7. J Med Virol. 2003;70 Suppl 1:S103-S110.

Patel et al., Development of a simple restriction fragment length polymorphism assay for subtyping of coxsackie B viruses. J Virol Methods. Sep. 15, 2004;120(2):167-172.

Peh et al., Frequent presence of subtype A virus in Epstein-Barr virus-associated malignancies. Pathology. Oct. 2002;34(5):446-450.

Pham et al., Exploiting cross-priming to generate protective CD8 T-cell immunity rapidly. Proc Natl Acad Sci U S A. Jul. 6, 2010;107(27):12198-12203.

Pisarev et al., Full-length dominant-negative survivin for cancer immunotherapy. Clin Cancer Res. Dec. 15, 2003;9(17):6523-6533.

Porsch-Ozcurumez et al., Comparison of Enzyme-Linked Immunosorbent Assay, Western Blotting, Microagglutination, Indirect Immunofluorescence Assay, and Flow Cytometry for Serological Diagnosis of Tularemia. Clin Diagn Lab Immunol. Nov. 2004;11(6):1008-1015.

Rappuoli et al., Vaccines for the twenty-first century society. Nat Rev Immunol. Nov. 4, 2011;11(12):865-872.

Reed et al., New horizons in adjuvants for vaccine development. Trends Immunol. Jan. 2009;30(1):23-32.

Renkvist et al., A listing of human tumor antigens recognized by T cells. Cancer Immunol Immunother. Mar. 2001;50(1):3-15.

Zimmerman et al., Expression of annexin II in conventional renal cell carcinoma is correlated with Fuhrman grade and clinical outcome. Virchows Arch. Oct. 2004;445(4):368-374.

Ziyaeyan et al., The Seroprevalence of Parvovirus BI9 Infection among To-Be-Married Girls, Pregnant Women, and Their Neonates in Shi raz, Iran. Jpn J Infect Dis. Apr. 2005;58(2):95-97.

International Search Report and Written Opinion issued in PCT/US2014/038525 dated Sep. 9, 2014.

International Search Report and Written Opinion issued in PCT/US2014/038526 dated Sep. 19, 2014.

Reynolds et al., HLA-Independent Heterogeneity of CD8+ T Cell Responses to MAGE-3, Melan-A/MART-1, gp100, Tyrosinase, MC1R, and TRP-2 in Vaccine-Treated Melanoma Patients. J Immunol. Dec. 15, 1998;161(12):6970-6976.

Rezig et al., Molecular Characterization of Coxsackievirus B5 Isolates. J Med Virol. Feb. 2004;72(2):268-274.

Ries et al., Investigation of the expression of melanoma antigen-encoding genes (MAGE-A1 to -A6) in oral squamous cell carcinomas to determine potential targets for gene-based cancer immunotherapy. Int J Oncol. Mar. 2005;26(3):817-824.

Roden and Wu, Preventative and therapeutic vaccines for cervical cancer. Expert Rev Vaccines. Aug. 2003;2(4):495-516.

Roner et al., Identification of signals required for the insertion of heterologous genome segments into the reovirus genome. Proc Natl Acad Sci U S A. Dec. 19, 1995;92(26):12362-12366.

Ross et al., The Cyclic Diguanylic Acid Regulatory System of Cellulose Synthesis in Acetobacter xylinum. Chemical synthesis and biological activity of cyclic nucleotide dimer, trimer, and phosphothioate derivatives. J Biol Chem. Nov. 5, 1990;265(31):18933-18943.

Salazar-Onfray et al., Synthetic peptides derived from the melanocyte-stimulating hormone receptor MC1R can stimulate HLA-A2-restricted cytotoxic T lymphocytes that recognize naturally processed peptides on human melanoma cells. Cancer Res. Oct. 1, 1997;57(19):4348-4355.

Santin et al., The serine protease stratum corneum chymotryptic enzyme (kallikrein 7) is highly overexpressed in squamous cervical cancer cells. Gynecol Oncol. Aug. 2004;94(2):283-288.

Sarcevic et al., Expression of Cancer/Testis Tumor Associated Antigens in Cervical Squamous Cell Carcinoma Oncology. 2003;64(4):443-449.

Sarobe et al., Carcinoembryonic Antigen as a Target to Induce Anti-Tumor Immune Responses. Curr Cancer Drug Targets. Aug. 2004;4(5):443-454.

Sasaki et al., SAGE mRNA expression in advanced-stage lung cancers. Eur J Surg Oncol. Dec. 2003;29(10):900-903.

Sasatomi et al., Expression of tumor rejection antigens in colorectal carcinomas. Cancer. Mar. 15, 2002;94(6):1636-1641.

Sauer et al., The N-Ethyl-N-Nitrosourea-Induced Goldenticket Mouse Mutant Reveals an Essential Function of Sting in the In Vivo Interferon Response to Listeria monocytogenes and Cyclic Dinucleotides. Infect Immun. Feb. 2011;79(2):688-694.

Scanlan et al., Antigens recognized by autologous antibody in patients with renal-cell carcinoma. Int J Cancer. Nov. 12, 1999;83(4):456-464.

Scanlan et al., Cancer-related serological recognition of human colon cancer: identification of potential diagnostic and immunotherapeutic targets. Cancer Res. Jul. 15, 2002;62(14):4041-4047.

Scanlan et al., Expression of cancer-testis antigens in lung cancer: definition of bromodomain testis-specific gene (BRDT) as a new CT gene, CT9. Cancer Lett. Mar. 31, 2000;150(2):155-164.

Scanlan et al., Humoral immunity to human breast cancer: antigen definition and quantitative analysis of mRNA expression. Cancer Immun. Mar. 30, 2001;1:4.

Scanlan et al., The cancer/testis genes: review, standardization, and commentary. Cancer Immun. Jan. 23, 2004;4:1.

Scarcella et al., Expression of MAGE and GAGE in high-grade brain tumors: a potential target for specific immunotherapy and diagnostic markers. Clin Cancer Res. Feb. 1999;5(2):335-341.

Schmidt et al., Memory CD8 T cell responses exceeding a large but definable threshold provide long-term immunity to malaria. Proc Natl Acad Sci U S A. Sep. 16, 2008;105(37):14017-14022.

(56) References Cited

OTHER PUBLICATIONS

Schmittgen et al., Expression of prostate specific membrane antigen and three alternatively spliced variants of PSMA in prostate cancer patients. Int J Cancer. Nov. 1, 2003;107(2):323-329.
Schwartz et al., Hyperinduction of Host Beta Interferon by a Listeria monocytogenes Strain Naturally Overexpressing the Multidrug Efflux Pump MdrT. Infect Immun. Apr. 2012;80(4):1537-1545.
Schwartz et al., Novel targeted and immunotherapeutic strategies in chronic myeloid leukemia. Semin Hematol. Jan. 2003;40(1):87-96.
Seder et al., T-cell quality in memory and protection: implications for vaccine design. Nat Rev Immunol. Apr. 2008;8(4):247-258.
Sepehr et al., Distinct pattern of TP53 mutations in squamous cell carcinoma of the esophagus in Iran. Oncogene. Nov. 1, 2001;20(50):7368-7374.
Shanahan et al., Differential analog binding by two classes of c-di-GMP riboswitches. J Am Chem Soc. Oct. 5, 2011;133(39):15578-15592.
Shigemasa et al., Expression of the protease inhibitor antileukoprotease and the serine protease stratum corneum chymotryptic enzyme (SCCE) is coordinated in ovarian tumors. Int J Gynecol Cancer. Nov.-Dec. 2001;11(6):454-461.
Shirakawa et al., A Cox-2 Promoter-Based Replication-Selective Adenoviral Vector to Target the Cox-2-Expressing Human Bladder Cancer Cells. Clin Cancer Res. Jul. 1, 2004;10(13):4342-4348.
Shirasawa et al., Receptor for advanced glycation end-products is a marker of type I lung alveolar cells. Genes Cells. Feb. 2004;9(2):165-174.
Shivapurkar et al., Presence of Simian Virus 40 DNA Sequences in Human Lymphoid and Hematopoietic Malignancies and Their Relationship to Aberrant Promoter Methylation of Multiple Genes. Cancer Res. Jun. 1, 2004;64(11):3757-3760.
Shu et al., Structure of STING bound to c-di-GMP Reveals the Mechanism of Cyclic Dinucleotide Recognition by the Immune System. Nat Struct Mol Biol. Jun. 24, 2012;19(7):722-724.
Siegel et al., Induction of antitumour immunity using survivin peptide-pulsed dendritic cells in a murine lymphoma model. Br J Haematol. Sep. 2003;122(6):911-914.
Simon et al., Cervical response to vaccination against HPV16 E7 in case of severe dysplasia. Eur J Obstet Gynecol Reprod Biol. Aug. 15, 2003;109(2):219-223.
Singh et al., Avian influenza viral nucleocapsid and hemagglutinin proteins induce chicken CD8+ memory T lymphocytes. Virology 2010;399:231-238.
Singh et al., Non-replicating adenovirus vectors expressing avian influenza virus hemagglutinin and nucleocapsid proteins induce chicken specific effector, memory and effector memory CD8(+) T lymphocytes. Virology. Sep. 15, 2010;405(1):62-69.
Sjolander et al., Serological divergence of Dobrava and Saaremaa hantaviruses: evidence for two distinct serotypes. Epidemiol Infect. Feb. 2002;128(1):99-103.
Skoberne et al., KBMA Listeria monocytogenes is an effective vector for DC-mediated induction of antitumor immunity. J Clin Invest. Dec. 2008;118(12):3990-4001.
Slager et al., Identification of multiple HLA-DR-restricted epitopes of the tumor-associated antigen CAMEL by CD4+ Th1/Th2 lymphocytes. J Immunol. Apr. 15, 2004;172(8):5095-5102.
Slager et al., Induction of CAMEL/NY-ESO-ORF2-specific CD8+ T cells upon stimulation with dendritic cells infected with a modified Ad5 vector expressing a chimeric Ad5/35 fiber. Cancer Gene Ther. Mar. 2004;11(3):227-236.
Small et al., Immunotherapy of Hormone-Refractory Prostate Cancer With Antigen-Loaded Dendritic Cells. J Clin Oncol. Dec. 1, 2000;18(23):3894-3903.
Smith et al., Neutralization of HIV-1 Subtypes: Implications for Vaccine Formulations. J Med Virol. Nov. 1998;56(3):264-268.
Smits et al., Phylogenetic and Evolutionary Relationships among Torovirus Field Variants: Evidence for Multiple Intertypic Recombination Events. J Virol. Sep. 2003;77(17):9567-9577.
Sofia et al., Nucleoside, Nucleotide, and Non-Nucleoside Inhibitors of Hepatitis C Virus NS5B RNA-Dependent RNA-Polymerase. J. Med Chem. Mar. 22, 2012;55(6):2481-2531.
Sofia, Nucleotide Prodrugs for HCV Therapy. Antivir Chem Chemother. Aug. 23, 2011;22(1):23-49.
Stams et al., Expression Levels of TEL, AML1, and the Fusion ProductsTEL-AML1 and AML1-TEL versus Drug Sensitivity and Clinical Outcome in t(12;21)-Positive Pediatric Acute Lymphoblastic Leukemia. Clin Cancer Res. Apr. 15, 2005;11(8):2974-2980.
Steffens et al., Immunohistochemical analysis of tumor antigen saturation following injection of monoclonal antibody G250. Anticancer Res. Mar.-Apr. 1999;19(2A):1197-1200.
Stirnadel et al., Assessment of different sources of variation in the antibody responses to specific malaria antigens in children in Papua New Guinea. Int J Epidemiol. Jun. 2000;29(3):579-586.
Stolier et al., Initial experience with surgical treatment planning in the newly diagnosed breast cancer patient at high risk for BRCA-1 or BRCA-2 mutation. Breast J. Nov.-Dec. 2004;10(6):475-480.
Studahl et al., Herpesvirus DNA Detection in Cerebral Spinal Fluid: Differences in Clinical Presentation between Alpha-, Beta-, and Gamma-Herpesviruses. Scand J Infect Dis. 2000;32(3):237-248.
Sun et al., Cyclic GMP-AMP Synthase is a Cytosolic DNA Sensor That Activates the Type I Interferon Pathway. Science. Feb. 15, 2013;339(6121):786-791.
Coler et al. Development and Characterization of Synthetic Glucopyranosyl Lipid Adjuvant System as a Vaccine Adjuvant. PLoS One. Jan. 26, 2011;6(1):e16333.
Coughlin et al., Orally Bioavailable Anti-HBV Dinucleotide Acyloxyalkyl Prodrugs. Bioorg Med Chem Lett. Mar. 1, 2010;20(5):1783-1786.
Creighton et al., Mechanisms and catalysts of disulfide bond formation in proteins. Trends Biotechnol. Jan. 1995;13(1):18-23.
Crimmins et al., Listeria monocytogenes multidrug resistance transporters activate a cytosolic surveillance pathway of innate immunity. Proc Natl Acad Sci U S A. Jul. 22, 2008;105(29):10191-10196.
Dalerba et al., MAGE, BAGE and GAGE gene expression in human rhabdomyosarcomas. Int J Cancer. Jul. 1, 2001;93(1):85-90.
Damasus-Awatai and Freeman-Wang, Human papilloma virus and cervical screening. Curr Opin Obstet Gynecol. Dec. 2003;15(6):473-477.
Das et al., Evaluation of a Western Equine Encephalitis recombinant E1 protein for protective immunity and diagnostics. Antiviral Res. Nov. 2004;64(2):85-92.
Davies et al., Characterisation of a recombinant Fv fragment of anti-MUC1 antibody HMFG1. Cancer Lett. Jul. 29, 1994;82(2):179-184.
Davies et al., Coordinated Regulation of Accessory Genetic Elements Produces Cyclic Di-Nucleotides for V. cholerae Virulence. Cell. Apr. 13, 2012;149(2):358-370.
De Backer et al., Characterization of the GAGE Genes that are Expressed in Various Human Cancers and in Normal Testis. Cancer Res. Jul. 1, 1999;59(13):3157-3165.
De Villiers et al., Classification of papillomaviruses. Virology. Jun. 20, 2004;324(1):17-24.
Demidenko and Blagosklonny, Flavopiridol Induces p53 via Initial Inhibition of Mdm2 and P21 and, Independently of p53, Sensitizes Apoptosis-Reluctant Cells to Tumor Necrosis Factor. Cancer Res. May 15, 2004;64(10):3653-3660.
Desmet and Ishii, Nucleic acid sensing at the interface between innate and adaptive immunity in vaccination. Nat Rev Immunol. Jun. 22, 2012;12(7):479-491.
Dessureault et al., A phase-I Trial Using a Universal GM-CSF-producing and CD40L-expressing Bystander Cell Line (GM.CD40L) in the Formulation of Autologous Tumor Cell-based Vaccines for Cancer Patients with Stage IV disease. Ann Surg Oncol. Feb. 2007;14(2):869-884.
Diner et al., The Innate Immune DNA Sensor cGAS Produces a Noncanonical Cyclic Dinucleotide that Activates Human STING. Cell Rep. May 30, 2013;3(5):1355-1361.
Disis and Cheever, HER-2/Neu Protein: A Target for Antigen-Specific Immunotherapy of Human Cancer. Adv. Cancer Res. 1997;71:343-371.

(56) References Cited

OTHER PUBLICATIONS

Disis et al., Humoral Epitope-Spreading Following Immunization with a HER-2/neu Peptide Based Vaccine in Cancer Patients. J Clin Immunol. Sep. 2004;24(5):571-578.

Dosaka-Akita et al., Expression of N-Acetylglucosaminyltransferase V is Associated with Prognosis and Histology in Non-Small Cell Lung Cancers. Clin Cancer Res. Mar. 1, 2004;10(5):1773-1779.

Dubensky and Reed, Adjuvants for cancer vaccines. Semin Immunol. Jun. 2010;22(3):155-161.

Duxbury et al., CEACAM6 as a novel target for indirect type 1 immunotoxin-based therapy in pancreatic adenocarcinoma. Biochem Biophys Res Commun. May 7, 2004;317(3):837-843.

Eager and Nemunaitis, GM-CSF Gene-Transduced Tumor Vaccines. Mol Ther. Jul. 2005;12(1):18-27.

Ebensen et al., Bis-(3',5')-cyclic dimeric adenosine monophosphate: Strong Th1/Th2/Th17 promoting mucosal adjuvant. Vaccine. Jul. 18, 2011;29(32):5210-5220.

Ebensen et al., The bacterial second messenger cyclic diGMP exhibits potent adjuvant properties. Vaccine. Feb. 9, 2007;25(8):1464-1469.

Ebensen et al., The Bacterial Second Messenger cdiGMP Exhibits Promising Activity as a Mucosal Adjuvant. Clin Vaccine Immunol. Aug. 2007;14(8):952-958.

Einstein et al., Comparison of the immunogenicity and safety of Cervarix and Gardasil human papillomavirus (HPV) cervical cancer vaccines in healthy women aged 18-45 years. Hum Vaccin. Oct. 2009;5(10):705-719.

Elgh et al., Serological Diagnosis of Hantavirus Infections by an Enzyme-Linked Immunosorbent Assay Based on Detection of Immunoglobulin G and M Responses to Recombinant Nucleocapsid Proteins of Five Viral Serotypes. J Clin Microbiol. May 1997;35(5):1122-1130.

Engels et al., Serologic Evidence for Exposure to Simian Virus 40 in North American Zoo Workers. J Infect Dis. Dec. 15, 2004;190(12):2065-2069.

Enjoji et al., RCAS1, a Useful Serum Marker to Predict the Recurrence of Cancer: Two Cases of Cholangiocarcinoma and Pancreatic Cancer. Dig Dis Sci. Oct. 2004;49(10):1654-1656.

Ericson et al., Expression of Cyclin-Dependent Kinase 6, but not Cyclin-Dependent Kinase 4, Alters Morphology of Cultured Mouse Astrocytes. Mol Cancer Res. Jul. 2003;1(9):654-664.

Estrada-Franco et al., Venezuelan Equine Encephalitis Virus, Southern Mexico. Emerg Infect Dis. Dec. 2004;10(12):2113-2121.

Fang et al., Expression of Dnmt1, demethylase, MeCP2 and methylation of tumor-related genes in human gastric cancer. World J Gastroenterol. Dec. 1, 2004;10(23):3394-3398.

Faure et al., Inducible Hsp70 as Target of Anticancer Immunotherapy: Identification of HLA-A*0201-Restricted Epitopes. Int J Cancer. Mar. 1, 2004;108(6):863-870.

Fleishhauer et al., The DAM Gene Family Encodes a New Group of Tumor-specific Antigens Recognized by Human Leukocyte Antigen AI-restricted Cytotoxic T Lymphocytes. Cancer Res. Jul. 15, 1998;58(14):2969-2972.

Fong et al., Altered peptide ligand vaccination with Flt3 ligand expanded dendritic cells for tumor immunotherapy. Proc Natl Acad Sci U S A. Jul. 17, 2001;98(15):8809-8814.

Fuessel et al., Multiple tumor marker analyses (PSA, hK2, PSCA, trp-p8) in primary prostate cancers using quantitative RT-PCR. Int J Oncol. Jul. 2003;23(1):221-228.

Fujii et al., The VesiVax system: a method for rapid vaccine development. Front Biosci. Jan. 1, 2008;13:1968-1980.

Gaffney et al., One-Flask Syntheses of c-di-GMP and the [Rp,Rp] and [Rp,Sp] Thiophosphate Analogues. Org Lett. Jul. 16, 2010;12(14):3269-3271.

Gambus et al., Epitope mapping of a mouse monoclonal anti-MUC2 antibody suggests the existence of an immunodominant region in the COOH terminus of the MUC2 tandem-repeat sequence. Int J Cancer. Jan. 3, 1995;60(1):146-148.

Gao et al., Cyclic [G(20,50)pA(30,50)p] is the Metazoan Second Messenger Produced by DNA-Activated Cyclic GMP-AMP Synthase. Cell, May 23, 2013; 153(5):1094-1107.

Gao et al., Structure-Function Analysis of STING Activation by c[G(2',5')pA(3',5')p] and Targeting by Antiviral DMXAA. Cell. Aug. 15, 2013;154(4):748-762.

Geisbert and Jahrling, Differentiation of filoviruses by electron microscopy. Virus Res. Dec. 1995;39(2-3):129-150.

Ghazizadeh et al., Role of cdk4, p16INK4, and Rb Expression in the Prognosis of Bronchioloalveolar Carcinomas. Respiration. Jan.-Feb. 2005;72(1):68-73.

Gilliam et al., A phase II study of G17DT in gastric carcinoma. Eur J Surg Oncol. Jun. 2004;30(5):536-543.

Gonzalez et al., A comparative sequence analysis to revise the current taxonomy of the family Coronaviridae. Arch Virol. Nov. 2003;148(11):2207-2235.

Good et al., Development and regulation of cell-mediated immune responses to the blood stages of malaria: implications for vaccine research. Annu Rev Immunol. 2005;23:69-99.

Good et al., The immunological challenge to developing a vaccine to the blood stages of malaria parasites. Immunol Rev. Oct. 2004;201:254-267.

Grajkowski et al., Convenient Synthesis of a Propargylated Cyclic (3'-5') Diguanylic Acid and its "Click" Conjugation to a Biotinylated Azide. Bioconjug Chem. Nov. 17, 2010;21(11):2147-2152.

Grimm et al., Mouse alpha-fetoprotein-specific DNA-based immunotherapy of hepatocellular carcinoma leads to tumor regression in mice. Gastroenterology. Oct. 2000;119(4):1104-1112.

Groh et al., Efficient cross-priming of tumor antigen-specific T cells by dendritic cells sensitized with diverse anti-MICA opsonized tumor cells. Proc Natl Acad Sci USA. May 3, 2005;102(18):6461-6466.

Gueguen et al., An Antigen Recognized by Autologous CTLs on a Human Bladder Carcinoma. J Immunol. Jun. 15, 1998;160(12):6188-6194.

Shanahan et al., "Differential analog binding by two classes of c-di-GMP riboswitches", J Am Chem Soc. Oct. 5, 2011; 133(39): 15578-15592. doi:10.1021/ja204650q.

Ablasser et al., cGAS produces 2'-5'-linked cdn second messenger that activates STING. Nature. Jun. 20, 2013;498(7454):380-384.

Antonarakis and Drake, Combining immunological and androgen-directed approaches: an emerging concept in prostate cancer immunotherapy. Curr Opin Oncol. May 2012;24(3):258-265.

Ausmees et al., Genetic data indicate that proteins containing the GGDEF domain possess diguanylate cyclase activity. FEMS Microbiol Lett. Oct. 16, 2001;204(1):163-167.

Bahjat et al., Activation of Immature Hepatic NK Cells as Immunotherapy for Liver Metastatic Disease. J Immunol. Dec. 1, 2007;179(11):7376-7384.

Barker et al., STING-Dependent Recognition of Cyclic di-AMP Mediates Type I Interferon Responses during Chlamydia trachomatis Infection. MBio. Apr. 30, 2013;4(3):e00018-e00013.

Blankenstein et al., The determinants of tumour immunogenicity. Nat Rev Cancer. Mar. 1, 2012;12(4):307-313.

Bowie et al., Innate Sensing of bacterial cdns: more than just STING. Nat Immunol. Dec. 2012;13(12):1137-1139.

Brahmer et al., Phase I Study of Single-Agent Anti-Programmed Death-1 (MDX-1106) in Refractory Solid Tumors: Safety, Clinical Activity, Pharmacodynamics, and Immunologic Correlates. J Clin Oncol. Jul. 1, 2010;28(19):3167-3175.

Brockstedt et al., Listeria-based cancer vaccines that segregate immunogenicity from toxicity. Proc Natl Acad Sci U S A. Sep. 21, 2004;101(38):13832-13837.

Chan et al., Structural basis of activity and allosteric control of diguanylate cyclase. Proc Natl Acad Sci U S A. Dec. 7, 2004;101(49):17084-17089.

Chen et al., The potential of 3',5'-cyclic diguanylic acid (c-di-GMP) as an effective vaccine adjuvant. Vaccine. Apr. 19, 2010;28(18):3080-3085.

Civril et al., Structural mechanism of cytosolic DNA sensing by cGAS. Nature. Jun. 20, 2013;498(7454):332-337.

(56) References Cited

OTHER PUBLICATIONS

Conlon et al., Mouse, but not Human STING, Binds and Signals in Response to the Vascular Disrupting Agent 5,6-Dimethylxanthenone-4-Acetic Acid. J Immunol. May 15, 2013;190(10):5216-5225.

Crittenden et al., Expression of Inflammatory Chemokines Combined with Local Tumor Destruction Enhances Tumor Regression and Long-term Immunity. Cancer Res. Sep. 1, 2003;63(17):5505-5512.

Curran and Allison, Tumor Vaccines Expressing Flt3 Ligand Synerigize with CTLA-4 Blockade to Reject Preimplanted Tumors. Cancer Res. Oct. 1, 2009;69(19):7747-7735.

Dalby et al., Advanced transfection with Lipofectamine 2000 reagent: primary neurons, siRNA, and high-throughput applications. Methods. Jun. 2004;33(2):95-103.

De Grujil et al., Whole-cell cancer vaccination: from autologous to allogeneic tumor- and dendritic cell-based vaccines. Cancer Immunol Immunother. Oct. 2008;57(10):1569-1577.

Di Lorenzo et al., Immunotherapy for the treatment of prostate cancer. Nat Rev Clin Oncol. May 24, 2011;8(9):551-561.

Drake et al., Androgen ablation mitigates tolerance to a prostate/prostate cancer-restricted antigen. Cancer Cell. Mar. 2005;7(3):239-249.

Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-3543.

Driessens et al., Highly Successful Therapeutic Vaccinations Combining Factor Dendritic Cells and Tumo Cells Secreting Granulocyte Macrophage Colony-stimulating Factor. Cancer Res. Nov. 15, 2004;64(22):8435-8442.

Dubensky et al., Abstract 4573: A novel tumor vaccine with cyclic dinucleotides—can induce potent anti-tumor responses in vivo. Cancer Res. Apr. 15, 2013;73(8 Suppl):4573-4573.

Dubensky et al., Rationale, progress, and development of vaccines utilizing STING-activating cyclic dinucleotide adjuvants. Ther Adv Vaccines. Nov. 2013;1(4):131-143.

Ettmayer et al., Lessons Learned from Marketed and Investigational Prodrugs. J Med Chem. May 6, 2004;47(10):2393-2404.

Ertem and Ferris, Synthesis of RNA oligomers on heterogeneous templates. Nature. Jan. 18, 1996;379(6562):238-240.

Fasso et al., SPAS-1 (stimulator of prostatic adenocarcinoma-specific T cells)/SH3GLB2: A prostate tumor antigen identified by CTLA-4 blockade. Proc Natl Acad Sci U S A. Mar. 4, 2008;105(9):3509-3514.

Gao et al., GM-CSF-surface-modified B16.F10 melanoma cell vaccine. Vaccine. Jun. 19, 2006;24(25):5265-5268.

Goldberg et al., Role of PD-1 and its ligand, B7-H1, in early fate decisions of CD8 T cells. Blood. Jul. 1, 2007;110(1):186-192.

Gulley et al., Immunologic and Prognostic Factors Associated with Overall Survival Employing a Poxviral-based PSA Vaccine in Metastatic Castrate-resistant Prostate Cancer. Cancer Immunol Immunother. May 2010;59(5):663-674.

Hernandez et al., Novel Kidney Cancer Immunotherapy Based on the Granulocyte-Macrophage Colony-stimulating Factor and Carbonic Anhydrase IX Fusion Gene. Clin Cancer Res. May 2003;9(5):1906-1916.

Hodi et al., Improved Survival with Ipilimumab in Patients with Metastatic Melanoma. N Engl J Med. Aug. 19, 2010;363(8):711-723.

Huang et al., The structural basis for the sensing and binding of CDG by STING. Nat Struct Mol Biol. Jun. 24, 2012;19(7):728-730.

Hurwitz et al., The TRAMP Mouse as a Model for Prostate Cancer. Curr Protoc Immunol. Nov. 2001;Chapter 20:Unit 20.5.

Ishikawa and Barber, The STING pathway and regulation of innate immune signaling in response to DNA pathogens. Cell Mol Life Sci. Apr. 2011;68(7):1157-1165.

Jemal et al., Cancer statistics, 2010. CA Cancer J Clin. Sep.-Oct. 2010;60(5):277-300.

Kantoff et al., Sipuleucel-T Immunotherapy for Castration-Resistant Prostate Cancer. N Engl J Med. Jul. 2, 2010;363(5):411-422.

Kantoff et al., Overall Survival Analysis of a Phase II Randomized Controlled Trial of a Poxviral-Based PSA-Targeted Immunotherapy in Metastatic Castration-Resistant Prostate Cancer. J Clin Oncol. Mar. 1, 2010;28(7):1099-1105.

Krishnamachari et al., Nanoparticle Delivery Systems in Cancer Vaccines. Pharm Res 2011;28:215-236.

Lam et al, Adenovirus Detection by the cGAS/STING/TBK1 DNA Sensing Cascade. J Virol. Jan. 2014;88(2):974-981.

Le et al., A Live-Attenuated Listeria Vaccine (ANZ-100) and a Live-Attenuated Listeria Vaccine Expressing Mesothelin (CRS-207) for Advanced Cancers: Phase I Studies of Safety and Immune Induction. Clin Cancer Res. Feb. 1, 2012;18(3):858-868.

Le et al., Cellular Vaccine Approaches. Cancer J. Jul.-Aug. 2010;16(4):304-10.

Li et al, Cyclic GMP-AMP Synthase is Activated by Double-Stranded DNA-Induced Oligomerization. Immunity. Dec. 12, 2013;39(6):1019-1031.

Libanova, Cyclic di-nucleotides: new era for small molecules as adjuvants. Microb Biotechnol. Mar. 2012;5(2):168-176.

Luo et al, Selective binding of 2'-F-c-di-GMP to Ct-E88 and Cb-E43, new class I riboswitches from Clostridium tetani and Clostridium botulinum respectively. Mol Biosyst. Jun. 2013;9(6):1535-1539.

Lutz et al., A Lethally Irradiated Allogeneic Granulocyte-Macrophage Colony Stimulating Factor-Secreting Tumor Vaccine for Pancreatic Adenocarcinoma: A Phase II Trial of Safety, Efficacy, and Immune Activation. Ann Surg. Feb. 2011;253(2):328-335.

Mathew et al, Cytosolic delivery of antisense oligonucleotides by listeriolysin O-containing liposomes. Gene Ther. Jul. 2003;10(13):1105-1115.

Mellman et al., Cancer immunotherapy comes of age. Nature. Dec. 21, 2011;480(7378):480-489.

Miyabe et al., A new adjuvant delivery system 'cyclic-di-GMP/YSK05 liposome' for cancer immunotherapy. J Control Release. Jun. 28, 2014;184:20-27 (author's version).

Olson et al., Liposomal gD Ectodomain (gD1-306) Vaccine Protects Against HSV2 Genital or Rectal Infection of Female and Male Mice. Vaccine. Dec. 11, 2009;28(2):548-560.

\* cited by examiner $X_1 = X_2 = O^-$, $X_1 = X_2 = S^-$,

Or $X_1 = O^-, X_2 = S^-$

10a

11a

10b

11b

10c

11c

10A.

10B.

11A.

11B.

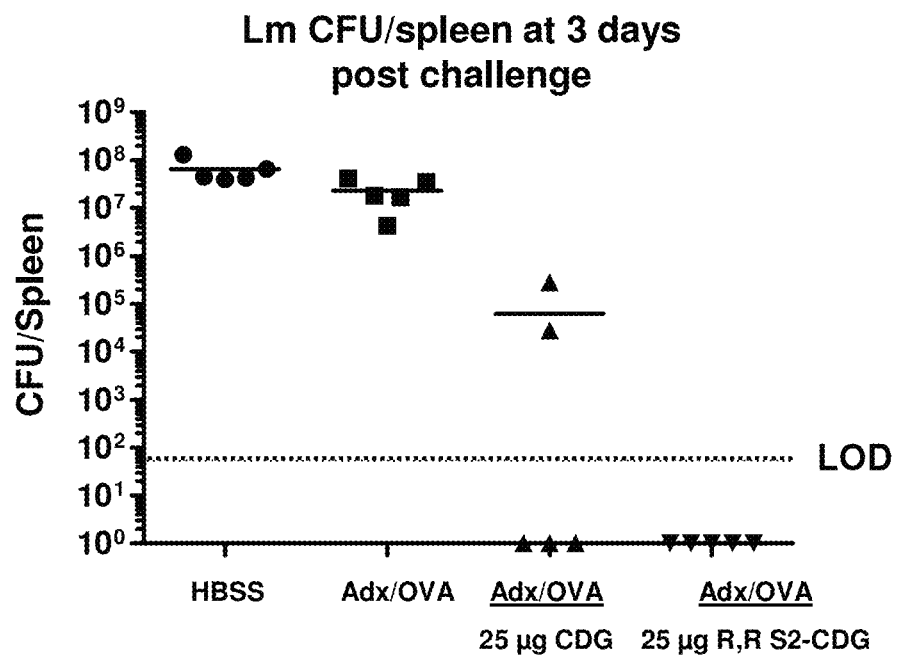

ures they are refractory to traditional therapeutic approaches.

COMPOSITIONS COMPRISING CYCLIC PURINE DINUCLEOTIDES HAVING DEFINED STEREOCHEMISTRIES AND METHODS FOR THEIR PREPARATION AND USE

The present application claims priority to U.S. Provisional Application 61/737,006, filed Dec. 13, 2012, and to U.S. Provisional Application 61/790,514, filed Mar. 15, 2013, each of which is hereby incorporated in its entirety including all tables, figures, and claims.

BACKGROUND OF THE INVENTION

The following discussion of the background of the invention is merely provided to aid the reader in understanding the invention and is not admitted to describe or constitute prior art to the present invention.

The human immune system may generally be divided into two arms, referred to as "innate immunity" and "adaptive immunity." The innate arm of the immune system is predominantly responsible for an initial inflammatory response via a number of soluble factors, including the complement system and the chemokine/cytokine system; and a number of specialized cell types including mast cells, macrophages, dendritic cells (DCs), and natural killer cells. In contrast, the adaptive immune arm involves a delayed and a longer lasting antibody response together with CD8+ and CD4+ T cell responses that play a critical role in immunological memory against an antigen. A third arm of the immune system may be identified as involving γδ T cells and T cells with limited T cell receptor repertoires such as NKT cells and MAIT cells.

For an effective immune response to an antigen, antigen presenting cells (APCs) must process and display the antigen in a proper MHC context to a T cell, which then will result in either T cell stimulation of cytotoxic and helper T cells. Following antigen presentation successful interaction of co-stimulatory molecules on both APCs and T cells must occur or activation will be aborted. GM-CSF and IL-12 serve as effective pro-inflammatory molecules in many tumor models. For example, GM-CSF induces myeloid precursor cells to proliferate and differentiate into dendritic cells (DCs) although additional signals are necessary to activate their maturation to effective antigen-presenting cells necessary for activation of T cells. Barriers to effective immune therapies include tolerance to the targeted antigen that can limit induction of cytotoxic CD8 T cells of appropriate magnitude and function, poor trafficking of the generated T cells to sites of malignant cells, and poor persistence of the induced T cell response.

DCs that phagocytose tumor-cell debris process the material for major histocompatibility complex (MHC) presentation, upregulate expression of costimulatory molecules, and migrate to regional lymph nodes to stimulate tumor-specific lymphocytes. This pathway results in the proliferation and activation of CD4+ and CD8+ T cells that react to tumor-associated antigens. Indeed, such cells can be detected frequently in the blood, lymphoid tissues, and malignant lesions of patients.

New insights into the mechanisms underlying immune-evasion, together with combination treatment regimens that potentiate the potency of therapeutic vaccination—either directly or indirectly—through combination with immune checkpoint inhibitors or other therapies, have served as a basis for the development of vaccines that induce effective antitumor immunity. The CDNs cyclic-di-AMP (produced by *Listeria monocytogenes*) and its analog cyclic-di-GMP (produced by *Legionella pneumophila*) are recognized by the host cell as a PAMP (Pathogen Associated Molecular Pattern), which bind to the PRR (Pathogen Recognition Receptor) known as STING. STING is an adaptor protein in the cytoplasm of host mammalian cells which activates the TANK binding kinase (TBK1)—IRF3 signaling axis, resulting in the induction of IFN-β and other IRF-3 dependent gene products that strongly activate innate immunity. It is now recognized that STING is a component of the host cytosolic surveillance pathway, that senses infection with intracellular pathogens and in response induces the production of IFN-β, leading to the development of an adaptive protective pathogen-specific immune response consisting of both antigen-specific CD4 and CD8 T cells as well as pathogen-specific antibodies. Examples of cyclic purine dinucleotides are described in some detail in, e.g., U.S. Pat. Nos. 7,709,458 and 7,592,326; WO2007/054279; and Yan et al., Bioorg. Med. Chem Lett. 18: 5631 (2008), each of which is hereby incorporated by reference.

There remains a need for improved compositions and methods for immunologic strategies to treating diseases such as cancer that can be refractory to traditional therapeutic approaches.

SUMMARY OF THE INVENTION

It is an object of the present invention to provide novel and highly active cyclic-di-nucleotide (CDN) immune stimulators that activates DCs via a recently discovered cytoplasmic receptor known as STING (Stimulator of Interferon Genes). In particular, the CDNs of the present invention are provided in the form of a composition comprising one or more cyclic purine dinucleotides that induce STING-dependent TBK1 activation, wherein the cyclic purine dinuclotides present in the composition are substantially pure Rp,Rp or Rp,Sp stereoisomers, and particularly substantially pure Rp,Rp, or RpSp CDN thiophosphate diastereomers.

In a first aspect, the present invention provides a composition comprising one or more cyclic purine dinucleotide, wherein the cyclic purine dinuclotides present in the composition are substantially pure Rp,Rp or Rp,Sp diastereomers, or prodrugs or pharmaceutically acceptable salts thereof. These compositions, which induce STING-dependent TBK1 activation, may comprise one or more pharmaceutically acceptable excipients and may find use as adjuvants as described herein. Particularly preferred are thiophosphate derivatives of cyclic purine dinucleotides as described hereinafter In their role as adjuvants, in certain embodiments the present compositions may be used as adjuvants in a therapeutic or prophylactic strategy employing vaccine(s). Thus, substantially pure Rp,Rp or Rp,Sp diastereomers, or prodrugs or pharmaceutically acceptable salts thereof, may be used together with one or more vaccines selected to stimulate an immune response to one or more predetermined antigens. The substantially pure Rp,Rp or Rp,Sp diastereomers, or prodrugs or pharmaceutically acceptable salts thereof of the present invention may be provided together with, or in addition to, such vaccines.

Such vaccine(s) can comprise inactivated or attenuated bacteria or viruses comprising the antigens of interest, purified antigens, live viral or bacterial delivery vectors recombinantly engineered to express and/or secrete the antigens, antigen presenting cell (APC) vectors comprising cells that are loaded with the antigens or transfected with a composition comprising a nucleic acid encoding the antigens, liposomal antigen delivery vehicles, or naked nucleic acid vectors encoding the antigens. This list is not meant to be limiting. By way of example, such vaccine(s) may also comprise an inactivated tumor cell that expresses and secretes one or more of GM-CSF, CCL20, CCL3, IL-12p70, FLT-3 ligand.

The compositions of the present invention may be administered to individuals in need thereof by a variety of parenteral and nonparenteral routes in formulations containing pharmaceutically acceptable carriers, adjuvants and vehicles. Preferred routes are parenteral, and include but, are not limited to, one or more of subcutaneous, intravenous, intramuscular, intraarterial, intradermal, intrathecal and epidural administrations. Particularly preferred is administration by subcutaneous administration. Preferred pharmaceutical composition are formulated as aqueous or oil-in-water emulsions.

The compositions of the present invention may comprise, or be administered together with, one or more additional pharmaceutically active components such as adjuvants, lipids such as digitonin, liposomes, CTLA-4 and PD-1 pathway Antagonists, PD-1 pathway blocking agents, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), C-type lectin receptors (CLRs), pathogen-associated molecular patterns ("PAMPs"), chemotherapeutic agents, etc.

As described hereinafter, cyclic purine dinuclotides formulated with one or more lipids can exhibit improved properties, including improved dendritic cell activation activity. Thus, the present invention also relates to a composition comprising one or more CDNs and one or more lipids. In certain preferred embodiments, one or more CDNs are formulated with digitonin, a liposomal formulation, and/or an oil-in-water emulsion. A composition according to one of claims 1-5, further comprising one or more of a CTLA-4 antagonist and a TLR-4 agonist.

In preferred embodiments, the one or more thiophposphate cyclic purine dinucleotides comprise a substantially pure Rp,Rp or Rp,Sp thiophposphate diastereomer selected from the group consisting of c-di-AMP thiophposphate, c-di-GMP thiophposphate, c-di-IMP thiophposphate, c-AMP-GMP thiophposphate, c-AMP-IMP thiophposphate, and c-GMP-IMP thiophposphate, or combinations thereof, including prodrugs and pharmaceutically acceptable salts thereof.

In a related aspect, the present invention relates to methods of inducing, stimulating, or adjuvanting an immune response in an individual. These methods comprise administering to the individual a composition comprising one or more cyclic purine dinucleotide, wherein the thiophposphate cyclic purine dinuclotides present in the composition are substantially pure Rp,Rp or Rp,Sp diastereomers, or prodrugs or pharmaceutically acceptable salts thereof to the individual. Preferred routes of administration are parenteral. As noted above, particularly preferred are thiophosphate derivatives of such cyclic purine dinucleotides.

In certain embodiments, the method is a method of cancer treatment. By way of example, the substantially pure Rp,Rp or Rp,Sp diastereomers, or prodrugs or pharmaceutically acceptable salts thereof of the present invention may be provided together with, or in addition to, one or more cancer vaccine compositions that are known in the art. The patient receiving such treatment may be suffering from a cancer selected from the group consisting of a colorectal cancer cell, an aero-digestive squamous cancer, a lung cancer, a brain cancer, a liver cancer, a stomach cancer, a sarcoma, a leukemia, a lymphoma, a multiple myeloma, an ovarian cancer, a uterine cancer, a breast cancer, a melanoma, a prostate cancer, a pancreatic carcinoma, and a renal carcinoma. In other embodiments, the method is a method of inducing, stimulating, or adjuvanting an immune response a pathogen.

In still other related aspects, the present invention relates to methods of inducing STING-dependent TBK1 activation in an individual, comprising administering one or more cyclic purine dinucleotides which bind to STING to the individual, wherein the cyclic purine dinuclotides present in the composition are substantially pure Rp,Rp or Rp,Sp diastereomers, or prodrugs or pharmaceutically acceptable salts thereof to the individual. Preferred routes of administration are parenteral. As noted above, particularly preferred are thiophosphate derivatives of such cyclic purine dinucleotides.

The methods described herein can comprise administering to the mammal an effective amount of the substantially pure CDNs of the present invention, or prodrugs or pharmaceutically acceptable salts thereof, prior to or following a primary therapy administered to the mammal to remove or kill cancer cells expressing the cancer antigen. The compositions of the present invention may be provided as a neoadjuvant therapy; however in preferred embodiments, the compositions of the present invention are administered following the primary therapy. In various embodiments, the primary therapy comprises surgery to remove the cancer cells from the mammal, radiation therapy to kill the cancer cells in the mammal, or both surgery and radiation therapy.

In other embodiments, the methods described herein can comprise administering to the mammal an effective amount of the substantially pure CDNs of the present invention for the treatment of disorders in which shifting of Th1 to Th2 immunity confers clinical benefit. Cell-mediated immunity (CMI) is associated with TH1 CD4+ T lymphocytes producing cytokines IL-2, interferon (IFN)-γ and tumor necrosis factor (TNF)-α. In contrast, humoral immunity is associated with TH2 CD4+ T lymphocytes producing IL-4, IL-6 and IL-10. Immune deviation towards TH1 responses typically produces activation of cytotoxic T-cell lymphocytes (CTL), natural killer (NK) cells, macrophages and monocytes. Generally, Th1 responses are more effective against intracellular pathogens (viruses and bacteria that are inside host cells) and tumors, while Th2 responses are more effective against extracellular bacteria, parasites including helminths and toxins. In addition, the activation of innate immunity is expected to normalize the T-helper type 1 and 2 (Th1/Th2) immune system balance and to suppress the excessive reaction of Th2 type responses that cause immunoglobulin (Ig) E-dependent allergies and allergic asthma.

DETAILED DESCRIPTION OF THE INVENTION

Figure 1:
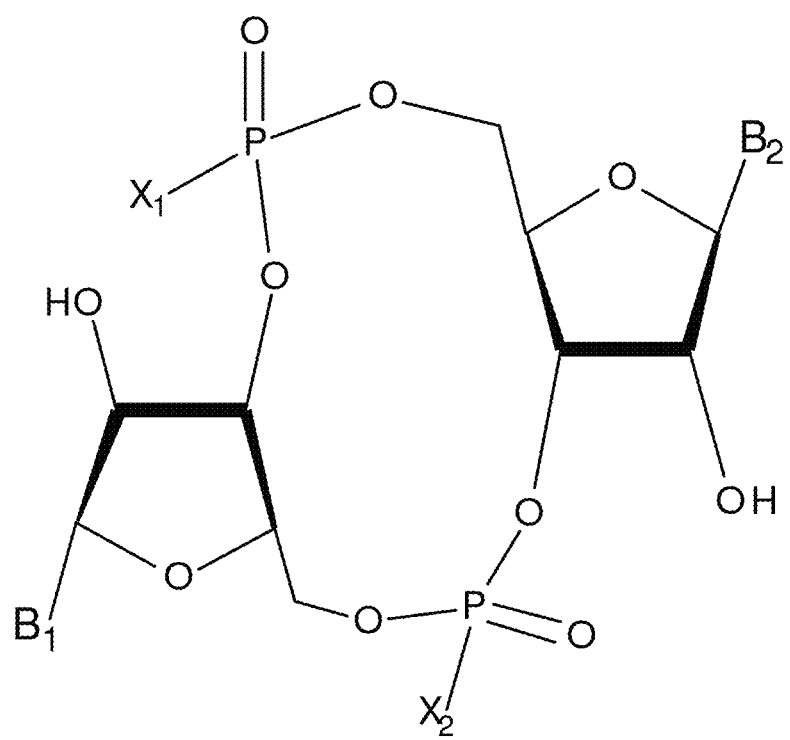
FIG. 1 depicts a general structure of CDNs.
Figure 2:
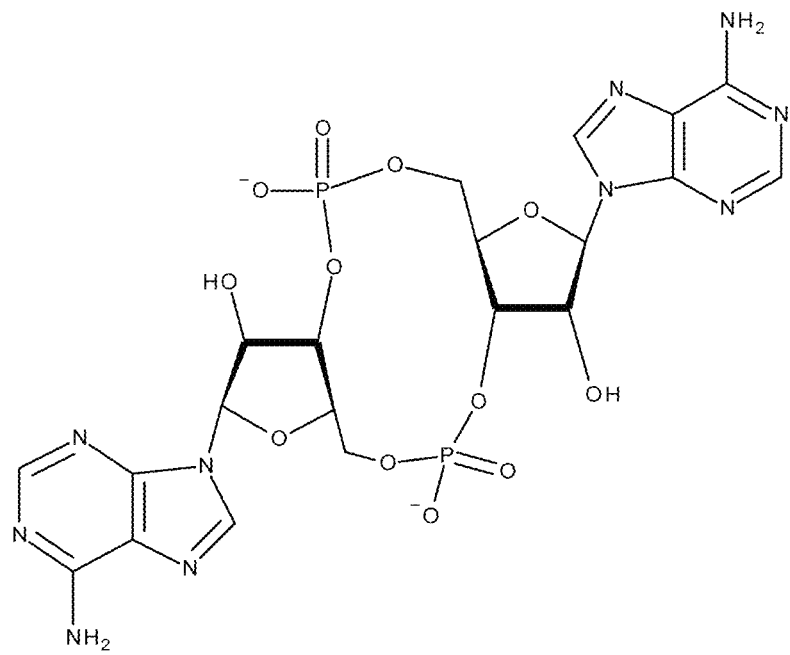
FIG. 2 depicts a structure of c-di-GMP (compound 11A) and c-di-AMP (compound 10A).
Figure 2:
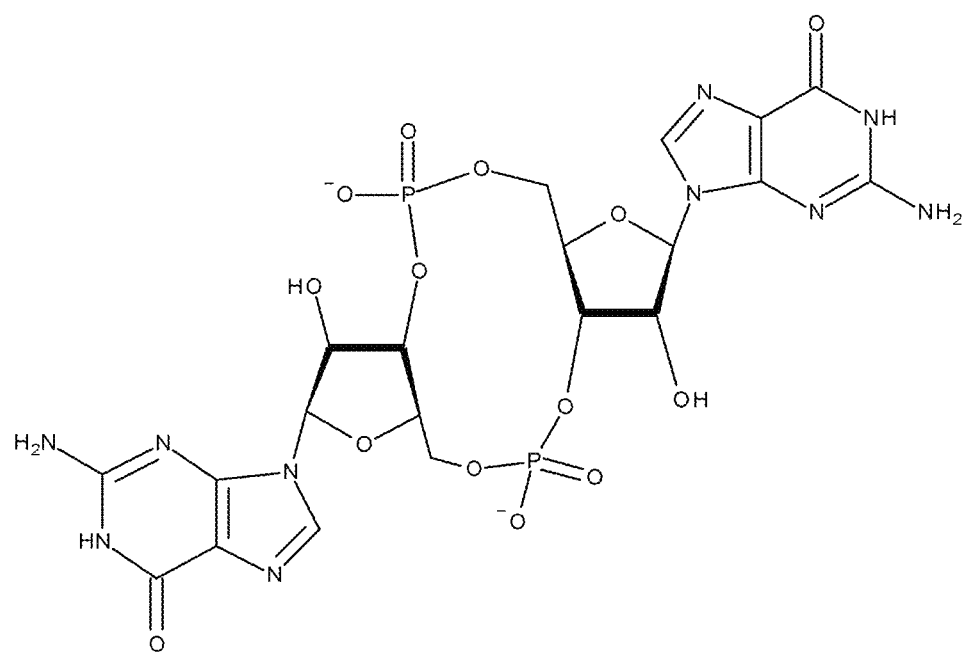
Figure 3:
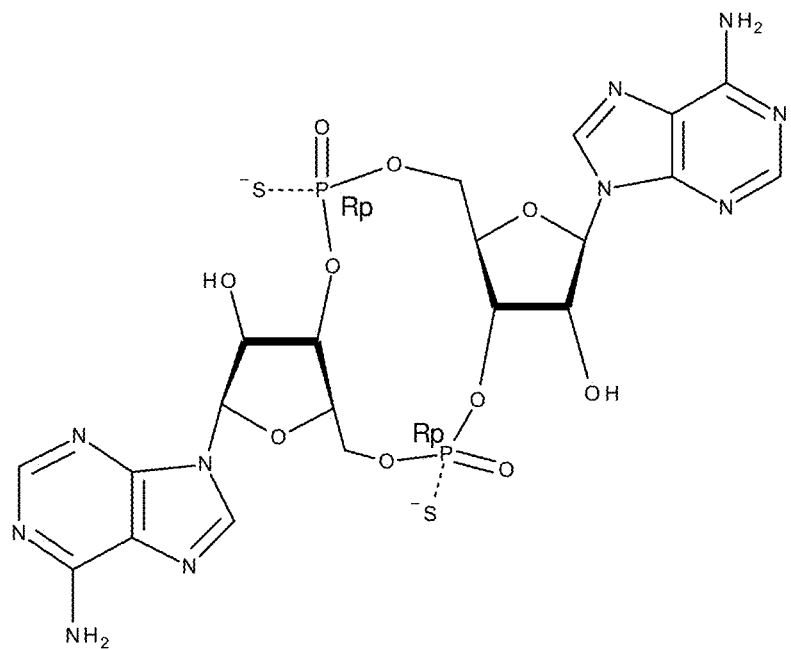
FIG. 3 depicts a structure of Rp,Rp-c-di-GMP-thiophosphate (compound 11B) and Rp,Rp-c-di-AMP-thiophosphate (compound 10B).
Figure 3:
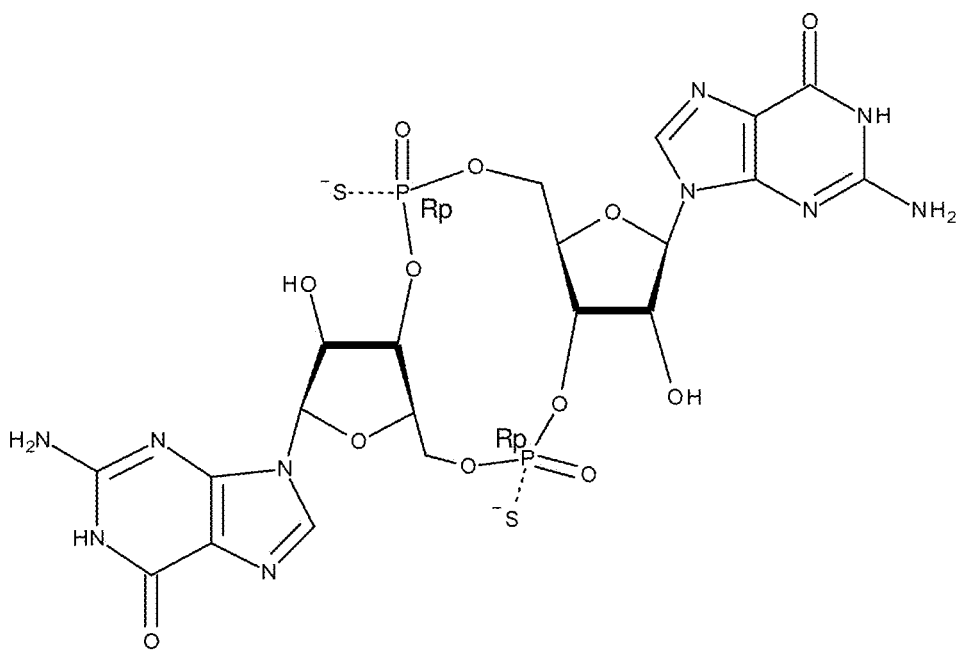
Figure 4:
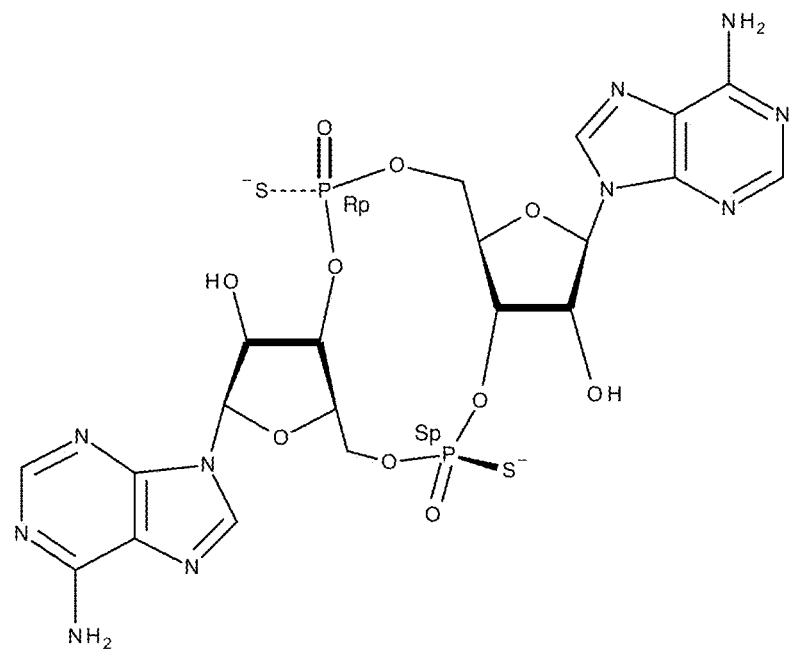
FIG. 4 depicts a structure of Rp,Sp-c-di-GMP-thiophosphate (compound 11C) and Rp,Sp-c-di-AMP-thiophosphate (compound 10C).
Figure 4:
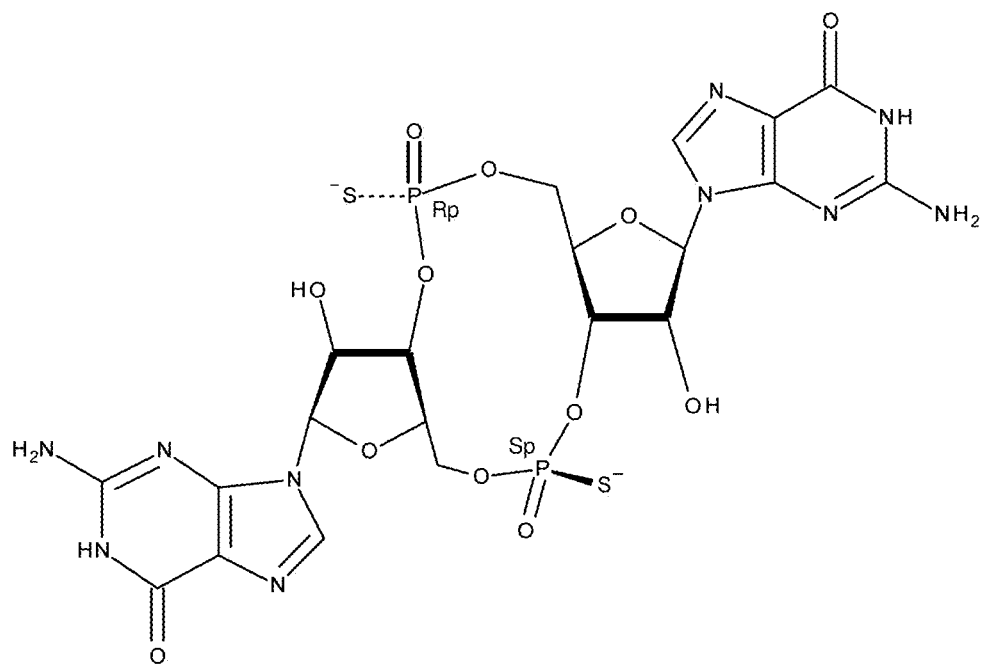
Figure 5:
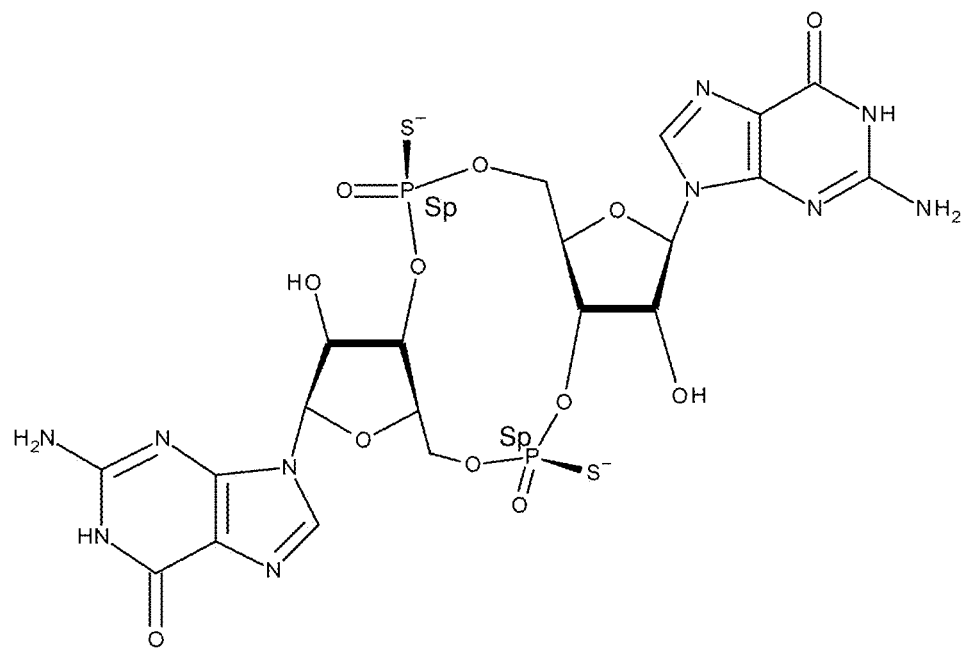
FIG. 5 depicts a structure of Sp,Sp-c-di-GMP-thiophosphate and Sp,Sp-c-di-AMP-thiophosphate.
Figure 5:
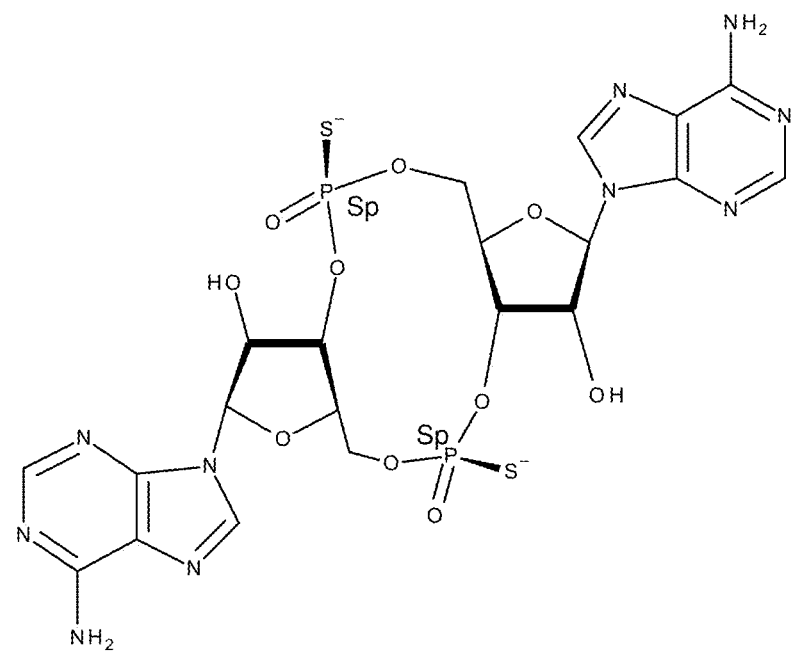

The present invention relates to the use of novel and highly active cyclic-di-nucleotide (CDN) immune stimulators that activates DCs via a recently discovered cytoplasmic receptor known as STING (Stimulator of Interferon Genes). In particular, the CDNs of the present invention are provided in the form of a composition comprising one or more cyclic purine dinucleotides induce STING-dependent TBK1 activation, wherein the cyclic purine dinuclotides present in the composition are substantially pure Rp,Rp or Rp,Sp stereoisomers, and particularly substantially pure Rp,Rp, or RpSp CDN thiophosphate diastereomers.

Recent insights into the design and development of adjuvants are informed by a fundamental understanding that conserved microbial structures known as Pathogen-Associated Molecular Patterns (PAMPs) are sensed by host cell Pattern Recognition Receptors (PRRs), triggering a downstream signaling cascade resulting in the induction of cytokines and chemokines, and initiation of a specific adaptive immune response. How the innate immune system is engaged by the PAMP complement of a microbe shapes the development of an adaptive response that is appropriate to combat the invading pathogen from causing disease. An objective of adjuvant design is to select defined PAMPs or synthetic molecules specific for designated PRRs to initiate a desired response. Adjuvants such as monophosphoryl lipid A (MPL) and CpG are PAMPs recognized by Toll-like receptors (TLRs), a class of transmembrane PRRs that signal through MyD88 and Trif adaptor molecules and mediate induction of NF-kB dependent proinflammatory cytokines. MPL (TLR-4 agonist) and CpG (TLR-9 agonist) are clinically advanced adjuvants, and are components of vaccines that are approved or pending approval by the FDA. While TLRs present on the cell surface (e.g., TLR-4) and endosomes (e.g., CpG) sense extracellular and vacuolar pathogens, the productive growth cycle of multiple pathogens including viruses and intracellular bacteria occurs in the cytosol. The compartmentalization of extracellular, vacuolar, and cytosolic PRRs has led to the hypothesis that the innate immune system distinguishes between pathogenic and non-pathogenic microbes by monitoring the cytosol. It should be apparent to one skilled in the art that agonists specific for PRRs comprising the cytosolic surveillance pathway that initiate development of protective immunity against intracellular pathogens, and is relevant to vaccine design. These same targeting ligands will also be essential in the development of effective vaccines targeting malignancies, know to require tumor-specific CD4+ and CD8+ T cells.

Activation of the Cytosolic Surveillance Pathway (CSP) is Integral to Development of Protective Immunity to Intracellular Pathogens. The CSP detects bacterial, viral, and protozoan pathogens, leading to activation of the TANK binding kinase (TBK-1)/IRF-3 signaling axis and induction of IFN-β and other co-regulated genes. Both viral and bacterial nucleic acids activate this pathway, and induction of IFN-β is MyD88 and Trif independent. While Type I interferon is often thought of primarily as a host anti-viral response, induction of IFN-β is a signature of cytosolic growth in macrophages infected with the intracellular bacterium, *Listeria monocytogenes* (Lm). A well-known dichotomy in the mouse listeriosis model is that, whereas wild-type Lm primes potent CD4 and CD8 T-cell immunity that protects mice against bacterial challenge, vaccination with listeriolysin O (LLO)-deleted Lm does not elicit functional T cells or induce protective immunity. This difference is evidence of the requirement for expression of host cell genes and cytosolic access by Lm to elicit functional T-cell mediated protective immunity. The level of IFN-β in infected host cells is regulated by Lm multidrug efflux pumps (MDRs), which that secrete structurally unrelated small molecules, including antibiotics. IFN-β is not induced in host cells infected with Lm LLO mutants that are confined to the phagolysosome. Normal levels of IFN-β are induced in infected MyD88$^{-/-}$ Trif$^{-/-}$ macrophages deficient in all TLR-mediated signaling. These data demonstrate that although Lm engages TLRs, in response to infection with wild-type Lm, the host cell CSP is required for development of protective immunity, correlated with induction of IFN-β.

The term "cyclic-di-nucleotides" ("CDNs") as used herein refers to a class of molecules comprising 2'-5' and/or 3'-5' phosphodiester linkages between two purine nucleotides. This includes 2'-5'-2',5', 2'-5'-3'5', and 3',5'-3',5' linkages. CDNs activate the cytosolic surveillance pathway through direct binding of two cytosolic PRRs, DDX41 and STING. The Type I interferon response to infection by Lm and other intracellular bacteria results from the secretion of c-di-AMP or its related cyclic dinucleotide (CDN), c-di-GMP, and its direct binding to DDX41 and DEAD (aspartate-glutamate-alanine-aspartate) box helicase and STING (Stimulator of Interferon Genes), a recently defined receptor of the cytosolic surveillance pathway. CDNs are second messengers expressed by most bacteria and regulate diverse processes, including motility and formation of biofilms. CDNs bind with high affinity to DDX41, and complex with the STING adaptor protein, resulting in the activation of the TBK1/IRF3 signaling pathway, and induction of IFN-β and other IRF-3 dependent gene products that strongly activate innate immunity.

Native CDN molecules are sensitive to degradation by phosphodiesterases that are present in host cells, for example in antigen presenting cells, that take up vaccine formulations that contain said native CDN molecules. The potency of a defined adjuvant may be diminished by such degradation, as the adjuvant would be unable to bind and activate its defined PRR target. Lower adjuvant potency could be measured, for example by a lower amount of induced expression of a signature molecule of innate immunity (e.g., IFN-β), correlated with weaker vaccine potency, as defined by the magnitude of a measured antigen-specific immune response.

In the present invention, dithio-diphosphate derivatives of c-di-AMP and c-di-GMP are provided. The synthesis process for said dithio-diphosphate derivatives of c-di-AMP and c-di-GMP molecules results in a mixture of diastereomers, including Rp,Rp, Sp,Sp and Rp,Sp dithio-diphosphate derivatives of c-di-AMP and c-di-GMP molecules. It has been shown previously that said mixtures of diastereomers containing Rp, Rp and Rp, Sp dithio-diphosphate derivatives of c-di-GMP recruited and activated inflammatory cells into the bronchoalveolar spaces when administered to mice by an intranasal route. However, there was no evidence that this such dithio-diphosphate derivatives of c-di-GMP provided any advantages with regard to stimulating an immune response, as compared to the parent c-di-GMP molecules, and, in fact, such dithio-diphosphate c-di-GMP preparations had only similar or weaker potency as compared to the parent c-di-GMP molecules.

DEFINITIONS

"Administration" as it is used herein with regard to a human, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses contact of a reagent to the cell, as well as contact of a reagent to a fluid, where the fluid is in contact with the cell. "Administration" also encompasses in vitro and ex vivo treatments, e.g., of a cell, by a reagent, diagnostic, binding composition, or by another cell. By "administered together" it is not meant to be implied that two or more agents be administered as a single composition. Although administration as a single composition is contemplated by the present invention, such agents may be delivered to a single subject as separate administrations, which may be at the same or different time, and which may be by the same route or different routes of administration.

An "agonist," as it relates to a ligand and receptor, comprises a molecule, combination of molecules, a complex, or a combination of reagents, that stimulates the receptor. For example, an agonist of granulocyte-macrophage colony stimulating factor (GM-CSF) can encompass GM-CSF, a mutein or derivative of GM-CSF, a peptide mimetic of GM-CSF, a small molecule that mimics the biological function of GM-CSF, or an antibody that stimulates GM-CSF receptor.

An "antagonist," as it relates to a ligand and receptor, comprises a molecule, combination of molecules, or a complex, that inhibits, counteracts, downregulates, and/or desensitizes the receptor. "Antagonist" encompasses any reagent that inhibits a constitutive activity of the receptor. A constitutive activity is one that is manifest in the absence of a ligand/receptor interaction. "Antagonist" also encompasses any reagent that inhibits or prevents a stimulated (or regulated) activity of a receptor. By way of example, an antagonist of GM-CSF receptor includes, without implying any limitation, an antibody that binds to the ligand (GM-CSF) and prevents it from binding to the receptor, or an antibody that binds to the receptor and prevents the ligand from binding to the receptor, or where the antibody locks the receptor in an inactive conformation.

As used herein, an "analog" or "derivative" with reference to a peptide, polypeptide or protein refers to another peptide, polypeptide or protein that possesses a similar or identical function as the original peptide, polypeptide or protein, but does not necessarily comprise a similar or identical amino acid sequence or structure of the original peptide, polypeptide or protein. An analog preferably satisfies at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the original amino acid sequence (b) a proteinaceous agent encoded by a nucleotide sequence that hybridizes under stringent conditions to a nucleotide sequence encoding the original amino acid sequence; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the original amino acid sequence.

"Antigen presenting cells" (APCs) are cells of the immune system used for presenting antigen to T cells. APCs include dendritic cells, monocytes, macrophages, marginal zone Kupffer cells, microglia, Langerhans cells, T cells, and B cells. Dendritic cells occur in at least two lineages. The first lineage encompasses pre-DC1, myeloid DC1, and mature DC1. The second lineage encompasses $CD34^+$ $CD45RA^-$ early progenitor multipotent cells, $CD34^+$ $CD45RA^+$ cells, $CD34^+CD45RA^+CD4^+$ $IL-3R\alpha^+$ pro-DC2 cells, $CD4^+CD11c^-$ plasmacytoid pre-DC2 cells, lymphoid human DC2 plasmacytoid-derived DC2s, and mature DC2s.

"Attenuation" and "attenuated" encompasses a bacterium, virus, parasite, infectious organism, prion, tumor cell, gene in the infectious organism, and the like, that is modified to reduce toxicity to a host. The host can be a human or animal host, or an organ, tissue, or cell. The bacterium, to give a non-limiting example, can be attenuated to reduce binding to a host cell, to reduce spread from one host cell to another host cell, to reduce extracellular growth, or to reduce intracellular growth in a host cell. Attenuation can be assessed by measuring, e.g., an indicum or indicia of toxicity, the $LD_{50}$, the rate of clearance from an organ, or the competitive index (see, e.g., Auerbuch, et al. (2001) Infect. Immunity 69:5953-5957). Generally, an attenuation results an increase in the $LD_{50}$ and/or an increase in the rate of clearance by at least 25%; more generally by at least 50%; most generally by at least 100% (2-fold); normally by at least 5-fold; more normally by at least 10-fold; most normally by at least 50-fold; often by at least 100-fold; more often by at least 500-fold; and most often by at least 1000-fold; usually by at least 5000-fold; more usually by at least 10,000-fold; and most usually by at least 50,000-fold; and most often by at least 100,000-fold.

By "purified" and "isolated" is meant that a specified species accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the species present in a composition. The weights of water, buffers, salts, detergents, reductants, protease inhibitors, stabilizers (including an added protein such as albumin), and excipients are generally not used in the determination of purity.

"Specifically" or "selectively" binds, when referring to a ligand/receptor, nucleic acid/complementary nucleic acid, antibody/antigen, or other binding pair (e.g., a cytokine to a cytokine receptor) (each generally referred to herein as a "target biomolecule" or a "target") indicates a binding reaction which is related to the presence of the target in a heterogeneous population of proteins and other biologics. Specific binding can mean, e.g., that the binding compound, nucleic acid ligand, antibody, or binding composition derived from the antigen-binding site of an antibody, of the contemplated method binds to its target with an affinity that is often at least 25% greater, more often at least 50% greater, most often at least 100% (2-fold) greater, normally at least ten times greater, more normally at least 20-times greater, and most normally at least 100-times greater than the affinity with a non-target molecule.

"Ligand" refers to a small molecule, nucleic acid, peptide, polypeptide, saccharide, polysaccharide, glycan, glycoprotein, glycolipid, or combinations thereof that binds to a target biomolecule. While such ligands may be agonists or antagonists of a receptor, a ligand also encompasses a binding agent that is not an agonist or antagonist, and has no agonist or antagonist properties. Specific binding of a ligand for its cognate target is often expressed in terms of an "Affinity." In preferred embodiments, the ligands of the present invention bind with affinities of between about $10^4$ $M^{-1}$ and about $10^8$ $M^{-1}$. Affinity is calculated as $K_d = k_{off}/k_{on}$ ($k_{off}$ is the dissociation rate constant, $K_{on}$ is the association rate constant and $K_d$ is the equilibrium constant).

Affinity can be determined at equilibrium by measuring the fraction bound (r) of labeled ligand at various concentrations (c). The data are graphed using the Scatchard equation: r/c=K(n−r): where r=moles of bound ligand/mole of receptor at equilibrium; c=free ligand concentration at equilibrium; K=equilibrium association constant; and n=number of ligand binding sites per receptor molecule. By graphical analysis, r/c is plotted on the Y-axis versus r on the X-axis, thus producing a Scatchard plot. Affinity measurement by Scatchard analysis is well known in the art. See, e.g., van Erp et al., *J. Immunoassay* 12: 425-43, 1991; Nelson and Griswold, *Comput. Methods Programs Biomed.* 27: 65-8, 1988. In an alternative, affinity can be measured by isothermal titration calorimetry (ITC). In a typical ITC experiment, a solution of ligand is titrated into a solution of its cognate target. The heat released upon their interaction (ΔH) is monitored over time. As successive amounts of the ligand are titrated into the ITC cell, the quantity of heat absorbed or released is in direct proportion to the amount of binding. As the system reaches saturation, the heat signal diminishes until only heats of dilution are observed. A binding curve is then obtained from a plot of the heats from each injection against the ratio of ligand and binding partner in the cell. The binding curve is analyzed with the appropriate binding model to determine $K_B$, n and ΔH. Note that $K_B=1/K_d$.

The term "subject" as used herein refers to a human or non-human organism. Thus, the methods and compositions described herein are applicable to both human and veterinary disease. In certain embodiments, subjects are "patients," i.e., living humans that are receiving medical care for a disease or condition. This includes persons with no defined illness who are being investigated for signs of pathology. Preferred are subjects who have an existing diagnosis of a particular cancer which is being targeted by the compositions and methods of the present invention. Preferred cancers for treatment with the compositions described herein include, but are not limited to prostate cancer, renal carcinoma, melanoma, pancreatic cancer, cervical cancer, ovarian cancer, colon cancer, head & neck cancer, lung cancer and breast cancer.

"Therapeutically effective amount" is defined as an amount of a reagent or pharmaceutical composition that is sufficient to show a patient benefit, i.e., to cause a decrease, prevention, or amelioration of the symptoms of the condition being treated. When the agent or pharmaceutical composition comprises a diagnostic agent, a "diagnostically effective amount" is defined as an amount that is sufficient to produce a signal, image, or other diagnostic parameter. Effective amounts of the pharmaceutical formulation will vary according to factors such as the degree of susceptibility of the individual, the age, gender, and weight of the individual, and idiosyncratic responses of the individual. "Effective amount" encompasses, without limitation, an amount that can ameliorate, reverse, mitigate, prevent, or diagnose a symptom or sign of a medical condition or disorder or a causative process thereof. Unless dictated otherwise, explicitly or by context, an "effective amount" is not limited to a minimal amount sufficient to ameliorate a condition.

"Treatment" or "treating" (with respect to a condition or a disease) is an approach for obtaining beneficial or desired results including and preferably clinical results. For purposes of this invention, beneficial or desired results with respect to a disease include, but are not limited to, one or more of the following: preventing a disease, improving a condition associated with a disease, curing a disease, lessening severity of a disease, delaying progression of a disease, alleviating one or more symptoms associated with a disease, increasing the quality of life of one suffering from a disease, and/or prolonging survival. Likewise, for purposes of this invention, beneficial or desired results with respect to a condition include, but are not limited to, one or more of the following: preventing a condition, improving a condition, curing a condition, lessening severity of a condition, delaying progression of a condition, alleviating one or more symptoms associated with a condition, increasing the quality of life of one suffering from a condition, and/or prolonging survival. For instance, in embodiments where the compositions described herein are used for treatment of cancer, the beneficial or desired results include, but are not limited to, one or more of the following: reducing the proliferation of (or destroying) neoplastic or cancerous cells, reducing metastasis of neoplastic cells found in cancers, shrinking the size of a tumor, decreasing symptoms resulting from the cancer, increasing the quality of life of those suffering from the cancer, decreasing the dose of other medications required to treat the disease, delaying the progression of the cancer, and/or prolonging survival of patients having cancer. Depending on the context, "treatment" of a subject can imply that the subject is in need of treatment, e.g., in the situation where the subject comprises a disorder expected to be ameliorated by administration of a reagent.

By "purified" and "isolated" is meant, when referring to a polypeptide, that the polypeptide is present in the substantial absence of the other biological macromolecules with which it is associated in nature. The term "purified" as used herein means that an identified polypeptide often accounts for at least 50%, more often accounts for at least 60%, typically accounts for at least 70%, more typically accounts for at least 75%, most typically accounts for at least 80%, usually accounts for at least 85%, more usually accounts for at least 90%, most usually accounts for at least 95%, and conventionally accounts for at least 98% by weight, or greater, of the polypeptides present. The weights of water, buffers, salts, detergents, reductants, protease inhibitors, stabilizers (including an added protein such as albumin), and excipients, and molecules having a molecular weight of less than 1000, are generally not used in the determination of polypeptide purity. See, e.g., discussion of purity in U.S. Pat. No. 6,090,611 issued to Covacci, et al.

"Peptide" refers to a short sequence of amino acids, where the amino acids are connected to each other by peptide bonds. A peptide may occur free or bound to another moiety, such as a macromolecule, lipid, oligo- or polysaccharide, and/or a polypeptide. Where a peptide is incorporated into a polypeptide chain, the term "peptide" may still be used to refer specifically to the short sequence of amino acids. A "peptide" may be connected to another moiety by way of a peptide bond or some other type of linkage. A peptide is at least two amino acids in length and generally less than about 25 amino acids in length, where the maximal length is a function of custom or context. The terms "peptide" and "oligopeptide" may be used interchangeably.

"Protein" generally refers to the sequence of amino acids comprising a polypeptide chain. Protein may also refer to a three dimensional structure of the polypeptide. "Denatured protein" refers to a partially denatured polypeptide, having some residual three dimensional structure or, alternatively, to an essentially random three dimensional structure, i.e., totally denatured. The invention encompasses reagents of, and methods using, polypeptide variants, e.g., involving glycosylation, phosphorylation, sulfation, disulfide bond formation, deamidation, isomerization, cleavage points in signal or leader sequence processing, covalent and non-covalently bound cofactors, oxidized variants, and the like. The formation of disulfide linked proteins is described (see, e.g., Woycechowsky and Raines (2000) Curr. Opin. Chem. Biol. 4:533-539; Creighton, et al. (1995) Trends Biotechnol. 13:18-23).

"Recombinant" when used with reference, e.g., to a nucleic acid, cell, animal, virus, plasmid, vector, or the like, indicates modification by the introduction of an exogenous, non-native nucleic acid, alteration of a native nucleic acid, or by derivation in whole or in part from a recombinant nucleic acid, cell, virus, plasmid, or vector. Recombinant protein refers to a protein derived, e.g., from a recombinant nucleic acid, virus, plasmid, vector, or the like. "Recombinant bacterium" encompasses a bacterium where the genome is engineered by recombinant methods, e.g., by way of a mutation, deletion, insertion, and/or a rearrangement. "Recombinant bacterium" also encompasses a bacterium modified to include a recombinant extra-genomic nucleic acid, e.g., a plasmid or a second chromosome, or a bacterium where an existing extra-genomic nucleic acid is altered.

"Sample" refers to a sample from a human, animal, placebo, or research sample, e.g., a cell, tissue, organ, fluid, gas, aerosol, slurry, colloid, or coagulated material. The "sample" may be tested in vivo, e.g., without removal from the human or animal, or it may be tested in vitro. The sample may be tested after processing, e.g., by histological methods. "Sample" also refers, e.g., to a cell comprising a fluid or tissue sample or a cell separated from a fluid or tissue sample. "Sample" may also refer to a cell, tissue, organ, or fluid that is freshly taken from a human or animal, or to a cell, tissue, organ, or fluid that is processed or stored.

"Vaccine" encompasses preventative vaccines. Vaccine also encompasses therapeutic vaccines, e.g., a vaccine administered to a mammal that comprises a condition or disorder associated with the antigen or epitope provided by the vaccine.

The term "antibody" as used herein refers to a peptide or polypeptide derived from, modeled after or substantially encoded by an immunoglobulin gene or immunoglobulin genes, or fragments thereof, capable of specifically binding an antigen or epitope. See, e.g. Fundamental Immunology, 3rd Edition, W. E. Paul, ed., Raven Press, N.Y. (1993); Wilson (1994; J. Immunol. Methods 175:267-273; Yarmush (1992) J. Biochem. Biophys. Methods 25:85-97. The term antibody includes antigen-binding portions, i.e., "antigen binding sites," (e.g., fragments, subsequences, complementarity determining regions (CDRs)) that retain capacity to bind antigen, including (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR). Single chain antibodies are also included by reference in the term "antibody."

Cyclic Purine Dinucleotides

As described herein, the present invention relates to stereochemically purified cyclic purine dinucleotides which induce STING-dependent TBK1 activation and their methods of preparation and use.

Prokaryotic as well as eukaryotic cells use various small molecules for cell signaling and intra- and intercellular communication. Cyclic nucleotides like cGMP, cAMP, etc. are known to have regulatory and initiating activity in pro- and eukaryotic cells. Unlike eukaryotic cells, prokaryotic cells also use cyclic purine dinucleotides as regulatory molecules. In prokaryotes, the condensation of two GTP molecules is catalyst by the enzyme diguanylate cyclase (DGC) to give c-diGMP, which represents an important regulator in bacteria.

Recent work suggests that CDNs such as cyclic diGMP or analogs thereof can also stimulate or enhance immune or inflammatory response in a patient or can enhance the immune response to a vaccine by serving as an adjuvant in mammals. Cytosolic detection of pathogen-derived DNA requires signaling through TANK binding kinase 1 (TBK1) and its downstream transcription factor, IFN-regulatory factor 3 (IRF3). A transmembrane protein called STING (stimulator of IFN genes; also known as MITA, ERIS, MPYS and TMEM173) functions as the signaling receptor for these cyclic purine dinucleotides, causing stimulation of the TBK1-IRF3 signalling axis and a STING-dependent type I interferon response. See, e.g., FIG. 1. Burdette et al., Nature 478: 515-18, 2011 demonstrated that STING binds directly to cyclic diguanylate monophosphate, but not to other unrelated nucleotides or nucleic acids.

The goal of vaccine formulation is typically to provide a combination of antigens and adjuvants capable of generating a sufficient population of memory T cells and/or B cells to react quickly to a pathogen, tumor cell, etc., bearing an antigen of interest. The present invention relates to methods for providing adjuvant compositions comprising one or more cyclic purine dinucleotides, wherein the cyclic purine dinuclotides present in the composition are substantially pure Rp,Rp or Rp,Sp diastereomers, methods for the manufacture thereof, and methods for the use thereof to stimulate an immune response in an animal.

Preferred cyclic purine dinuclotides include, but are not limited to, c-di-AMP, c-di-GMP, c-di-IMP, c-AMP-GMP, c-AMP-IMP, and c-GMP-IMP, and analogs thereof including, but not limited to, phosphorothioate analogues, referred to herein as "thiophosphates". A general structure of CDN thiophsphate is provided in FIG. 1. In this figure, B1 and B2 represent the base moiety. Phosphorothioates are a variant of normal nucleotides in which one of the nonbridging oxygens is replaced by a sulfur. The sulfurization of the internucleotide bond dramatically reduces the action of endo- and exonucleases, including 5' to 3' and 3' to 5' DNA POL 1 exonuclease, nucleases S1 and P1, RNases, serum nucleases and snake venom phosphodiesterase. In addition, the potential for crossing the lipid bilayer increases.

A phosphorothioate linkage in inherently chiral. The skilled artisan will recognize that the phosphates in this structure may each exist in R or S forms. Thus, Rp,Rp, Sp,Sp, and Rp,Sp forms are possible. In each case, preferred are substantially pure Rp,Rp and Rp,Sp diastereomers of these molecules. Examples of such CDN thiophosphate molecules are depicted in FIGS. 2-6 herein, which show thiophosphate forms of Rp,Rp-c-di-adenosine monophosphate; Rp,Sp-c-di-adenosine monophosphate; Rp,Rp-c-di-guanosine monophosphate and Rp,Sp-c-di-guanosine monophosphate. In these figures, the stereochemistry of the phosphate center is shown as R or S, as appropriate.

Figure 11:
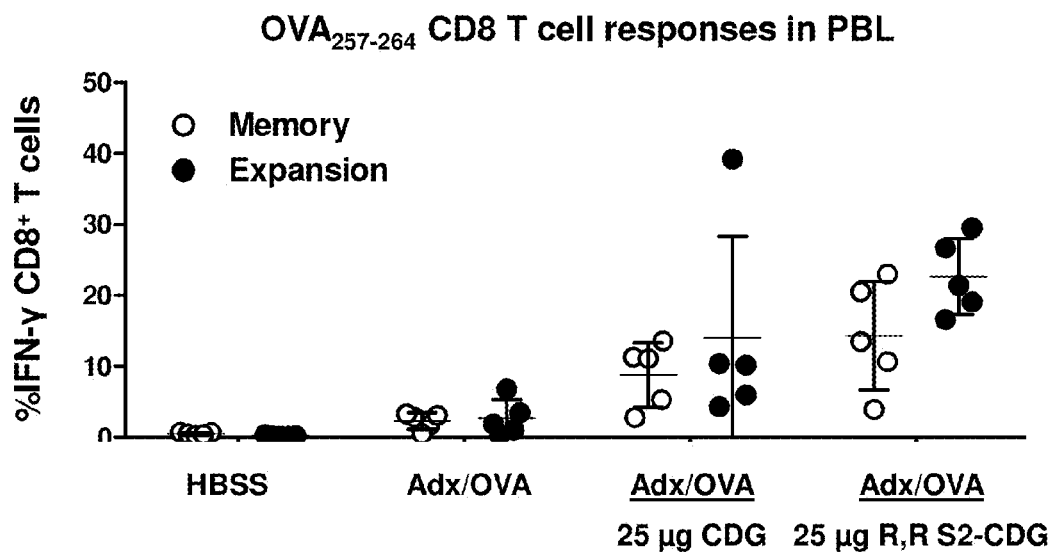
FIG. 11 depicts protection induced by CDN in a *Listeria*-OVA challenge murine model.
Figure 11:
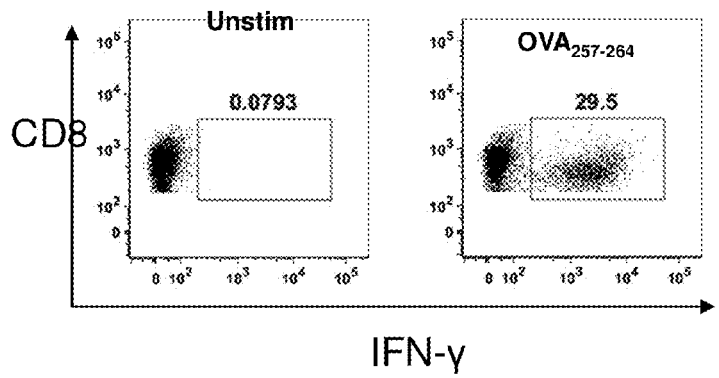

Preferred cyclic purine dinuclotides also include 2'-O-substituent forms of CDNs, and in particular CDN thiophosphates. Additional stability and bioavailability can be provided by the substitution of the 2'-OH of the ribose moiety. An example of such 2'-O-substituent analogs are shown in FIG. 11. Substituent groups amenable herein include without limitation, halogen, hydroxyl, alkyl, alkenyl, alkynyl, acyl (—C(0)$R_{aa}$), carboxyl (—C(0)0-$R_{aa}$), aliphatic groups, alicyclic groups, alkoxy, substituted oxy (-0-$R_{aa}$), aryl, aralkyl, heterocyclic radical, heteroaryl, heteroarylalkyl, amino (—N($R_{bb}$)($R_{cc}$)), imino (=N$R_{bb}$), amido (—C(0)N($R_{bb}$)(Rc$_C$) or —N($R_{bb}$)C(0)$R_{aa}$), azido (—$N_3$), nitro (—$NO_2$), cyano (—CN), carbamido (—OC(0)N($R_{bb}$)($R_{cc}$) or —N($R_{bb}$)C(0)O$R_{aa}$), ureido (—N($R_{bb}$)C(0)-N(Rbb)(Rcc)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)(Rc$_C$) or —N($R_{bb}$)C(=N$R_{bb}$)($R_{aa}$)), thiol (—S$R_{bb}$), sulfinyl (—S(0)$R_{bb}$), sulfonyl (—S(0)$_2R_b$) and sulfonamidyl (—S(0)$_2$N($R_{bb}$)(Rc$_C$) or —N($R_{bb}$)S(0)$_2R_{bb}$). Wherein each $R_{aa}$, $R_{bb}$ and $R_{cC}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

Still other preferred cyclic purine dinuclotides also include S-substituent forms of CDNs, and in particular CDN thiophosphates, which can advantageously provide prodrugs with improved bioavailability. The term "prodrug" as used herein refers to a modification of contemplated compounds, wherein the modified compound is converted within the body (e.g., in a target cell or target organ) back into the unmodified form through enzymatic or non-enzymatic reactions. In certain embodiments, the hydroxyl on one ribose comprises a prodrug leaving group. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

Figure 12:
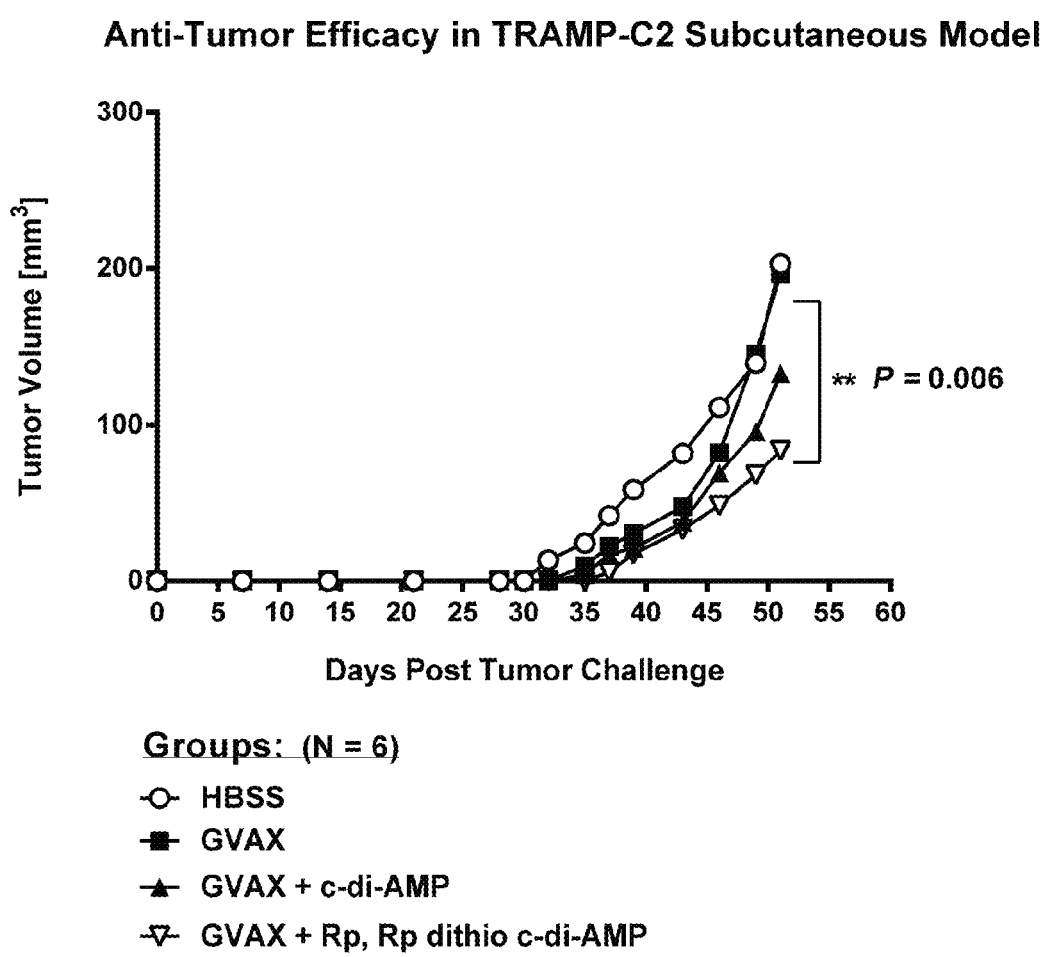
FIG. 12 depicts anti-tumor efficacy induced by CDNs formulated with GVAX in a murine prostate cancer model.

An example of such prodrug analogs are shown in FIG. 12. This prodrug form with improved lipophilicity may be cleaved into active forms through the action of esterases present in target organisms. Substituent groups amenable herein include without limitation, halogen, hydroxyl, alkyl, alkenyl, alkynyl, acyl (—C(0)$R_{aa}$), carboxyl (—C(0)0-$R_{aa}$), aliphatic groups, alicyclic groups, alkoxy, substituted oxy (—O-$R_{aa}$), aryl, aralkyl, heterocyclic radical, heteroaryl, heteroarylalkyl, amino (—N($R_{bb}$)($R_{cc}$)), imino (=N$R_{bb}$), amido (—C(0)N($R_{bb}$)(Rc$_C$) or —N($R_{bb}$)C(0)$R_{aa}$), azido (—$N_3$), nitro (—$NO_2$), cyano (—CN), carbamido (—OC(0)N($R_{bb}$)($R_{cc}$) or —N($R_{bb}$)C(0)O$R_{aa}$), ureido (—N($R_{bb}$)C(0)-N(Rbb)(Rcc)), thioureido (—N($R_{bb}$)C(S)N($R_{bb}$)($R_{cc}$)), guanidinyl (—N($R_{bb}$)C(=N$R_{bb}$)N($R_{bb}$)($R_{cc}$)), amidinyl (—C(=N$R_{bb}$)N($R_{bb}$)(Rc$_C$) or —N($R_{bb}$)C(=N$R_{bb}$)($R_{aa}$)), thiol (—S$R_{bb}$), sulfinyl (—S(0)$R_{bb}$), sulfonyl (—S(0)$_2R_b$) and sulfonamidyl (—S(0)$_2$N($R_{bb}$)(Rc$_C$) or —N($R_{bb}$)S(0)$_2R_{bb}$). Wherein each $R_{aa}$, $R_{bb}$ and $R_{cC}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree. Preferred substituents include methyl, isopropyl and t-butyl. Prodrug forms of nucleotides are known in the art. See, e.g., Nucleotide Prodrugs for HCV Therapy, Sofia, M. J., Antiviral Chem and Chemother., 2011, 22: 23-49; Nucleoside, Nucleotide, and Non-Nucleoside Inhibitors of Hepatitis C Virus NS5B RNA—Dependent RNA—Polymerase, Sofia, M. J., et al., J. Med. Chem., 2012, 55: 2481-2531.

The term "alkyl," as used herein, refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms with from 1 to about 6 carbon atoms being more preferred. The term "lower alkyl" as used herein includes from 1 to about 6 carbon atoms. Alkyl groups as used herein may optionally include one or more further substituent groups.

The term "alkenyl," as used herein, refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

The term "alkynyl," as used herein, refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

The term "acyl," as used herein, refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

The term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

The term "aliphatic," as used herein, refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

The term "alkoxy," as used herein, refers to a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

The term "aminoalkyl" as used herein, refers to an amino substituted C\-Cn alkyl radical. The alkyl portion of the radical forms a covalent bond with a parent molecule. The amino group can be located at any position and the aminoalkyl group can be substituted with a further substituent group at the alkyl and/or amino portions.

The terms "aralkyl" and "arylalkyl," as used herein, refer to an aromatic group that is covalently linked to a C\-Cn alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

The terms "aryl" and "aromatic," as used herein, refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

The terms "halo" and "halogen," as used herein, refer to an atom selected from fluorine, chlorine, bromine and iodine.

The terms "heteroaryl," and "heteroaromatic," as used herein, refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

The term "heteroarylalkyl," as used herein, refers to a heteroaryl group as previously defined that further includes a covalently attached $C_1$-$C_{12}$ alkyl radical. The alkyl radical portion of the resulting heteroarylalkyl group is capable of forming a covalent bond with a parent molecule. Examples include without limitation, pyridinylmethyl, pyrimidinylethyl, napthyridinylpropyl and the like. Heteroarylalkyl groups as used herein may optionally include further substituent groups on one or both of the heteroaryl or alkyl portions.

As noted above, preferred cyclic purine dinuclotides also include prodrug forms of CDNs, and in particular CDN thiophosphates. Prodrugs can modify the physicochemical, biopharmaceutic, and pharmacokinetic properties of drugs. Traditional prodrugs are classified as drugs that are activated by undergoing transformation in vivo to form the active drug. Reasons for prodrug development are typically poor aqueous solubility, chemical instability, low oral bioavailability, lack of blood brain barrier penetration, and high first pass metabolism associated with the parent drug. Suitable prodrug moieties are described in, for example, "Prodrugs and Targeted Delivery," J. Rautico, Ed., John Wiley & Sons, 2011.

The term "substantially pure" as used herein with regard to cyclic purine dinuclotides refers to an Rp,Rp or Rp,Sp form which is at least 75% pure relative to other possible stereochemistries at the chiral centers indicated in the figure above. By way of example, a "substantially pure Rp,Rp c-di-GMP thiophosphate" would be at least 75% pure with regard to the Rp,Sp and Sp,Sp forms of c-di-GMP thiophosphate. In preferred embodiments, a substantially pure cyclic purine dinuclotide is at least 85% pure, at least 90% pure, at least 95% pure, at least 97% pure, and at least 99% pure. While a substantially pure cyclic purine dinuclotide preparation of the invention is "stereochemically pure," this is not meant to indicate that all CDNs within the preparation having a particular stereochemistry at these chiral centers are otherwise identical. For example, a substantially pure cyclic purine dinuclotide preparation may contain a combination of Rp,Rp c-di-GMP thiophosphate and Rp,Rp c-di-AMP thiophosphate and still be a substantially pure cyclic purine dinuclotide preparation. Such a preparation may also include other components as described hereinafter that are advantageous for patient treatment, provided that all CDNs within the preparation having a particular stereochemistry at these chiral centers.

The CDN compositions described herein can be administered to a host, either alone or in combination with a pharmaceutically acceptable excipient, in an amount sufficient to induce, modify, or stimulate an appropriate immune response. The immune response can comprise, without limitation, specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the CDN compositions are administered in conjunction with one or more additional compositions including vaccines intended to stimulate an immune response to one or more predetermined antigens; adjuvants; CTLA-4 and PD-1 pathway antagonists, lipids, liposomes, chemotherapeutic agents, immunomodulatory cell lines, etc.

The CDN compositions may be administered before, after, and/or together with an additional therapeutic or prophylactic composition. These include, without limitation, B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Carriers for inducing a T cell immune response which preferentially stimulate a cytolytic T cell response versus an antibody response are preferred, although those that stimulate both types of response can be used as well. In cases where the agent is a polypeptide, the polypeptide itself or a polynucleotide encoding the polypeptide can be administered. The carrier can be a cell, such as an antigen presenting cell (APC) or a dendritic cell. Antigen presenting cells include such cell types as macrophages, dendritic cells and B cells. Other professional antigen-presenting cells include monocytes, marginal zone Kupffer cells, microglia, Langerhans' cells, interdigitating dendritic cells, follicular dendritic cells, and T cells. Facultative antigen-presenting cells can also be used. Examples of facultative antigen-presenting cells include astrocytes, follicular cells, endothelium and fibroblasts. The carrier can be a bacterial cell that is transformed to express the polypeptide or to deliver a polynucleoteide which is subsequently expressed in cells of the vaccinated individual. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryl lipid A, lipoteichoic acid, imiquimod, resiquimod, used separately or in combination with the described compositions are also potential adjuvants. Other representative examples of adjuvants include the synthetic adjuvant QS-21 comprising a homogeneous saponin purified from the bark of *Quillaja saponaria* and *Corynebacterium parvum* (McCune et al., Cancer, 1979; 43:1619). It will be understood that the adjuvant is subject to optimization. In other words, the skilled artisan can engage in routine experimentation to determine the best adjuvant to use.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Adjuvants

In addition to the cyclic purine dinuclotide(s) described above, the compositions of the present invention may further comprise one or more additional substances which, because of their adjuvant nature, can act to stimulate the immune system to respond to the cancer antigens present on the inactivated tumor cell(s). Such adjuvants include, but are not limited to, lipids, liposomes, inactivated bacteria which induce innate immunity (e.g., inactivated or attenuated *Listeria monocytogenes*), compositions which mediate innate immune activation via Toll-like Receptors (TLRs), (NOD)-like receptors (NLRs), Retinoic acid inducible gene-based (RIG)-I-like receptors (RLRs), and/or C-type lectin receptors (CLRs). Examples of PAMPs include lipoproteins, lipopolypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacterial. α-Galactosylceramide (α-GalCer) is an activator of natural killer T (NKT) cells. Muramyl dipeptide is a bioactive peptidoglycan motif common to all bacteria. This list is not meant to be limiting. Preferred adjuvant compositions are described below.

CTLA-4 and PD-1 Pathway Antagonists

CTLA-4 is thought to be an important negative regulator of the adaptive immune response. Activated T cells upregulate CTLA-4, which binds CD80 and CD86 on antigen-presenting cells with higher affinity than CD28, thus inhibiting T-cell stimulation, IL-2 gene expression and T-cell proliferation. Anti-tumor effects of CTLA4 blockade have been observed in murine models of colon carcinoma, metastatic prostate cancer, and metastatic melanoma.

Ipilimumab (Yervoy™) and tremelimumab are humanized monoclonal antibodies that bind to human CTLA4 and prevent its interaction with CD80 and CD86. Phase I and II studies using ipilimumab and tremelimumab have demonstrated clinical activity in cancer patients. Other negative immune regulators which may be targeted by a similar strategy include programmed cell death 1, B and T lymphocyte attenuator, transforming growth factor beta β, interleukin-10, and vascular endothelial growth factor.

PD-1 is another negative regulator of adaptive immune response that is expressed on activated T-cells. PD-1 binds to B7-H1 and B7-DC, and the engagement of PD-1 suppresses T-cell activation. Anti-tumor effects have been demonstrated with PD-1 pathway blockade. BMS-936558, MK3475, CT-011, AMP-224 and MDX-1106 have been reported in the literature to be examples of PD-1 pathway blockers which may find use in the present invention.

TLR Agonists

The term "Toll like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC). Toll like receptors (TLRs) are a family of pattern recognition receptors that were initially identified as sensors of the innate immune system that recognize microbial pathogens. TLRs comprise a family of conserved membrane spanning molecules containing an ectodomain of leucine-rich repeats, a transmembrane domain and an intracellular TIR (Toll/IL-1R) domain. TLRs recognize distinct structures in microbes, often referred to as "PAMPs" (pathogen associated molecular patterns). Ligand binding to TLRs invokes a cascade of intra-cellular signaling pathways that induce the production of factors involved in inflammation and immunity.

In humans, ten TLR have been identified. TLRs that are expressed on the surface of cells include TLR-1, -2, -4, -5, and -6, while TLR-3, -7/8, and -9 are expressed with the ER compartment. Human dendritic cell subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and II, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following:
Pam3Cys, a TLR-1/2 agonist;
CFA, a TLR-2 agonist;
MALP2, a TLR-2 agonist;
Pam2Cys, a TLR-2 agonist;
FSL-1, a TLR-2 agonist;
Hib-OMPC, a TLR-2 agonist;
polyribosinic:polyribocytidic acid (Poly I:C), a TLR-3 agonist;
polyadenosine-polyuridylic acid (poly AU), a TLR-3 agonist;
Polyinosinic-Polycytidylic acid stabilized with poly-L-lysine and carboxymethylcellulose (Hiltonol®), a TLR-3 agonist;
monophosphoryl lipid A (MPL), a TLR-4 agonist;
LPS, a TLR-4 agonist;
bacterial flagellin, a TLR-5 agonist;
sialyl-Tn (STn), a carbohydrate associated with the MUC1 mucin on a number of human cancer cells and a TLR-4 agonist;
imiquimod, a TLR-7 agonist;
resiquimod, a TLR-7/8 agonist;
loxoribine, a TLR-7/8 agonist; and
unmethylated CpG dinucleotide (CpG-ODN), a TLR-9 agonist.

Because of their adjuvant qualities, TLR agonists are preferably used in combinations with other vaccines, adjuvants and/or immune modulators, and may be combined in various combinations. Thus, in certain embodiments, the cyclic purine dinucleotides that bind to STING and induces STING-dependent TBK1 activation and an inactivated tumor cell which expresses and secretes one or more cytokines which stimulate dendritic cell induction, recruitment and/or maturation, as described herein can be administered together with one or more TLR agonists for therapeutic purposes.

Lipids and Liposomes

Liposomes are vesicles formed from one ("unilamellar") or more ("multilamellar") layers of phospholipid. Because of the amphipathic character of the phospholipid building blocks, liposomes typically comprise a hydrophilic layer presenting a hydrophilic external face and enclosing a hydrophilic core. The versatility of liposomes in the incorporation of hydrophilic/hydrophobic components, their non-toxic nature, biodegradability, biocompatibility, adjuvanticity, induction of cellular immunity, property of sustained release and prompt uptake by macrophages, makes them attractive candidates for the delivery of antigens.

WO2010/104833, which is incorporated by reference herein in its entirety, describes liposomal preparations which comprise:
a) an aqueous vehicle;
b) liposomes comprising
(i) dimyristoylphosphatidylcholine ("DMPC"),
(ii) dimyristoylphosphatidylglycerol ("DMPG"), dimyristoyltrimethylammonium propane ("DMTAP"), or both DMPG and DMTAP,
and
(iii) at least one sterol derivative; and
c) one or more immunogenic polypeptide(s) or carbohydrate(s) covalently linked to between 1% and 100% of said at least one sterol derivative.

Such liposomal formulations, referred to herein as VesiVax® (Molecular Express, Inc.), with our without the "immunogenic polypeptide(s) or carbohydrate(s)" referred to above, can contain one or more additional components such as peptidoglycan, lipopeptide, lipopolysaccharide, monophosphoryl lipid A, lipoteichoic acid, resiquimod, imiquimod, flagellin, oligonucleotides containing unmethylated CpG motifs, beta-galactosylceramide, muramyl dipeptide, all-trans retinoic acid, double-stranded viral RNA, heat shock proteins, dioctadecyldimethylammonium bromide, cationic surfactants, toll-like receptor agonists, dimyristoyl-trimethylammoniumpropane, and nod-like receptor agonists. Advantageously, these liposomal formulations can be used to deliver one or more cyclic purine dinucleotides in accordance with the present invention.

Moreover, while the liposomal formulations discussed above employ a "steroid derivative" as an anchor for attaching an immunogenic polypeptide or carbohydrate to a liposome, the steroid may simply be provided as an unconjugated steroid such as cholesterol.

Suitable methods for preparing liposomes from lipid mixtures are well known in the art. See, e.g., Basu & Basu, *Liposome Methods and Protocols* (*Methods in Molecular Biology*), Humana Press, 2002; Gregoriadis, *Liposome Technology*, 3$^{rd}$ *Edition*, Informa HealthCare, 2006. Preferred methods include extrusion, homogenization, and sonication methods described therein. An exemplary method for preparing liposomes for use in the present invention, which comprises drying a lipid mixture, followed by hydration in an aqueous vehicle and sonication to form liposomes, is described in WO2010/104833.

In certain embodiments, the liposomes are provided within a particular average size range. Liposome size can be selected, for example, by extrusion of an aqueous vehicle comprising liposomes through membranes having a preselected pore size and collecting the material flowing through the membrane. In preferred embodiments, the liposomes are selected to be substantially between 50 and 500 nm in diameter, more preferably substantially between 50 and 200 nm in diameter, and most preferably substantially between 50 and 150 nm in diameter. The term "substantially" as used herein in this context means that at least 75%, more preferably 80%, and most preferably at least 90% of the liposomes are within the designated range.

Other lipid and lipid-like adjuvants which may find use in the present invention include oil-in-water (o/w) emulsions (see, e.g., Muderhwa et al., J. Pharmaceut. Sci. 88: 1332-9, 1999)), VesiVax® TLR (Molecular Express, Inc.), digitonin (see, e.g., U.S. Pat. No. 5,698,432), and glucopyranosyl lipids (see, e.g., United States Patent Application 20100310602).

Chemotherapeutic Agents

In additional embodiments the methods further involve administering to the subject an effective amount of one or more chemotherapeutics as an additional treatment. In certain embodiments the one or more chemotherapeutics is selected from abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-t-butylamide, cachectin, cemadotin, chlorambucil, cyclophosphamide, 3',4'-didehydro-4'-deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, onapristone, paclitaxel, prednimustine, procarbazine, RPR109881, stramustine phosphate, tamoxifen, tasonermin, taxol, tretinoin, vinblastine, vincristine, vindesine sulfate, and vinflunine.

Immunomodulatory Cell Lines

By "inactivated tumor cell" is meant a tumor cell (either "autologous" or "allogeneic" to the patient) which has which been treated to prevent division of the cells. For purposes of the present invention, such cells preserve their immunogenicity and their metabolic activity. Such tumor cells are genetically modified to express a transgene which is expressed within a patient as part of cancer therapy. Thus, a composition or vaccine of the invention comprises neoplastic (e.g., tumor) cells that are autologous or allogeneic to the patient undergoing treatment and is most preferably the same general type of tumor cell as is afflicting the patient. For example, a patient suffering from melanoma will typically be administered a genetically modified cell derived from a melanoma. Methods for inactivating tumor cells for use in the present invention, such as the use of irradiation, are well known in the art.

The inactivated tumor cells of the present invention are administered to the patient together with one or more costimulatory molecules or agents. A preferred costimulatory agent comprises one or more cytokines which stimulate dendritic cell induction, recruitment, and/or maturation. Methods for assessing such costimulatory agents are well known in the literature. Induction and maturation of DCs is typically assessed by increased expression of certain membrane molecules such as CD80 and CD86, and/or secretion of pro-inflammatory cytokines, such as IL-12 and type I interferons following stimulation.

In preferred embodiments, the inactivated tumor cells themselves are modified to express and secrete one or more cytokines which stimulate dendritic cell induction, recruitment, and/or maturation. The present invention is described in exemplary terms with regard to the use of GM-CSF. Thus, by way of example, the tumor cell may express a transgene encoding GM-CSF as described in U.S. Pat. Nos. 5,637,483, 5,904,920, 6,277,368 and 6,350,445, as well as in US Patent Publication No. 20100150946, each of which is expressly incorporated by reference herein. A form of GM-CSF-expressing genetically modified cancer cells or a "cytokine-expressing cellular vaccine" for the treatment of pancreatic cancer is described in U.S. Pat. Nos. 6,033,674 and 5,985,290, both of which are expressly incorporated by reference herein.

Other suitable cytokines which may be expressed by such inactivated tumor cells and/or bystander cells instead of, or together with, GM-CSF include, but are not limited to, one or more of CD40 ligand, IL-12, CCL3, CCL20, and CCL21. This list is not meant to be limiting.

While it is preferred that the inactivated tumor cells administered to the subject express one or more cytokines of interest, the tumor cell line may be accompanied by an inactivated bystander cell line which expresses and secretes one or more cytokines which stimulate dendritic cell induction, recruitment, and/or maturation. The bystander cell line may provide all of the cytokines which stimulate dendritic cell induction, recruitment, and/or maturation, or may supplement cytokines which stimulate dendritic cell induction, recruitment, and/or maturation expressed and secreted by the inactivated tumor cells. By way of example, immunomodulatory cytokine-expressing bystander cell lines are disclosed in U.S. Pat. Nos. 6,464,973, and 8,012,469, Dessureault et al., Ann. Surg. Oncol. 14: 869-84, 2007, and Eager and Nemunaitis, Mol. Ther. 12: 18-27, 2005, each of which is expressly incorporated by reference herein.

By "Granulocyte-macrophage colony stimulating factor (GM-CSF) polypeptide" is meant a cytokine or fragment thereof having immunomodulatory activity and having at least about 85% amino acid sequence identity to GenBank Accession No. AAA52122.1.

Vaccines

In certain embodiments, the CDN compositions are administered in conjunction with one or more vaccines intended to stimulate an immune response to one or more predetermined antigens. Examples of target antigens that may find use in the invention are listed in the following table. The target antigen may also be a fragment or fusion polypeptide comprising an immunologically active portion of the antigens listed in the table. This list is not meant to be limiting.

TABLE 1

Antigens.

| Antigen | Reference |
|---|---|
| Tumor antigens | |
| Mesothelin | GenBank Acc. No. NM_005823; U40434; NM_013404; BC003512 (see also, e.g., Hassan, et al. (2004) Clin. Cancer Res. 10: 3937-3942; Muminova, et al. (2004) BMC Cancer 4: 19; Iacobuzio-Donahue, et al. (2003) Cancer Res. 63: 8614-8622). |

TABLE 1-continued

Antigens.

| Antigen | Reference |
|---|---|
| Wilms' tumor-1 associated protein (Wt-1), including isoform A; isoform B; isoform C; isoform D. | WT-1 isoform A (GenBank Acc. Nos. NM_000378; NP_000369). WT-1 isoform B (GenBank Acc. Nos. NM_024424; NP_077742). WT-1 isoform C (GenBank Acc. Nos. NM_024425; NP_077743). WT-1 isoform D (GenBank Acc. Nos. NM_024426; NP_077744). |
| Stratum corneum chymotryptic enzyme (SCCE), and variants thereof. | GenBank Acc. No. NM_005046; NM_139277; AF332583. See also, e.g., Bondurant, et al. (2005) Clin. Cancer Res. 11: 3446-3454; Santin, et al. (2004) Gynecol. Oncol. 94: 283-288; Shigemasa, et al. (2001) Int. J. Gynecol. Cancer 11: 454-461; Sepehr, et al. (2001) Oncogene 20: 7368-7374. |
| MHC class I chain-related protein A (MICA); MHC class I chain-related protein A (MICB). | See, e.g., Groh, et al. (2005) Proc. Natl. Acad. Sci. USA 102: 6461-6466; GenBank Acc. Nos. NM_000247; BC_016929; AY750850; NM_005931. |
| Gastrin and peptides derived from gastrin; gastrin/CCK-2 receptor (also known as CCK-B). | Harris, et al. (2004) Cancer Res. 64: 5624-5631; Gilliam, et al. (2004) Eur. J. Surg. Oncol. 30: 536-543; Laheru and Jaffee (2005) Nature Reviews Cancer 5: 459-467. |
| Glypican-3 (an antigen of, e.g., hepatocellular carcinoma and melanoma). | GenBank Acc. No. NM_004484. Nakatsura, et al. (2003) Biochem. Biophys. Res. Commun. 306: 16-25; Capurro, et al. (2003) Gasteroenterol. 125: 89-97; Nakatsura, et al. (2004) Clin. Cancer Res. 10: 6612-6621. |
| Coactosin-like protein. | Nakatsura, et al. (2002) Eur. J. Immunol. 32: 826-836; Laheru and Jaffee (2005) Nature Reviews Cancer 5: 459-467. |
| Prostate stem cell antigen (PSCA). | GenBank Acc. No. AF043498; AR026974; AR302232 (see also, e.g., Argani, et al. (2001) Cancer Res. 61: 4320-4324; Christiansen, et al. (2003) Prostate 55: 9-19; Fuessel, et al. (2003) 23: 221-228). |
| Prostate acid phosphatase (PAP); prostate-specific antigen (PSA); PSM; PSMA. | Small, et al. (2000) J. Clin. Oncol. 18: 3894-3903; Altwein and Luboldt (1999) Urol. Int. 63: 62-71; Chan, et al. (1999) Prostate 41: 99-109; Ito, et al. (2005) Cancer 103: 242-250; Schmittgen, et al. (2003) Int. J. Cancer 107: 323-329; Millon, et al. (1999) Eur. Urol. 36: 278-285. |
| Six-transmembrane epithelial antigen of prostate (STEAP). | See, e.g., Machlenkin, et al. (2005) Cancer Res. 65: 6435-6442; GenBank Acc. No. NM_018234; NM_001008410; NM_182915; NM_024636; NM_012449; BC011802. |
| Prostate carcinoma tumor antigen-1 (PCTA-1). | See, e.g., Machlenkin, et al. (2005) Cancer Res. 65: 6435-6442; GenBank Acc. No. L78132. |
| Prostate tumor-inducing gene-1 (PTI-1). | See, e.g., Machlenkin, et al. (2005) Cancer Res. 65: 6435-6442). |
| Prostate-specific gene with homology to G protein-coupled receptor. | See, e.g., Machlenkin, et al. (2005) Cancer Res. 65: 6435-6442). |
| Prostase (an antrogen regulated serine protease). | See, e.g., Machlenkin, et al. (2005) Cancer Res. 65: 6435-6442; GenBank Acc. No. BC096178; BC096176; BC096175. |
| Proteinase 3. | GenBank Acc. No. X55668. |
| Cancer-testis antigens, e.g., NY-ESO-1; SCP-1; SSX-1; SSX-2; SSX-4; GAGE, CT7; CT8; CT10; MAGE-1; MAGE-2; MAGE-3; MAGE-4; MAGE-6; LAGE-1. | GenBank Acc. No. NM_001327 (NY-ESO-1) (see also, e.g., Li, et al. (2005) Clin. Cancer Res. 11: 1809-1814; Chen, et al. (2004) Proc. Natl. Acad. Sci. USA. 101(25): 9363-9368; Kubuschok, et al. (2004) Int. J. Cancer. 109: 568-575; Scanlan, et al. (2004) Cancer Immun. 4: 1; Scanlan, et al. (2002) Cancer Res. 62: 4041-4047; Scanlan, et al. (2000) Cancer Lett. 150: 155-164; Dalerba, et al. (2001) Int. J. Cancer 93: 85-90; Ries, et al. (2005) Int. J. Oncol. 26: 817-824. |
| MAGE-A1, MAGE-A2; MAGE-A3; MAGE-A4; MAGE-A6; MAGE-A9; MAGE-A10; MAGE-A12; GAGE-3/6; NT-SAR-35; BAGE; CA125. | Otte, et al. (2001) Cancer Res. 61: 6682-6687; Lee, et al. (2003) Proc. Natl. Acad. Sci. USA 100: 2651-2656; Sarcevic, et al. (2003) Oncology 64: 443-449; Lin, et al. (2004) Clin. Cancer Res. 10: 5708-5716. |
| GAGE-1; GAGE-2; GAGE-3; GAGE-4; GAGE-5; GAGE-6; GAGE-7; GAGE-8; GAGE-65; GAGE-11; GAGE-13; GAGE-7B. | De Backer, et al. (1999) Cancer Res. 59: 3157-3165; Scarcella, et al. (1999) Clin. Cancer Res. 5: 335-341. |

TABLE 1-continued

Antigens.

| Antigen | Reference |
|---|---|
| HIP1R; LMNA; KIAA1416; Seb4D; KNSL6; TRIP4; MBD2; HCAC5; MAGEA3. | Scanlan, et al. (2002) Cancer Res. 62: 4041-4047. |
| DAM family of genes, e.g., DAM-1; DAM-6. | Fleishhauer, et al. (1998) Cancer Res. 58: 2969-2972. |
| RCAS1. | Enjoji, et al. (2004) Dig. Dis. Sci. 49: 1654-1656. |
| RU2. | Van Den Eynde, et al. (1999) J. Exp. Med. 190: 1793-1800. |
| CAMEL. | Slager, et al. (2004) J. Immunol. 172: 5095-5102; Slager, et al. (2004) Cancer Gene Ther. 11: 227-236. |
| Colon cancer associated antigens, e.g., NY-CO-8; NY-CO-9; NY-CO-13; NY-CO-16; NY-CO-20; NY-CO-38; NY-CO-45; NY-CO-9/HDAC5; NY-CO-41/MBD2; NY-CO-42/TRIP4; NY-CO-95/KIAA1416; KNSL6; seb4D. | Scanlan, et al. (2002) Cancer Res. 62: 4041-4047. |
| N-Acetylglucosaminyl-tranferase V (GnT-V). | Dosaka-Akita, et al. (2004) Clin. Cancer Res. 10: 1773-1779. |
| Elongation factor 2 mutated (ELF2M). | Renkvist, et al. (2001) Cancer Immunol Immunother. 50: 3-15. |
| HOM-MEL-40/SSX2 | Neumann, et al. (2004) Int. J. Cancer 112: 661-668; Scanlan, et al. (2000) Cancer Lett. 150: 155-164. |
| BRDT. | Scanlan, et al. (2000) Cancer Lett. 150: 155-164. |
| SAGE; HAGE. | Sasaki, et al. (2003) Eur. J. Surg. Oncol. 29: 900-903. |
| RAGE. | See, e.g., Li, et al. (2004) Am. J. Pathol. 164: 1389-1397; Shirasawa, et al. (2004) Genes to Cells 9: 165-174. |
| MUM-1 (melanoma ubiquitous mutated); MUM-2; MUM-2 Arg-Gly mutation; MUM-3. | Gueguen, et al. (1998) J. Immunol. 160: 6188-6194; Hirose, et al. (2005) Int. J. Hematol. 81: 48-57; Baurain, et al. (2000) J. Immunol. 164: 6057-6066; Chiari, et al. (1999) Cancer Res. 59: 5785-5792. |
| LDLR/FUT fusion protein antigen of melanoma. | Wang, et al. (1999) J. Exp. Med. 189: 1659-1667. |
| NY-REN series of renal cancer antigens. | Scanlan, et al. (2002) Cancer Res. 62: 4041-4047; Scanlan, et al. (1999) Cancer Res. 83: 456-464. |
| NY-BR series of breast cancer antigens, e.g., NY-BR-62; NY-BR-75; NY-BR-85; NY-BR-62; NY-BR-85. | Scanlan, et al. (2002) Cancer Res. 62: 4041-4047; Scanlan, et al. (2001) Cancer Immunity 1: 4. |
| BRCA-1; BRCA-2. | Stolier, et al. (2004) Breast J. 10: 475-480; Nicoletto, et al. (2001) Cancer Treat Rev. 27: 295-304. |
| DEK/CAN fusion protein. | Von Lindern, et al. (1992) Mol. Cell. Biol. 12: 1687-1697. |
| Ras, e.g., wild type ras, ras with mutations at codon 12, 13, 59, or 61, e.g., mutations G12C; G12D; G12R; G12S; G12V; G13D; A59T; Q61H. K-RAS; H-RAS; N-RAS. | GenBank Acc. Nos. P01112; P01116; M54969; M54968; P01111; P01112; K00654. See also, e.g., GenBank Acc. Nos. M26261; M34904; K01519; K01520; BC006499; NM_006270; NM_002890; NM_004985; NM_033360; NM_176795; NM_005343. |
| BRAF (an isoform of RAF). | Tannapfel, et al. (2005) Am. J. Clin. Pathol. 123: 256-2601; Tsao and Sober (2005) Dermatol. Clin. 23: 323-333. |
| Melanoma antigens, including HST-2 melanoma cell antigens. | GenBank Acc. No. NM_206956; NM_206955; NM_206954; NM_206953; NM_006115; NM_005367; NM_004988; AY148486; U10340; U10339; M77481. See, e g., Suzuki, et al. (1999) J. Immunol. 163: 2783-2791. |
| Survivin | GenBank Acc. No. AB028869; U75285 (see also, e.g., Tsuruma, et al. (2004) J. Translational Med. 2: 19 (11 pages); Pisarev, et al. (2003) Clin. Cancer Res. 9: 6523-6533; Siegel, et al. (2003) Br. J. Haematol. 122: 911-914; Andersen, et al. (2002) Histol. Histopathol. 17: 669-675). |
| MDM-2 | NM_002392; NM_006878 (see also, e.g., Mayo, et al. (1997) Cancer Res. 57: 5013-5016; Demidenko and Blagosklonny (2004) Cancer Res. 64: 3653-3660). |
| Methyl-CpG-binding proteins (MeCP2; MBD2). | Muller, et al. (2003) Br. J. Cancer 89: 1934-1939; Fang, et al. (2004) World J. Gastroenterol. 10: 3394-3398. |

TABLE 1-continued

Antigens.

| Antigen | Reference |
|---|---|
| NA88-A. | Moreau-Aubry, et al. (2000) J. Exp. Med. 191: 1617-1624. |
| Histone deacetylases (HDAC), e.g., HDAC5. | Waltregny, et al. (2004) Eur. J. Histochem. 48: 273-290; Scanlan, et al. (2002) Cancer Res. 62: 4041-4047. |
| Cyclophilin B (Cyp-B). | Tamura, et al. (2001) Jpn. J. Cancer Res. 92: 762-767. |
| CA 15-3; CA 27.29. | Clinton, et al. (2003) Biomed. Sci. Instrum. 39: 408-414. |
| Heat shock protein Hsp70. | Faure, et al. (2004) Int. J. Cancer 108: 863-870. |
| GAGE/PAGE family, e.g., PAGE-1; PAGE-2; PAGE-3; PAGE-4; XAGE-1; XAGE-2; XAGE-3. | Brinkmann, et al. (1999) Cancer Res. 59: 1445-1448. |
| MAGE-A, B, C, and D families. MAGE-B5; MAGE-B6; MAGE-C2; MAGE-C3; MAGE-3; MAGE-6. | Lucas, et al. (2000) Int. J. Cancer 87: 55-60; Scanlan, et al. (2001) Cancer Immun. 1: 4. |
| Kinesin 2; TATA element modulatory factor 1; tumor protein D53; NY | Scanlan, et al. (2001) Cancer Immun. 30: 1-4. |
| Alpha-fetoprotein (AFP) | Grimm, et al. (2000) Gastroenterol. 119: 1104-1112. |
| SART1; SART2; SART3; ART4. | Kumamuru, et al. (2004) Int. J. Cancer 108: 686-695; Sasatomi, et al. (2002) Cancer 94: 1636-1641; Matsumoto, et al. (1998) Jpn. J. Cancer Res. 89: 1292-1295; Tanaka, et al. (2000) Jpn. J. Cancer Res. 91: 1177-1184. |
| Preferentially expressed antigen of melanoma (PRAME). | Matsushita, et al. (2003) Leuk. Lymphoma 44: 439-444; Oberthuer, et al. (2004) Clin. Cancer Res. 10: 4307-4313. |
| Carcinoembryonic antigen (CEA), CAP1-6D enhancer agonist peptide. | GenBank Acc. No. M29540; E03352; X98311; M17303 (see also, e.g., Zaremba (1997) Cancer Res. 57: 4570-4577; Sarobe, et al. (2004) Curr. Cancer Drug Targets 4: 443-454; Tsang, et al. (1997) Clin. Cancer Res. 3: 2439-2449; Fong, et al. (2001) Proc. Natl. Acad. Sci. USA 98: 8809-8814). |
| HER-2/neu. | Disis, et al. (2004) J. Clin. Immunol. 24: 571-578; Disis and Cheever (1997) Adv. Cancer Res. 71: 343-371. |
| Cdk4; cdk6; p16 (INK4); Rb protein. | Ghazizadeh, et al. (2005) Respiration 72: 68-73; Ericson, et al. (2003) Mol. Cancer Res. 1: 654-664. |
| TEL; AML1; TEL/AML1. | Stams, et al. (2005) Clin. Cancer Res. 11: 2974-2980. |
| Telomerase (TERT). | Nair, et al. (2000) Nat. Med. 6: 1011-1017. |
| 707-AP. | Takahashi, et al. (1997) Clin. Cancer Res. 3: 1363-1370. |
| Annexin, e.g., Annexin II. | Zimmerman, et al. (2004) Virchows Arch. 445: 368-374. |
| BCR/ABL; BCR/ABL p210; BCR/ABL p190; CML-66; CML-28. BCL2; BLC6; CD10 protein. | Cobaldda, et al. (2000) Blood 95: 1007-1013; Hakansson, et al. (2004) Leukemia 18: 538-547; Schwartz, et al. (2003) Semin. Hematol. 40: 87-96; Lim, et al. (1999) Int. J. Mol. Med. 4: 665-667. Iqbal, et al. (2004) Am. J. Pathol. 165: 159-166. |
| CDC27 (this is a melanoma antigen). | Wang, et al. (1999) Science 284: 1351-1354. |
| Sperm protein 17 (SP17); 14-3-3-zeta; MEMD; KIAA0471; TC21. | Arora, et al. (2005) Mol. Carcinog. 42: 97-108. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Gp100/pmel-17. | GenBank Acc. Nos. AH003567; U31798; U31799; U31807; U31799 (see also, e.g., Bronte, et al. (2000) Cancer Res. 60: 253-258). |
| TARP. | See, e.g., Clifton, et al. (2004) Proc. Natl. Acad. Sci. USA 101: 10166-10171; Virok, et al. (2005) Infection Immunity 73: 1939-1946. |
| Tyrosinase-related proteins 1 and 2 (TRP-1 and TRP-2). | GenBank Acc. No. NM_001922. (see also, e.g., Bronte, et al. (2000) Cancer Res. 60: 253-258). |
| Melanocortin 1 receptor (MC1R); MAGE-3; gp100; tyrosinase; dopachrome tautomerase (TRP-2); MART-1. | Salazar-Onfray, et al. (1997) Cancer Res. 57: 4348-4355; Reynolds, et al. (1998) J. Immunol. 161: 6970-6976; Chang, et al. (2002) Clin. Cancer Res. 8: 1021-1032. |
| MUC-1; MUC-2. | See, e.g., Davies, et al. (1994) Cancer Lett. 82: 179-184; Gambus, et al. (1995) Int. J. Cancer 60: 146-148; McCool, et al. (1999) Biochem. J. 341: 593-600. |

TABLE 1-continued

Antigens.

| Antigen | Reference |
|---|---|
| Spas-1. | U.S. Published Pat. Appl. No. 20020150588 of Allison, et al. |
| CASP-8; FLICE; MACH. | Mandruzzato, et al. (1997) J. Exp. Med. 186: 785-793. |
| CEACAM6; CAP-1. | Duxbury, et al. (2004) Biochem. Biophys. Res. Commun. 317: 837-843; Morse, et al. (1999) Clin. Cancer Res. 5: 1331-1338. |
| HMGB1 (a DNA binding protein and cytokine). | Brezniceanu, et al. (2003) FASEB J. 17: 1295-1297. |
| ETV6/AML1. | Codrington, et al. (2000) Br. J. Haematol. 111: 1071-1079. |
| Mutant and wild type forms of adenomatous polyposis coli (APC); beta-catenin; c-met; p53; E-cadherin; cyclooxygenase-2 (COX-2). | Clements, et al. (2003) Clin. Colorectal Cancer 3: 113-120; Gulmann, et al. (2003) Appl. Immunohistochem. Mol. Morphol. 11: 230-237; Jungck, et al. (2004) Int. J. Colorectal. Dis. 19: 438-445; Wang, et al. (2004) J. Surg. Res. 120: 242-248; Abutaily, et al. (2003) J. Pathol. 201: 355-362; Liang, et al. (2004) Br. J. Surg. 91: 355-361; Shirakawa, et al. (2004) Clin. Cancer Res. 10: 4342-4348. |
| Renal cell carcinoma antigen bound by mAB G250. | Mulders, et al. (2003) Urol. Clin. North Am. 30: 455-465; Steffens, et al. (1999) Anticancer Res. 19: 1197-1200. |
| EphA2 | See, e.g., U.S. Patent Publication No. 2005/0281783 A1; Genbank Accession No. NM_004431 (human); Genbank Accession No. NM_010139 (Mouse); Genbank Accession No. AB038986 (Chicken, partial sequence); GenBank Accession Nos. NP_004422, AAH37166, and AAA53375 (human); GenBank Accession Nos. NP_034269 (mouse), AAH06954 (mouse), XP_345597 (rat), and BAB63910 (chicken). |
| EGFRvIII | See, e.g., WO/2012/068360 |

*Francisella tularensis* antigens

| | |
|---|---|
| *Francisella tularensis* A and B. | Complete genome of subspecies Schu S4 (GenBank Acc. No. AJ749949); of subspecies Schu 4 (GenBank Acc. No. NC_006570). Outer membrane protein (43 kDa) Bevanger, et al. (1988) J. Clin. Microbiol. 27: 922-926; Porsch-Ozcurumez, et al. (2004) Clin. Diagnostic. Lab. Immunol. 11: 1008-1015). Antigenic components of *F. tularensis* include, e.g., 80 antigens, including 10 kDa and 60 kDa chaperonins (Havlasova, et al. (2002) Proteomics 2: 857-86), nucleoside diphosphate kinase, isocitrate dehydrogenase, RNA-binding protein Hfq, the chaperone ClpB (Havlasova, et al. (2005) Proteomics 5: 2090-2103). See also, e.g., Oyston and Quarry (2005) Antonie Van Leeuwenhoek 87: 277-281; Isherwood, et al. (2005) Adv. Drug Deliv. Rev. 57: 1403-1414; Biagini, et al. (2005) Anal. Bioanal. Chem. 382: 1027-1034. |

Malarial antigens

| | |
|---|---|
| Circumsporozoite protein (CSP); SSP2; HEP17; Exp-1 orthologs found in *P. falciparum*; and LSA-1. | See, e.g., Haddad, et al. (2004) Infection Immunity 72: 1594-1602; Hoffman, et al. (1997) Vaccine 15: 842-845; Oliveira-Ferreira and Daniel-Ribeiro (2001) Mem. Inst. Oswaldo Cruz, Rio de Janeiro 96: 221-227. CSP (see, e.g., GenBank Acc. No. AB121024). SSP2 (see, e.g., GenBank Acc. No. AF249739). LSA-1 (see, e.g., GenBank Acc. No. Z30319). |
| Ring-infected erythrocyte survace protein (RESA); merozoite surface protein 2 (MSP2); Spf66; merozoite surface protein 1(MSP1); 195A; BVp42. | See, e.g., Stirnadel, et al. (2000) Int. J. Epidemiol. 29: 579-586; Krzych, et al. (1995) J. Immunol. 155: 4072-4077. See also, Good, et al. (2004) Immunol. Rev. 201: 254-267; Good, et al. (2004) Ann. Rev. Immunol. 23: 69-99. MSP2 (see, e.g., GenBank Acc. No. X96399; X96397). MSP1 (see, e.g., GenBank Acc. No. X03371). RESA (see, e.g., GenBank Acc. No. X05181; X05182). |
| Apical membrane antigen 1 (AMA1). | See, e.g., Gupta, et al. (2005) Protein Expr. Purif. 41: 186-198. AMA1 (see, e.g., GenBank Acc. No. A'13; AJ494905; AJ490565). |

Viruses and viral antigens

| | |
|---|---|
| Hepatitis A | GenBank Acc. Nos., e.g., NC_001489; AY644670; X83302; K02990; M14707. |
| Hepatitis B | Complete genome (see, e.g., GenBank Acc. Nos. AB214516; NC_003977; AB205192; AB205191; AB205190; AJ748098; AB198079; AB198078; AB198076; AB074756). |
| Hepatitis C | Complete genome (see, e.g., GenBank Acc. Nos. NC_004102; AJ238800; AJ238799; AJ132997; AJ132996; AJ000009; D84263). |
| Hepatitis D | GenBank Acc. Nos, e.g. NC_001653; AB118847; AY261457. |
| Human papillomavirus, including all 200+ subtypes (classed in 16 groups), such as the | See, e.g., Trimble, et al. (2003) Vaccine 21: 4036-4042; Kim, et al. (2004) Gene Ther. 11: 1011-1018; Simon, et al. (2003) Eur. J. Obstet. Gynecol. Reprod. Biol. 109: 219-223; Jung, et al. (2004) J. Microbiol. 42: 255-266; Damasus-Awatai and Freeman-Wang (2003) Curr. Opin. |

TABLE 1-continued

Antigens.

| Antigen | Reference |
| --- | --- |
| high risk subtypes 16, 18, 30, 31, 33, 45. | Obstet. Gynecol. 15: 473-477; Jansen and Shaw (2004) Annu. Rev. Med. 55: 319-331; Roden and Wu (2003) Expert Rev. Vaccines 2: 495-516; de Villiers, et al. (2004) Virology 324: 17-24; Hussain and Paterson (2005) Cancer Immunol. Immunother. 54: 577-586; Molijn, et al. (2005) J. Clin. Virol. 32 (Suppl. 1) S43-S51. GenBank Acc. Nos. AY686584; AY686583; AY686582; NC_006169; NC_006168; NC_006164; NC_001355; NC_001349; NC_005351; NC_001596). |
| Human T-cell lymphotropic virus (HTLV) types I and II, including the HTLV type I subtypes Cosmopolitan, Central African, and Austro-Melanesian, and the HTLV type II subtypes Iia, Iib, Iic, and Iid. | See, e.g., Capdepont, et al. (2005) AIDS Res. Hum. Retrovirus 21: 28-42; Bhigjee, et al. (1999) AIDS Res. Hum. Restrovirus 15: 1229-1233; Vandamme, et al. (1998) J. Virol. 72: 4327-4340; Vallejo, et al. (1996) J. Acquir. Immune Defic. Syndr. Hum. Retrovirol. 13: 384-391. HTLV type I (see, e.g., GenBank Acc. Nos. AY563954; AY563953. HTLV type II (see, e.g., GenBank Acc. Nos. L03561; Y13051; AF139382). |
| Coronaviridae, including Coronaviruses, such as SARS-coronavirus (SARS-CoV), and Toroviruses. | See, e.g., Brian and Baric (2005) Curr. Top. Microbiol. Immunol. 287: 1-30; Gonzalez, et al. (2003) Arch. Virol. 148: 2207-2235; Smits, et al. (2003) J. Virol. 77: 9567-9577; Jamieson, et al. (1998) J. Infect. Dis. 178: 1263-1269 (GenBank Acc. Nos. AY348314; NC_004718; AY394850). |
| Rubella virus. | GenBank Acc. Nos. NC_001545; AF435866. |
| Mumps virus, including the genotypes A, C, D, G, H, and I. | See, e.g., Orvell, eta 1. (2002) J. Gen. Virol. 83: 2489-2496. See, e.g., GenBank Acc. Nos. AY681495; NC_002200; AY685921; AF201473. |
| Coxsackie virus A including the serotypes 1, 11, 13, 15, 17, 18, 19, 20, 21, 22, and 24 (also known as Human enterovirus C; HEV-C). | See, e.g., Brown, et al. (2003) J. Virol. 77: 8973-8984. GenBank Acc. Nos. AY421768; AY790926: X67706. |
| Coxsackie virus B, including subtypes 1-6. | See, e.g., Ahn, et al. (2005) J. Med. Virol. 75: 290-294; Patel, et al. (2004) J. Virol. Methods 120: 167-172; Rezig, et al. (2004) J. Med. Virol. 72: 268-274. GenBank Acc. No. X05690. |
| Human enteroviruses including, e.g., human enterovirus A (HEV-A, CAV2 to CAV8, CAV10, CAV12, CAV14, CAV16, and EV71) and also including HEV-B (CAV9, CBV1 to CBV6, E1 to E7, E9, E11 to E21, E24 to E27, E29 to E33, and EV69 and E73), as well as HEV. | See, e.g., Oberste, et al. (2004) J. Virol. 78: 855-867. Human enterovirus A (GenBank Acc. Nos. NC_001612); human enterovirus B (NC_001472); human enterovirus C (NC_001428); human enterovirus D (NC_001430). Simian enterovirus A (GenBank Acc. No. NC_003988). |
| Polioviruses including PV1, PV2, and PV3. | See, e.g., He, et al. (2003) J. Virol. 77: 4827-4835; Hahsido, et al. (1999) Microbiol. Immunol. 43: 73-77. GenBank Acc. No. AJ132961 (type 1); AY278550 (type 2); X04468 (type 3). |
| Viral encephalitides viruses, including equine encephalitis, Venezuelan equine encephalitis (VEE) (including subtypes IA, IB, IC, ID, IIIC, IIID), Eastern equine encephalitis (EEE), Western equine encephalitis (WEE), St. Louis encephalitis, Murray Valley (Australian) encephalitis, Japanese encephalitis, and tick-born encephalitis. | See, e.g., Hoke (2005) Mil. Med. 170: 92-105; Estrada-Franco, et al. (2004) Emerg. Infect. Dis. 10: 2113-2121; Das, et al. (2004) Antiviral Res. 64: 85-92; Aguilar, et al. (2004) Emerg. Infect. Dis. 10: 880-888; Weaver, et al. (2004) Arch. Virol. Suppl. 18: 43-64; Weaver, et al. (2004) Annu. Rev. Entomol. 49: 141-174. Eastern equine encephalitis (GenBank Acc. No. NC_003899; AY722102); Western equine encephalitis (NC_003908). |

TABLE 1-continued

Antigens.

| Antigen | Reference |
|---|---|
| Human herpesviruses, including cytomegalovirus (CMV), Epstein-Barr virus (EBV), human herpesvirus-1 (HHV-1), HHV-2, HHV-3, HHV-4, HHV-5, HHV-6, HHV-7, HHV-8, herpes B virus, herpes simplex virus types 1 and 2 (HSV-1, HSV-2), and varicella zoster virus (VZV). | See, e.g., Studahl, et al. (2000) Scand. J. Infect. Dis. 32: 237-248; Padilla, et al. (2003) J. Med. Virol. 70 (Suppl. 1) S103-S110; Jainkittivong and Langlais (1998) Oral Surg. Oral Med. 85: 399-403. GenBank Nos. NC_001806 (herpesvirus 1); NC_001798 (herpesvirus 2); X04370 and NC_001348 (herpesvirus 3); NC_001345 (herpesvirus 4); NC_001347 (herpesvirus 5); X83413 and NC_000898 (herpesvirus 6); NC_001716 (herpesvirus 7). Human herpesviruses types 6 and 7 (HHV-6; HHV-7) are disclosed by, e.g., Padilla, et al. (2003) J. Med. Virol. 70 (Suppl. 1)S103-S110. Human herpesvirus 8 (HHV-8), including subtypes A-E, are disclosed in, e.g., Treurnicht, et al. (2002) J. Med. Virul. 66: 235-240. |
| HIV-1 including group M (including subtypes A to J) and group O (including any distinguishable subtypes) (HIV-2, including subtypes A-E. | See, e.g., Smith, et al. (1998) J. Med. Virol. 56: 264-268. See also, e.g., GenBank Acc. Nos. DQ054367; NC_001802; AY968312; DQ011180; DQ011179; DQ011178; DQ011177; AY588971; AY588970; AY781127; AY781126; AY970950; AY970949; AY970948; X61240; AJ006287; AJ508597; and AJ508596. |
| Epstein-Barr virus (EBV), including subtypes A and B. | See, e.g., Peh, et al. (2002) Pathology 34: 446-450. Epstein-Barr virus strain B95-8 (GenBank Acc. No. V01555). |
| Reovirus, including serotypes and strains 1, 2, and 3, type 1 Lang, type 2 Jones, and type 3 Dearing. | See, e.g., Barthold, et al. (1993) Lab. Anim. Sci. 43: 425-430; Roner, et al. (1995) Proc. Natl. Acad. Sci. USA 92: 12362-12366; Kedl, et al. (1995) J. Virol. 69: 552-559. GenBank Acc. No. K02739 (sigma-3 gene surface protein). |
| Cytomegalovirus (CMV) subtypes include CMV subtypes I-VII. | See, e.g., Chern, et al. (1998) J. Infect. Dis. 178: 1149-1153; Vilas Boas, et al. (2003) J. Med. Virol. 71: 404-407; Trincado, et al. (2000) J. Med. Virol. 61: 481-487. GenBank Acc. No. X17403. |
| Rhinovirus, including all serotypes. | Human rhinovirus 2 (GenBank Acc. No. X02316); Human rhinovirus B (GenBank Acc. No. NC_001490); Human rhinovirus 89 (GenBank Acc. No. NC_001617); Human rhinovirus 39 (GenBank Acc. No. AY751783). |
| Adenovirus, including all serotypes. | AY803294; NC_004001; AC_000019; AC_000018; AC_000017; AC_000015; AC_000008; AC_000007; AC_000006; AC_000005; AY737798; AY737797; NC_003266; NC_002067; AY594256; AY594254; AY875648; AJ854486; AY163756; AY594255; AY594253; NC_001460; NC_001405; AY598970; AY458656; AY487947; NC_001454; AF534906; AY45969; AY128640; L19443; AY339865; AF532578. |
| Filoviruses, including Marburg virus and Ebola virus, and strains such as Ebola-Sudan (EBO-S), Ebola-Zaire (EBO-Z), and Ebola-Reston (EBO-R). | See, e.g., Geisbert and Jahrling (1995) Virus Res. 39: 129-150; Hutchinson, et al. (2001) J. Med. Virol. 65: 561-566. Marburg virus (see, e.g., GenBank Acc. No. NC_001608). Ebola virus (see, e.g., GenBank Acc. Nos. NC_006432; AY769362; NC_002549; AF272001; AF086833). |
| Arenaviruses, including lymphocytic choriomeningitis (LCM) virus, Lassa virus, Junin virus, and Machupo virus. | Junin virus, segment S (GenBank Acc. No. NC_005081); Junin virus, segment L (GenBank Acc. No. NC_005080). |
| Rabies virus. | See, e.g., GenBank Acc. Nos. NC_001542; AY956319; AY705373; AF499686; AB128149; AB085828; AB009663. |
| Arboviruses, including West Nile virus, Dengue viruses 1 to 4, Colorado tick fever virus, Sindbis virus, Togaviraidae, Flaviviridae, Bunyaviridae, Reoviridae, Rhabdoviridae, Orthomyxoviridae, and the like. | Dengue virus type 1 (see, e.g., GenBank Acc. Nos. AB195673; AY762084). Dengue virus type 2 (see, e.g., GenBank Acc. Nos. NC_001474; AY702040; AY702039; AY702037). Dengue virus type 3 (see, e.g., GenBank Acc. Nos. AY923865; AT858043). Dengue virus type 4 (see, e.g., GenBank Acc. Nos. AY947539; AY947539; AF326573). Sindbis virus (see, e.g., GenBank Acc. Nos. NC_001547; AF429428; J02363; AF103728). West Nile virus (see, e.g., GenBank Acc. Nos. NC_001563; AY603654). |

TABLE 1-continued

Antigens.

| Antigen | Reference |
| --- | --- |
| Poxvirus including orthopoxvirus (variola virus, monkeypox virus, vaccinia virus, cowpox virus), yatapoxvirus (tanapox virus, Yaba monkey tumor virus), parapoxvirus, and molluscipoxvirus. | Viriola virus (see, e.g., GenBank Acc. Nos. NC_001611; Y16780; X72086; X69198). |
| Yellow fever. | See, e.g., GenBank Acc. No. NC_002031; AY640589; X03700. |
| Hantaviruses, including serotypes Hantaan (HTN), Seoul (SEO), Dobrava (DOB), Sin Nombre (SN), Puumala (PUU), and Dobrava-like Saaremaa (SAAV). | See, e.g., Elgh, et al. (1997) J. Clin. Microbiol. 35: 1122-1130; Sjolander, et al. (2002) Epidemiol. Infect. 128: 99-103; Zeier, et al. (2005) Virus Genes 30: 157-180. GenBank Acc. No. NC_005222 and NC_005219 (Hantavirus). See also, e.g., GenBank Acc. Nos. NC_005218; NC_005222; NC_005219. |
| Flaviviruses, including Dengue virus, Japanese encephalitis virus, West Nile virus, and yellow fever virus. | See, e.g., Mukhopadhyay, et al. (2005) Nature Rev. Microbiol. 3: 13-22. GenBank Acc. Nos NC_001474 and AY702040 (Dengue). GenBank Acc. Nos. NC_001563 and AY603654. |
| Measles virus. | See, e.g., GenBank Acc. Nos. AB040874 and AY486084. |
| Human parainfluenzaviruses (HPV), including HPV types 1-56. | Human parainfluenza virus 2 (see, e.g., GenBank Acc. Nos. AB176531; NC003443). Human parainfluenza virus 3 (see, e.g., GenBank Acc. No. NC_001796). |
| Influenza virus, including influenza virus types A, B, and C. | Influenza nucleocapsid (see, e.g., GenBank Acc. No. AY626145). Influenza hemagglutinin (see, e.g., GenBank Acc. Nos. AY627885; AY555153). Influenza neuraminidase (see, e.g., GenBank Acc. Nos. AY555151; AY577316). Influenza matrix protein 2 (see, e.g., GenBank Acc. Nos. AY626144(. Influenza basic protein 1 (see, e.g., GenBank Acc. No. AY627897). Influenza polymerase acid protein (see, e.g., GenBank Acc. No. AY627896). Influenza nucleoprotein (see, e.g., GenBank Acc. Nno. AY627895). |
| Influenza A virus subtypes, e.g., swine viruses (SIV): H1N1 influenzaA and swine influenza virus. | Hemagglutinin of H1N1 (GenBank Acc. No. S67220). Influenza A virus matrix protein (GenBank Acc. No. AY700216). Influenza virus A H5H1 nucleoprotein (GenBank Acc. No. AY646426). H1N1 haemagglutinin (GenBank Acc. No. D00837). See also, GenBank Acc. Nos. BD006058; BD006055; BD006052. See also, e.g., Wentworth, et al. (1994) J. Virol. 68: 2051-2058; Wells, et al. (1991) J.A.M.A. 265: 478-481. |
| Respiratory syncytial virus (RSV), including subgroup A and subgroup B. | Respiratory syncytial virus (RSV) (see, e.g., GenBank Acc. Nos. AY353550; NC_001803; NC001781). |
| Rotaviruses, including human rotaviruses A to E, bovine rotavirus, rhesus monkey rotavirus, and human-RVV reassortments. | Human rotavirus C segment 8 (GenBank Acc. No. AJ549087); Human rotavirus G9 strain outer capsid protein (see, e.g., GenBank Acc. No. DQ056300); Human rotavirus B strain non-structural protein 4 (see, e.g., GenBank Acc. No. AY548957); human rotavirus A strain major inner capsid protein (see, e.g., GenBank Acc. No. AY601554). |
| Polyomavirus, including simian virus 40 (SV40), JC virus (JCV) and BK virus (BKV). | See, e.g., Engels, et al. (2004) J. Infect. Dis. 190: 2065-2069; Vilchez and Butel (2004) Clin. Microbiol. Rev. 17: 495-508; Shivapurkar, et al. (2004) Cancer Res. 64: 3757-3760; Carbone, et al. (2003) Oncogene 2: 5173-5180; Barbanti-Brodano, et al. (2004) Virology 318: 1-9) (SV40 complete genome in, e.g., GenBank Acc. Nos. NC_001669; AF168994; AY271817; AY271816; AY120890; AF345344; AF332562). |
| Coltiviruses, including Colorado tick fever virus, Eyach virus. | Attoui, et al. (1998) J. Gen. Virol. 79: 2481-2489. Segments of Eyach virus (see, e.g., GenBank Acc. Nos. AF282475; AF282472; AF282473; AF282478; AF282476; NC_003707; NC_003702; NC_003703; NC_003704; NC_003705; NC_003696; NC_003697; NC_003698; NC_003699; NC_003701; NC_003706; NC_003700; AF282471; AF282477). |
| Calciviruses, including the genogroups Norwalk, Snow Mountain group (SMA), and Saaporo. | Snow Mountain virus (see, e.g., GenBank Acc. No. AY134748). |

TABLE 1-continued

Antigens.

| Antigen | Reference |
| --- | --- |
| Parvoviridae, including dependovirus, parvovirus (including parvovirus B19), and erythrovirus. | See, e.g., Brown (2004) Dev. Biol. (Basel) 118: 71-77; Alvarez-Lafuente, et al. (2005) Ann. Rheum. Dis. 64: 780-782; Ziyaeyan, et al. (2005) Jpn. J. Infect. Dis. 58: 95-97; Kaufman, et al. (2005) Virology 332: 189-198. |

Other organisms for which suitable antigens are known in the art include, but are not limited to, *Chlamydia trachomatis*, *Streptococcus pyogenes* (Group A Strep), *Streptococcus agalactia* (Group B Strep), *Streptococcus pneumonia*, *Staphylococcus aureus*, *Escherichia coli*, *Haemophilus influenzae*, *Neisseria meningitidis*, *Neisseria gonorrheae*, *Vibrio cholerae*, *Salmonella* species (including *typhi*, *typhimurium*), enterica (including *Helicobactor pylori Shigella flexneri* and other Group D *shigella* species), *Burkholderia mallei*, *Burkholderia pseudomallei*, *Klebsiella pneumonia*, *Clostridium* species (including *C. difficile*), *Vibrio parahaemolyticus* and *V. vulnificus*. This list is not meant to be limiting.

Pharmaceutical Compositions

The term "pharmaceutical" as used herein refers to a chemical substance intended for use in the cure, treatment, or prevention of disease and which is subject to an approval process by the U.S. Food and Drug Administration (or a non-U.S. equivalent thereof) as a prescription or over-the-counter drug product. Details on techniques for formulation and administration of such compositions may be found in Remington, The Science and Practice of Pharmacy 21$^{st}$ Edition (Mack Publishing Co., Easton, Pa.) and Nielloud and Marti-Mestres, Pharmaceutical Emulsions and Suspensions: 2$^{nd}$ Edition (Marcel Dekker, Inc, New York).

For the purposes of this disclosure, the pharmaceutical compositions may be administered by a variety of means including orally, parenterally, by inhalation spray, topically, or rectally in formulations containing pharmaceutically acceptable carriers, adjuvants and vehicles. The term parenteral as used here includes but is not limited to subcutaneous, intravenous, intramuscular, intraarterial, intradermal, intrathecal and epidural injections with a variety of infusion techniques. Intraarterial and intravenous injection as used herein includes administration through catheters. Administration via intracoronary stents and intracoronary reservoirs is also contemplated. The term oral as used herein includes, but is not limited to oral ingestion, or delivery by a sublingual or buccal route. Oral administration includes fluid drinks, energy bars, as well as pill formulations.

Pharmaceutical compositions may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing a drug compound in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents; such as magnesium stearate, stearic acid or talc. Tablets may be uncoated, or may be coated by known techniques including enteric coating, colonic coating, or microencapsulation to delay disintegration and adsorption in the gastrointestinal tract and/or provide a sustained action over a longer period. For example, a time delay material such as glyceryl monostearate or glyceryl distearate alone or with a wax may be employed.

Formulations for oral use may be also presented as hard gelatin capsules where the drug compound is mixed with an inert solid diluent, for example calcium phosphate or kaolin, or as soft gelatin capsules wherein the active ingredient is mixed with water or an oil medium, such as peanut oil, liquid paraffin or olive oil.

Pharmaceutical compositions may be formulated as aqueous suspensions in admixture with excipients suitable for the manufacture of aqueous-suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

Oil suspensions may be formulated by suspending the active ingredient in a vegetable oil, such as arachis oil, olive oil, sesame oil or coconut oil, or a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the disclosure suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the disclosure may also be in the form of oil-in-water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents.

Syrups and elixirs may be formulated with sweetening agents, such as glycerol, sorbitol or sucrose. Such formulations may also contain a demulcent, a preservative, a flavoring or a coloring agent.

The pharmaceutical compositions of the disclosure may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 20 to 500 mg of active material compounded with an appropriate and convenient amount of carrier material which may vary from about 5 to about 95% of the total compositions. It is preferred that the pharmaceutical composition be prepared which provides easily measurable amounts for administration. Typically, an effective amount to be administered systemically is about 0.1 mg/kg to about 100 mg/kg and depends upon a number of factors including, for example, the age and weight of the subject (e.g., a mammal such as a human), the precise condition requiring treatment and its severity, the route of administration, and will ultimately be at the discretion of the attendant physician or veterinarian. It will be understood, however, that the specific dose level for any particular patient will depend on a variety of factors including the activity of the specific compound employed, the age, body weight, general health, sex and diet of the individual being treated; the time and route of administration; the rate of excretion; other drugs which have previously been administered; and the severity of the particular condition undergoing therapy, as is well understood by those skilled in the art.

As noted above, formulations of the disclosure suitable for oral administration may be presented as discrete units such as capsules, cachets or tablets each containing a predetermined amount of the active ingredient, as a powder or granules; as a solution or a suspension in an aqueous or non-aqueous liquid, or as an oil-in-water liquid emulsion or a water-in-oil liquid emulsion. The pharmaceutical compositions may also be administered as a bolus, electuary or paste.

A tablet may be made by compression or molding, optionally with one or more accessory ingredients. Compressed tablets may be prepared by compressing in a suitable machine the active ingredient in a free flowing form such as a powder or granules, optionally mixed with a binder (e.g., povidone, gelatin, hydroxypropyl ethyl cellulose), lubricant, inert diluent, preservative, disintegrant (e.g., sodium starch glycolate, cross-linked povidone, cross-linked sodium carboxymethyl cellulose) surface active or dispersing agent. Molded tablets may be made in a suitable machine using a mixture of the powdered compound moistened with an inert liquid diluent. The tablets may optionally be coated or scored and may be formulated so as to provide slow or controlled release of the active ingredient therein using, for example, hydroxypropyl methylcellulose in varying proportions to provide the desired release profile. Tablets may optionally be provided with an enteric or colonic coating to provide release in parts of the gut other than the stomach. This is particularly advantageous with the compounds of formula 1 when such compounds are susceptible to acid hydrolysis.

Formulations suitable for topical administration in the mouth include lozenges comprising the active ingredient in a flavored base, usually sucrose and acacia or tragacanth; pastilles comprising the active ingredient in an inert base such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Injection solutions and suspensions may be prepared from sterile powders, granules and tablets of the kind previously described.

As used herein, pharmaceutically acceptable salts include, but are not limited to: acetate, pyridine, ammonium, piperazine, diethylamine, nicotinamide, formic, urea, sodium, potassium, calcium, magnesium, zinc, lithium, cinnamic, methylamino, methanesulfonic, picric, tartaric, triethylamino, dimethylamino, and tris(hydoxymethyl)aminomethane. Additional pharmaceutically acceptable salts are known to those skilled in the art.

An effective amount for a particular patient may vary depending on factors such as the condition being treated, the overall health of the patient, the route and dose of administration and the severity of side effects. Guidance for methods of treatment and diagnosis is available (see, e.g., Maynard, et al. (1996) A Handbook of SOPs for Good Clinical Practice, Interpharm Press, Boca Raton, Fla.; Dent (2001) Good Laboratory and Good Clinical Practice, Urch Publ., London, UK).

An effective amount may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of pharmaceutical composition. Where there is more than one administration of a pharmaceutical composition in the present methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of, for example, one week, two weeks, three weeks, four weeks, five weeks, six weeks, two months, three months, four months, five months, six months, seven months, eight months, nine months, ten months, eleven months, and twelve months.

Provided are cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non dosing can occur between a cycle, where the interval can be about, e.g., seven days; 14 days; 21 days; 28 days; 35 days; 42 days; 49 days; 56 days; 63 days; 70 days; and the like. In this context, the term "about" means plus or minus one day, plus or minus two days, plus or minus three days, plus or minus four days, plus or minus five days, plus or minus six days, or plus or minus seven days.

Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

As noted, the compositions of the present invention are preferably formulated as pharmaceutical compositions for parenteral or enteral delivery. A typical pharmaceutical composition for administration to an animal comprises a pharmaceutically acceptable vehicle such as aqueous solutions, non-toxic excipients, including salts, preservatives, buffers and the like. See, e.g., *Remington's Pharmaceutical Sciences*, 15th Ed., Easton ed., Mack Publishing Co., pp 1405-1412 and 1461-1487 (1975); *The National Formulary XIV, 14th Ed.*, American Pharmaceutical Association, Washington, D.C. (1975). Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components the pharmaceutical composition are adjusted according to routine skills in the art.

Repeated administrations of a particular vaccine (homologous boosting) have proven effective for boosting humoral responses. Such an approach may not be effective at boosting cellular immunity because prior immunity to the vector tends to impair robust antigen presentation and the generation of appropriate inflammatory signals. One approach to circumvent this problem has been the sequential administration of vaccines that use different antigen-delivery systems (heterologous boosting). In a heterologous boosting regimen, at least one prime or boost delivery comprises delivery of the inactivated tumor cell/cyclic purine dinucleotide compositions described herein. The heterologous arm of the regimen may comprise delivery of antigen using one or more of the following strategies:

inactivated or attenuated bacteria or viruses comprising the antigen of interest, which are particles that have been treated with some denaturing condition to render them ineffective or inefficient in mounting a pathogenic invasion;

purified antigens, which are typically naturally-produced antigens purified from a cell culture of the pathogen or a tissue sample containing the pathogen, or a recombinant version thereof;

live viral or bacterial delivery vectors recombinantly engineered to express and/or secrete antigens in the host cells of the subject. These strategies rely on attenuating (e.g., via genetic engineering) the viral or bacterial vectors to be non-pathogenic and non-toxic;

antigen presenting cell (APC) vectors, such as a dendritic cell (DC) vector, which comprise cells that are loaded with an antigen, or transfected with a composition comprising a nucleic acid encoding the antigen (e.g., Provenge® (Dendreon Corporation) for the treatment of castration-resistant metastatic prostate cancer);

liposomal antigen delivery vehicles; and naked DNA vectors and naked RNA vectors which may be administered by a gene gun, electroporation, bacterial ghosts, microspheres, microparticles, liposomes, polycationic nanoparticles, and the like.

A prime vaccine and a boost vaccine can be administered by any one or combination of the following routes. In one aspect, the prime vaccine and boost vaccine are administered by the same route. In another aspect, the prime vaccine and boost vaccine are administered by different routes. The term "different routes" encompasses, but is not limited to, different sites on the body, for example, a site that is oral, non-oral, enteral, parenteral, rectal, intranode (lymph node), intravenous, arterial, subcutaneous, intramuscular, intratumor, peritumor, intratumor, infusion, mucosal, nasal, in the cerebrospinal space or cerebrospinal fluid, and so on, as well as by different modes, for example, oral, intravenous, and intramuscular.

An effective amount of a prime or boost vaccine may be given in one dose, but is not restricted to one dose. Thus, the administration can be two, three, four, five, six, seven, eight, nine, ten, eleven, twelve, thirteen, fourteen, fifteen, sixteen, seventeen, eighteen, nineteen, twenty, or more, administrations of the vaccine. Where there is more than one administration of a vaccine the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. In the context of hours, the term "about" means plus or minus any time interval within 30 minutes. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, and combinations thereof. The invention is not limited to dosing intervals that are spaced equally in time, but encompass doses at non-equal intervals, such as a priming schedule consisting of administration at 1 day, 4 days, 7 days, and 25 days, just to provide a non-limiting example.

REFERENCES

1 Reed, S. G., Bertholet, S., Coler, R. N. & Friede, M. New horizons in adjuvants for vaccine development. Trends in immunology 30, 23-32, doi:10.1016/j.it.2008.09.006 (2009).
2 Dubensky, T. W., Jr. & Reed, S. G. Adjuvants for cancer vaccines. Seminars in immunology 22, 155-161, doi: 10.1016/j.smim.2010.04.007 (2010).
3 Kastenmuller, K. et al. Protective T cell immunity in mice following protein-TLR7/8 agonist-conjugate immunization requires aggregation, type I IFN, and multiple DC subsets. The Journal of clinical investigation 121, 1782-1796, doi:10.1172/JCI45416 (2011).
4 Coffman, R. L., Sher, A. & Seder, R. A. Vaccine adjuvants: putting innate immunity to work. Immunity 33, 492-503, doi:10.1016/j.immuni.2010.10.002 (2010).
5 Burdette, D. L. et al. STING is a direct innate immune sensor of cyclic di-GMP. Nature 478, 515-518, doi: 10.1038/nature10429 (2011).
6 Woodward, J. J., Iavarone, A. T. & Portnoy, D. A. c-di-AMP secreted by intracellular *Listeria monocytogenes* activates a host type I interferon response. Science 328, 1703-1705, doi:10.1126/science.1189801 (2010).
7 Ishikawa, H. & Barber, G. N. STING is an endoplasmic reticulum adaptor that facilitates innate immune signalling. Nature 455, 674-678, doi:10.1038/nature07317 (2008).
8 McWhirter, S. M. et al. A host type I interferon response is induced by cytosolic sensing of the bacterial second messenger cyclic-di-GMP. The Journal of experimental medicine 206, 1899-1911, doi:10.1084/jem.20082874 (2009).
9 Bahjat, K. S. et al. (2005).
10 Bahjat, K. S. et al. Cytosolic Entry Controls CD8+-T-Cell Potency during Bacterial Infection. Infection and immunity 74, 6387-6397 (2006).
11 Crimmins, G. T. et al. *Listeria monocytogenes* multidrug resistance transporters activate a cytosolic surveillance pathway of innate immunity. Proceedings of the National Academy of Sciences of the United States of America (2008).
12 O'Riordan, M., Yi, C. H., Gonzales, R., Lee, K. D. & Portnoy, D. A. Innate recognition of bacteria by a macrophage cytosolic surveillance pathway. Proceedings of the National Academy of Sciences of the United States of America 99, 13861-13866 (2002).
13 Schwartz, K. T. et al. Hyperinduction of host beta interferon by a *Listeria monocytogenes* strain naturally overexpressing the multidrug efflux pump MdrT. Infection and immunity 80, 1537-1545, doi:10.1128/IAI.06286-11 (2012).
14 Davies, B. W., Bogard, R. W., Young, T. S. & Mekalanos, J. J. Coordinated regulation of accessory genetic elements produces cyclic di-nucleotides for *V. cholerae* virulence. Cell 149, 358-370, doi:10.1016/j.cell.2012.01.053 (2012).
15 Witte, C. E. et al. Innate immune pathways triggered by *Listeria monocytogenes* and their role in the induction of cell-mediated immunity. Advances in immunology 113, 135-156, doi:10.1016/B978-0-12-394590-7.00002-6 (2012).
16 Desmet, C. J. & Ishii, K. J. Nucleic acid sensing at the interface between innate and adaptive immunity in vaccination. Nature reviews. Immunology 12, 479-491, doi: 10.1038/nri3247 (2012).
17 Rappuoli, R., Mandl, C. W., Black, S. & De Gregorio, E. Vaccines for the twenty-first century society. Nature reviews. Immunology 11, 865-872, doi:10.1038/nri3085 (2011).
18 Iwasaki, A. & Medzhitov, R. Regulation of adaptive immunity by the innate immune system. Science 327, 291-295, doi:10.1126/science.1183021 (2010).
19 Kawai, T. & Akira, S. The role of pattern-recognition receptors in innate immunity: update on Toll-like receptors. Nature immunology 11, 373-384, doi:10.1038/ni.1863 (2010).
20 Einstein, M. H. et al. Comparison of the immunogenicity and safety of Cervarix and Gardasil human papillomavirus (HPV) cervical cancer vaccines in healthy women aged 18-45 years. Human vaccines 5, 705-719 (2009).
21 Ahmed, S. S., Plotkin, S. A., Black, S. & Coffman, R. L. Assessing the safety of adjuvanted vaccines. Science translational medicine 3, 93rv92, doi:10.1126/scitranslmed.3002302 (2011).
22 Vance, R. E., Isberg, R. R. & Portnoy, D. A. Patterns of pathogenesis: discrimination of pathogenic and nonpathogenic microbes by the innate immune system. Cell host & microbe 6, 10-21, doi:10.1016/j.chom.2009.06.007 (2009).
23 Barber, G. N. STING-dependent signaling. Nature immunology 12, 929-930, doi:10.1038/ni.2118 (2011).
24 Leber, J. H. et al. Distinct TLR- and NLR-mediated transcriptional responses to an intracellular pathogen. PLoS pathogens 4, e6 (2008).
25 Jin, L. et al. MPYS is required for IFN response factor 3 activation and type I IFN production in the response of cultured phagocytes to bacterial second messengers cyclic-di-AMP and cyclic-di-GMP. J Immunol 187, 2595-2601, doi:10.4049/jimmunol.1100088 (2011).
26 Lauvau, G. et al. Priming of memory but not effector CD8 T cells by a killed bacterial vaccine. Science 294, 1735-1739 (2001).
27 Bahjat, K. S. et al. Suppression of cell-mediated immunity following recognition of phagosome-confined bacteria. PLoS pathogens 5, e1000568, doi:10.1371/journal.ppat.1000568 (2009).
28 Tamayo, R., Pratt, J. T. & Camilli, A. Roles of cyclic diguanylate in the regulation of bacterial pathogenesis. Annual review of microbiology 61, 131-148, doi:10.1146/annurev.micro.61.080706.093426 (2007).
29 Sauer, J. D. et al. The N-ethyl-N-nitrosourea-induced Goldenticket mouse mutant reveals an essential function of Sting in the in vivo interferon response to *Listeria monocytogenes* and cyclic dinucleotides. Infection and immunity 79, 688-694, doi:10.1128/IAI.00999-10 (2011).

30 Barber, G. N. Cytoplasmic DNA innate immune pathways. Immunological reviews 243, 99-108, doi:10.1111/j.1600-065X.2011.01051.x (2011).

31 Tanaka, Y. & Chen, Z. J. STING specifies IRF3 phosphorylation by TBK1 in the cytosolic DNA signaling pathway. Science signaling 5, ra20, doi:10.1126/scisignal.2002521 (2012).

32 Ebensen, T. et al. Bis-(3',5')-cyclic dimeric adenosine monophosphate: strong Th1/Th2/Th17 promoting mucosal adjuvant. Vaccine 29, 5210-5220, doi:10.1016/j.vaccine.2011.05.026 (2011).

33 Ebensen, T. et al. The bacterial second messenger cyclic diGMP exhibits potent adjuvant properties. Vaccine 25, 1464-1469, doi:10.1016/j.vaccine.2006.10.033 (2007).

34 Ebensen, T., Schulze, K., Riese, P., Morr, M. & Guzman, C. A. The bacterial second messenger cdiGMP exhibits promising activity as a mucosal adjuvant. Clinical and vaccine immunology: CVI 14, 952-958, doi:10.1128/CVI.00119-07 (2007).

35 Libanova, R. et al. The member of the cyclic di-nucleotide family bis-(3', 5')-cyclic dimeric inosine monophosphate exerts potent activity as mucosal adjuvant. Vaccine 28, 2249-2258, doi:10.1016/j.vaccine.2009.12.045 (2010).

36 Madhun, A. S. et al. Intranasal c-di-GMP-adjuvanted plant-derived H5 influenza vaccine induces multifunctional Th1 CD4+ cells and strong mucosal and systemic antibody responses in mice. Vaccine 29, 4973-4982, doi:10.1016/j.vaccine.2011.04.094 (2011).

37 Hu, D. L. et al. c-di-GMP as a vaccine adjuvant enhances protection against systemic methicillin-resistant *Staphylococcus aureus* (MRSA) infection. Vaccine 27, 4867-4873, doi:10.1016/j.vaccine.2009.04.053 (2009).

38 Karaolis, D. K. et al. Cyclic di-GMP stimulates protective innate immunity in bacterial pneumonia. Infection and immunity 75, 4942-4950, doi:10.1128/IAL01762-06 (2007).

39 Ogunniyi, A. D. et al. c-di-GMP is an effective immunomodulator and vaccine adjuvant against pneumococcal infection. Vaccine 26, 4676-4685, doi:10.1016/j.vaccine.2008.06.099 (2008).

40 Karaolis, D. K. et al. Bacterial c-di-GMP is an immunostimulatory molecule. J Immunol 178, 2171-2181 (2007).

41 Wille-Reece, U. et al. Toll-like receptor agonists influence the magnitude and quality of memory T cell responses after prime-boost immunization in nonhuman primates. The Journal of experimental medicine 203, 1249-1258 (2006).

42 Adler-Moore, J. et al. Characterization of the murine Th2 response to immunization with liposomal M2e influenza vaccine. Vaccine 29, 4460-4468, doi:10.1016/j.vaccine.2011.04.040 (2011).

43 Fujii, G., Ernst, W. & Adler-Moore, J. The VesiVax system: a method for rapid vaccine development. Frontiers in bioscience: a journal and virtual library 13, 1968-1980 (2008).

44 Gaffney, B. L., Veliath, E., Zhao, J. & Jones, R. A. One-flask syntheses of c-di-GMP and the [Rp,Rp] and [Rp,Sp] thiophosphate analogues. Organic letters 12, 3269-3271, doi:10.1021/ol101236b (2010).

45 Zhang, Z., Gaffney, B. L. & Jones, R. A. c-di-GMP displays a monovalent metal ion-dependent polymorphism. Journal of the American Chemical Society 126, 16700-16701, doi:10.1021/ja0449832 (2004).

46 Suzuki, N., Oyama, K.-i. & Tsukamoto, M. Practical Synthesis of Cyclic Bis(3'-5')diadenylic Acid (c-di-AMP). Chemistry Letters 40, 1113-1114, doi:10.1246/cl.2011.1113 (2011).

47 Hyodo, M., Sato, Y. & Hayakawa, Y. Synthesis of cyclic bis(3'-5')diguanylic acid (c-di-GMP) analogs. Tetrahedron 62, 3089-3094, doi:10.1016/j.tet.2006.01.025 (2006).

48 Yan, H., Wang, X., KuoLee, R. & Chen, W. Synthesis and immunostimulatory properties of the phosphorothioate analogues of cdiGMP. Bioorganic & medicinal chemistry letters 18, 5631-5634, doi:10.1016/j.bmcl.2008.08.088 (2008).

49 Ross, P. et al. The cyclic diguanylic acid regulatory system of cellulose synthesis in *Acetobacter xylinum*. Chemical synthesis and biological activity of cyclic nucleotide dimer, trimer, and phosphothioate derivatives. The Journal of biological chemistry 265, 18933-18943 (1990).

50 Grajkowski, A., Cieslak, J., Gapeev, A., Schindler, C. & Beaucage, S. L. Convenient synthesis of a propargylated cyclic (3'-5') diguanylic acid and its "click" conjugation to a biotinylated azide. Bioconjugate chemistry 21, 2147-2152, doi:10.1021/bc1003857 (2010).

51 Zhao, J., Veliath, E., Kim, S., Gaffney, B. L. & Jones, R. A. Thiophosphate analogs of c-di-GMP: impact on polymorphism. Nucleosides, nucleotides & nucleic acids 28, 352-378, doi:10.1080/15257770903044523 (2009).

52 Battistini, C., Fustinoni, S., Brasca, M. & Borghi, D. Stereoselective synthesis of cyclic dinucleiotide phosphorothioates. Tetrahedron, 1115-1132 (1993).

53 Hayakawa, Y. A facile synthesis of cyclic bis(3'-*5') diguanylic acid. Tetrahedron 59, 6465-6471, doi:10.1016/s0040-4020(03)01045-7 (2003).

54 Coughlin, J. E. et al. Orally bioavailable anti-HBV dinucleotide acyloxyalkyl prodrugs. Bioorganic & medicinal chemistry letters 20, 1783-1786, doi:10.1016/j.bmcl.2010.01.010 (2010).

55 Ouyang, S. et al. Structural Analysis of the STING Adaptor Protein Reveals a Hydrophobic Dimer Interface and Mode of Cyclic di-GMP Binding. Immunity, doi:10.1016/j.immuni.2012.03.019 (2012).

56 Baldwin, S. L. et al. The importance of adjuvant formulation in the development of a tuberculosis vaccine. J Immunol 188, 2189-2197, doi:10.4049/jimmunol.1102696 (2012).

57 Lee, A. W. et al. A clinical grade cocktail of cytokines and PGE2 results in uniform maturation of human monocyte-derived dendritic cells: implications for immunotherapy. Vaccine 20 Suppl 4, A8-A22 (2002).

58 Lubong Sabado, R. et al. In vitro priming recapitulates in vivo HIV-1 specific T cell responses, revealing rapid loss of virus reactive CD4 T cells in acute HIV-1 infection. PloS one 4, e4256, doi:10.1371/journal.pone.0004256 (2009).

59 Skoberne, M. et al. KBMA *Listeria monocytogenes* is an effective vector for DC-mediated induction of antitumor immunity. The Journal of clinical investigation (2008).

60 Jin, L. et al. Identification and characterization of a loss-of-function human MPYS variant. Genes and immunity 12, 263-269, doi:10.1038/gene.2010.75 (2011).

61 Schmidt, N. W. et al. Memory CD8 T cell responses exceeding a large but definable threshold provide long-term immunity to malaria. Proceedings of the National Academy of Sciences of the United States of America 105, 14017-14022 (2008).

62 Pham, N. L. et al. Exploiting cross-priming to generate protective CD8 T-cell immunity rapidly. Proceedings of the National Academy of Sciences of the United States of America 107, 12198-12203, doi:10.1073/pnas.1004661107 (2010).

63 Badovinac, V. P., Messingham, K. A., Jabbari, A., Haring, J. S. & Harty, J. T. Accelerated CD8+ T-cell memory and prime-boost response after dendritic-cell vaccination. Nature medicine 11, 748-756 (2005).

64 Harty, J. T. & Badovinac, V. P. Shaping and reshaping CD8+ T-cell memory. Nature reviews. Immunology 8, 107-119 (2008).

65 Coler, R. N. et al. Development and characterization of synthetic glucopyranosyl lipid adjuvant system as a vaccine adjuvant. PloS one 6, e16333, doi:10.1371/journal.pone.0016333 (2011).

66 Singh, S., Briles, W. E., Lupiani, B. & Collisson, E. W. Avian influenza viral nucleocapsid and hemagglutinin proteins induce chicken CD8+ memory T lymphocytes. Virology 399, 231-238, doi:10.1016/j.virol.2009.12.029 (2010).

67 Singh, S. et al. Non-replicating adenovirus vectors expressing avian influenza virus hemagglutinin and nucleocapsid proteins induce chicken specific effector, memory and effector memory CD8(+) T lymphocytes. Virology 405, 62-69, doi:10.1016/j.virol.2010.05.002 (2010).

68 Tewari, K. et al. Poly(I:C) is an effective adjuvant for antibody and multi-functional CD4+ T cell responses to *Plasmodium falciparum* circumsporozoite protein (CSP) and alphaDEC-CSP in non human primates. Vaccine 28, 7256-7266, doi:10.1016/j.vaccine.2010.08.098 (2010).

69 Wille-Reece, U. et al. HIV Gag protein conjugated to a Toll-like receptor 7/8 agonist improves the magnitude and quality of Th1 and CD8+ T cell responses in nonhuman primates. Proceedings of the National Academy of Sciences of the United States of America 102, 15190-15194, doi:10.1073/pnas.0507484102 (2005).

70 Seder, R. A., Darrah, P. A. & Roederer, M. T-cell quality in memory and protection: implications for vaccine design. Nature reviews. Immunology 8, 247-258 (2008).

71 Wille-Reece, U., Wu, C. Y., Flynn, B. J., Kedl, R. M. & Seder, R. A. Immunization with HIV-1 Gag protein conjugated to a TLR7/8 agonist results in the generation of HIV-1 Gag-specific Th1 and CD8+ T cell responses. J Immunol 174, 7676-7683 (2005).

72 Jones et al., US20120178710.

EXAMPLES

The following examples serve to illustrate the present invention. These examples are in no way intended to limit the scope of the invention.

Example 1. General Methods

Anhydrous solvents and reagents suitable for solution phase oligonucleotide synthesis were purchased and handled under dry argon or nitrogen using anhydrous technique. Amidite coupling reactions and cyclizations were carried out in anhydrous acetonitrile or pyridine under dry argon or nitrogen. The starting materials for all reactions in dry pyridine were dried by concentration (three times) from pyridine. Preparative silica gel flash chromatography was carried out using Fluka 60 Å high-purity grade or Merck Grade 9385 silica using gradients of methanol in dichloromethane. Analytical HPLC was carried out on a Varian ProStar 210 HPLC system with a ProStar 330 photodiode array detector monitoring at 254 nm on a Varian Microsorb 100-10 $C_{18}$ 250×4.6 mm column using gradients of 10 mM TEAA and acetonitrile at 1.0 ml/min flow. Preparative HPLC was carried out on a Shimadzu preparative LC20-AP HPLC system, equipped with a SPD-20A UV/Vis detector monitoring at 254 nm on a Varian Microsorb 60-8 C-18 41.6×250 mm column using gradients of 10 mM TEAA and acetonitrile at a flow rate 50 ml/min. Solid phase extractions using C-18 Sep-Pak (Waters) were carried out at a loadings of ~3% (wt/wt). LC/MS (ESI/APCI) was obtained on a single quadrapole Shimadzu 2010EV instrument with PDA, MS, and ELSD detection using a Shimadzu LC20D analytical HPLC. High resolution FT-ICR mass spec was obtained from WM Keck Foundation Biotechnology Resource Laboratory at Yale University in New Haven, Conn. The $^1$H and $^{31}$P NMR spectra were acquired on either a Bruker 400 MHz or a Varian Inova 500 MHz spectrometer. The $^{31}$P NMR were referenced indirectly to dioxane in D2O.

The assignment of the HPLC purified cyclic dinucleotides and derivatives are summarized in Table 1 and described in detail in the Examples.

TABLE 1

Retention times on Reverse Phase HPLC (min) and $^{31}$P Chemical Shifts (ppm) at 25° C. of triethylammonium salts (10a, 10b, 10c, 11a, 11b, 11c, 12, 13)

| compound | retention time | $^{31}$P δ |
|---|---|---|
| c-di-AMP 10a | 8.2* | −1.74 |
| dithio [Rp,Sp] c-di-AMP 10c | 12.1* | 54.54, 54.84, 55.92 (integration ratio 1.0:0.9:0.1) |
| dithio [Rp,Rp] c-di-AMP 10b | 14.4* | 54.41 |
| c-di-GMP 11a | 6.9* | −1.24 |
| dithio [Rp,Sp] c-di-GMP 11c | 11.0* | 54.77, 56.00 (integration ratio 1:1) |
| dithio [Rp,Rp] c-di-GMP 11b | 13.2* | 54.87 |
| $C_{14}$-acyl-c-di-GMP 12 | 13.7‡ | −1.37, −2.06 (integration ratio 1:1) |
| $C_{14}$-acyl-dithio [Rp,Rp] c-di-GMP 13 | 15.3‡ | 56.46, 56.66 (integration ratio 1:1) |

*HPLC gradient: 2 to 20% $CH_3CN$ in 10 mM TEAA over 20 min at 1 ml/min flow.
‡HPLC gradient: 2 to 80% $CH_3CN$ in 10 mM TEAA over 20 min at 1 ml/min flow.

Example 2. Synthesis of 10a

Figure 6:
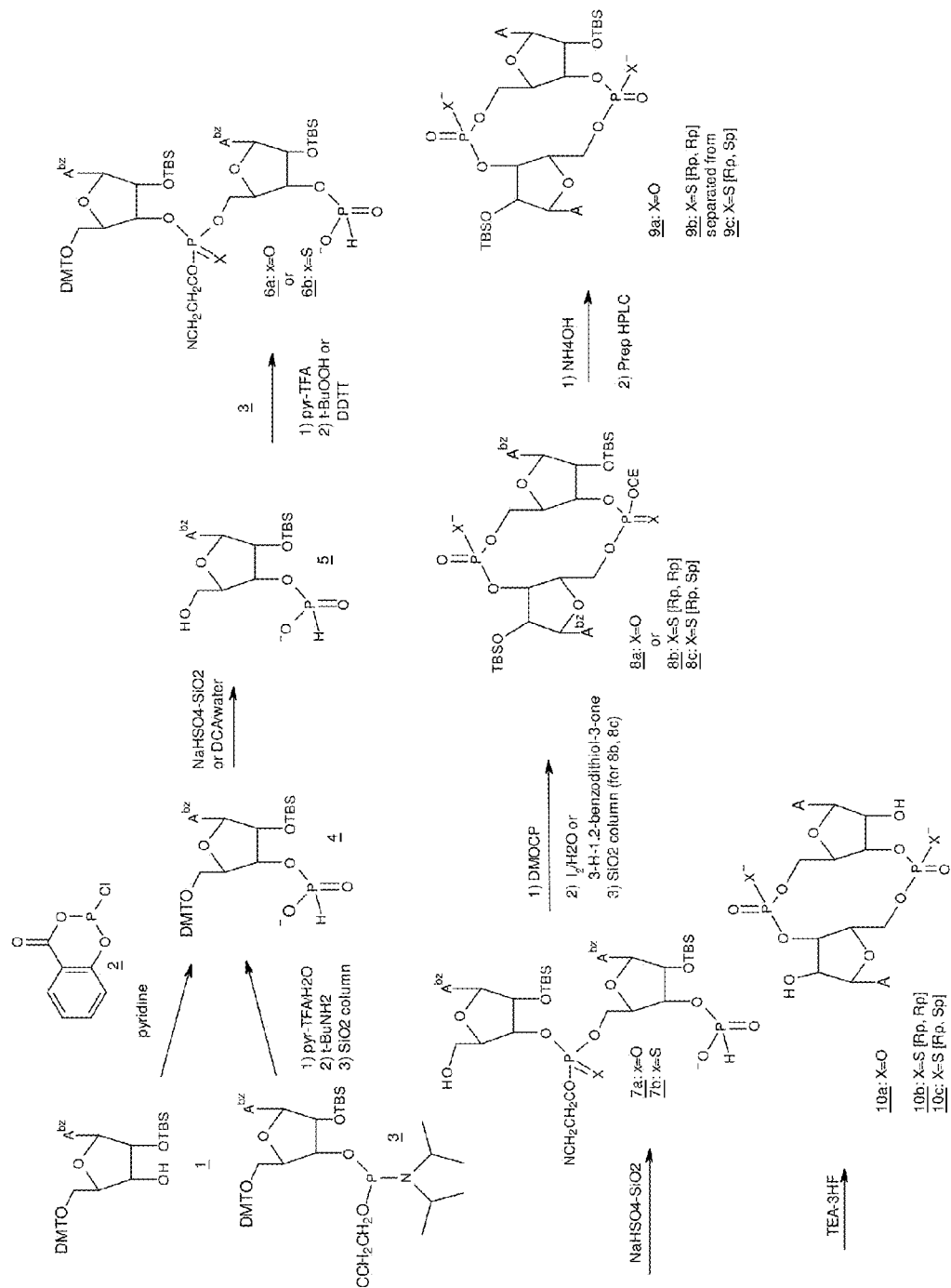
FIG. 6 depicts a synthesis scheme for c-di-AMP and c-di-AMP-thiophosphate.

The following synthesis of cyclic-di-AMP is described schematically in FIG. 6 and is a modification of a synthesis of cyclic-di-GMP reported by Gaffney et al. (One-flask synthesis of c-di-GMP and the [Rp,Rp] and [Rp,Sp] thiophosphate analogues. Organic Letters 12, 3269-3271 (2010)).

a) Phosphitylation of 1 with 2-Chloro-5,6-Benzo-1,3,2-Dioxaphosphorin-4-One (2) and Solid-Liquid Extraction with CH2Cl2/Hexane (1:1) to Give the 5'-DMT-3'-H-Phosphonate 4.

To a solution of 1 (3.94 g, 5 mmol) in 15 ml anhydrous dioxane and 5 ml of dry pyridine was added with stirring 5.6 ml (7.0 mmol) of a 1.25 M stock solution in dioxane of 2-chloro-5,6-benzo-1,3,2-dioxaphosphorin-4-one (2). After 15 min the reaction was quenched with 1 ml water and the mixture poured into 10 ml 0.25 M NaHCO3 followed by extraction (3×15 ml) with ethyl acetate. The organic phase was dried (Na2SO4) and concentrated to yield 3.8 g. The solid was tritrated with 100 ml of CH2Cl2/hexane (1:1), filtered, and the residual solid dried to give a fine white powder (3.5 g) that ran as one spot on TLC (Rf=0.1) eluting with 5% CH3OH in CH2Cl2 with 0.5% triethylamine.

b) Detritylation by Sodium Bisulfate Absorbed to Silica Gel (NaHSO4-SiO2) and Precipitation of the 5'-OH-3'-H-Phosphonate (5).

To a solution of 4 (1.74 g, 2 mmol) in 85 ml dichloromethane and 0.072 ml of water (4 mmole) was added 0.55 g of NaHSO4-SiO2 (2.4 mmol Mgr NaHSO4-SiO2). The reaction was complete after stirring at room temperature for 35 minutes (TLC in 10% MeOH in CH2Cl2 with 0.5% TEA). The NaHSO4-SiO2 was removed by filtration and washed (3×5 ml) with CH2Cl2. 100 ml of hexane:toluene (1:1) was added, vortexed for 5 minutes and the solvent was decanted (repeated twice). Evaporation gave 0.92 g of 5 as a solid. Analytical HPLC indicated purity of 96.4%. LC/MS in negative mode confirmed m/z (M-1) 548.2 (calculated for $C_{23}H_{31}N_5O_7PSi^-$: 548.2).

c) Coupling, Oxidation and Detritylation.

DMT-rA(bz)-βCE-TBDMS-phosphoramidite (3), (3.5 g, 3.6 mmole) was coevaporated three times with 20 ml dry acetonitrile, the last time leaving about 10 ml volume, to which was added ten 3 Å molecular sieves. The solution was left under dry argon.

1.6 g of H-phosphonate (5) was evaporated three times from anhydrous CH3CN, the last time leaving 100 ml. This solution was added to the dried phosphoramidite solution via syringe, followed by 1.4 g of pyridinium trifluoroacetate (which had been dried by evaporating 3×20 ml from anhydrous pyridine). After 20 min 3 ml of 5.5 M tert-butylhydroperoxide was added and stirred for 30 min. After cooling in ice bath, 0.3 g of NaHSO3 in 1 ml of water was added and the mix stirred for 5 min. The solvent was then evaporated and the residue taken up in 20 ml ($CH_2Cl_2$/MeOH, 98:2). The sieves were filtered off and solvent switched to 81 ml $CH_2Cl_2$. $NaHSO_4$—$SiO_2$ (513 mg) and water (65 microliters) were added and the reaction stirred for 40 min. The mixture was filtered through Celite, the pad washed with $CH_2Cl_2$, and the filtrate evaporated to give crude 7a. LC/MS in negative mode confirmed m/z (M-1) 1148.5 (calcd for $C_{49}H_{64}N_{11}O_{14}P_2Si_2^-$: 1148.37.

d) Cyclization of Linear Dimer (7a) and Oxidation to Give 8a.

To crude 7a (dried by evaporation from anhydrous pyridine leaving 100 ml after final evaporation) was added DMOCP (1.9 g, 10.15 mmol). After 12 minutes, the reaction was quenched with water (2.3 g) followed immediately by the addition of iodine (0.96 g, 3.78 mmol). The reaction mix was poured into 400 ml water containing 0.6 g NaHSO3. After 5 min stirring, 11.2 g NaHCO3 was added in portions and the solution stirred for 5 min. The mixture was partitioned two times with 500 ml ethyl acetate/ether (3:2). The organic layers were combined, dried ($Na_2SO_4$), and evaporated. Toluene (3×10 ml) was added and evaporated to remove residual pyridine to give 2.37 g of 8a as a yellow-brown solid. LC/MS in negative mode confirmed m/z (M-1) 1146.6 (calcd for $C_{49}H_{62}N_{11}O_{14}P_2Si_2^-$: 1146.4 e) Deprotection Crude 8a with Concentrated Ammonium Hydroxide to Give Crude 9a and Prep HPLC to Give 9a in Pure Form.

To 600 mg of 8a in a 200 ml thick walled glass pressure tube was added 40 ml methanol and 40 ml concentrated aqueous ammonia, and the resulting mixture was stirred at 50° C. for 16 hr. The reaction mixture was concentrated under vacuum and the residue washed with ethyl acetate (3×10 ml) to give 510 mg of crude 9a.

A 102 mg portion of crude 9a in 4 ml of 20% CH3CN in 10 mM triethylammonium acetate was applied to the prep HPLC column and eluted using a gradient of acetonitrile and 10 mM triethylammonium acetate in water (20→50% CH3CN over 20 minutes at 50 ml/min flow). HPLC fractions containing pure 9a were pooled, evaporated to remove CH3CN and lyophilized to remove remaining water and volatile buffer to give 32 mg of pure 9a as the bis-triethylammonium salt. LC/MS in negative mode confirmed m/z (M-1) 885.5 (calcd for $C_{32}H_{51}N_{10}O_{12}P_2Si_2^-$: 885.3. (It was also possible to defer the prep HPLC purification until after the last step as described in the c-di-GMP and dithio-c-di-GMP series below).

f) Deprotection of TBS Groups of 9a with Triethylamine Trihydrofluoride, Neutralization with TEAB, and Solid Phase Extraction with a C-18 Sep-Pak to Give Pure 10a as the Bis-Triethylammonium Salt.

To 20 mg of 9a was added 0.25 ml of triethylamine trihydrofluoride. The mixture was put on a shaker for 48 h at which point an analytical HPLC of a 10 microliter sample neutralized with 100 microliter of 1 M triethylammonium bicarbonate indicated consumption of starting material and appearance of a single new product. The reaction mixture was then added dropwise with stirring to a 10× volume of chilled 1 M triethylammonium bicarbonate. The neutralized solution was then loaded on a Waters C-18 Sep-Pak, and after washing the column with 6 volumes of 10 mM triethylammmonium acetate, the product was eluted with CH3CN: triethylammonium acetate (1:1). The CH3CN was removed via rotoevaporation and the aqueous sample was lyophilized to dryness to give 14 mg of 10a as the bis-triethylammonium salt. HRMS of 10a in negative mode confirms m/z (M-H) 657.0985 (calculated for $C_{20}H_{23}N_{10}O_{12}P_2^-$: 657.0978). $^1$H NMR ($D_2O$) 45° C. δ (ppm) 8.34 (s, 2H), 8.11 (s, 2H), 6.15 (s, 2H), 4.34 (m, 4H), 4.15 (m, 2H), 3.77 (m, 2H), 3.19 (q, J=7 Hz), 1.27 (t, J=7 Hz). $^{31}$P NMR (D2O) 25° C. δ (ppm) −1.74.

Example 3. Synthesis of 10b and 10c

The following synthesis is described schematically in FIG. 6.

a) Hydrolysis of Commercially Available DMT-rA(Bz)-βCE-TBDMS-Phosphoramidite (3), β-Elimination, and Silica Chromatography of the Resulting 5'-DMT-3'-H-Phosphonate (4):

To a solution of DMT-rA(bz)-βCE-TBDMS-phosphoramidite (3) (11 g, 11.1 mmole) in 50 ml acetonitrile was added water (0.36 ml, 20 mmole, 1.8 equiv) and pyridinium trifluroacetate (2.3 g, 11.9 mmole, 1.07 equiv) After stifling the mixture for 5 minutes at room temperature tert-butylamine (50 ml) was added and stifling continued for an additional 10 minutes. The mixture was then concentrated to a foam which was taken up in dichloromethane and applied to a silica gel column eluting with a gradient of 5% to 10% MeOH in dichloromethane. Column fractions containing the desired product were pooled and concentrated to yield the 5'-DMT-3'-H-phosphonate (4) as a foam (6.68 g, 7.8 mmole, 70% yield)

b) Detritylation and Precipitation of the 5'-OH-3'-H-Phosphonate (5):

To a solution of 4 (6.68 g, 7.8 mmol) in 60 ml dichloromethane and 1.4 ml of water (78 mmole, 10 equiv) was added a 100 ml portion of 6% dichloroacetic acid in dichloromethane (73 mmole, 9.35 equiv). After stifling at room temperature for 10 minutes, pyridine (11.2 ml, 139 mmole, 1.9 equiv based on DCA) was added to quench the acid and the mixture concentrated to give 5 as a yellow/orange glass. The glass was taken up in about 20 ml of dichloromethane and added dropwise with stifling to 500 ml of 7:3 hexane:diethylether to precipitate out the desired 5'-OH-3'-H-phosphonate (5). The supernatant was decanted away from the precipitate (most of which formed a gum clinging to the walls of the flask) and was dried down under reduced pressure to form a granular slurry. This slurry was evaporated three times with 40 ml of dry acetonitrile, the last time leaving about 12 ml.

c) Preparation of a Dry Solution of Phosphoramidite (3) in Acetonitrile, Coupling with 5'-OH-3'-H-Phosphonate 5), and Sulfurization to the Linear Dimer Thiophosphate (6b), and Detritylation to 7b.

The DMT-rA(bz)-βCE-TBDMS-phosphoramidite (3), (9.08 g, 9.36 mmole, 1.2 equiv based on H-phosphonate (5) was coevaporated three times with 40 ml dry acetonitrile, the last time leaving about 20 ml volume, to which was added ten 3 Å molecular sieves. The solution was left under dry argon.

To the solution of phosphoramidite (3) was added 5 (from b) with stifling under dry argon. After stifling for 10 minutes at room temperature, half of the reaction mixture (for conversion to the dithio analogs) was transferred under argon to a second reaction vessel, and 3-((N,N-dimethylaminomethylidene)amino-3H-1,2,4-dithiazole-5-thione (0.88 g, 4.29 mmol, 1.1 equivalent) was added. After 30 min stirring at room temp the reaction was stopped by placing in a freezer at −20° C. While stored in freezer for >48 h a yellow precipitate separated from the solution. The mixture was filtered and the filtrate concentrated to a foam (3.9 g), dissolved in 50 ml CH2Cl2 and treated with 100 ul water followed immediately by 800 mg of NaHSO4-silica. The mixture was stirred for 30 min at room temperature and filtered to remove the silica. Sixty ml of hexane was then added to the filtrate and a lower phase oiled out of the solution. The oil was separated and evaporated to yield 3.1 g of crude 7b.

d) Cyclization of Linear Dimer (7b), Sulfurization, and Silica Chromatography to Give a Mixture of 8b and 8c.

7b (3.05 g, 2.6 mmol) was dried by evaporation from anhydrous pyridine (200 ml pyridine was added and rotoevaporated to leave 120 ml) followed by addition of DMOCP (1.68 g, 9.1 mmol, 3.5 equiv). After 12 minutes, the reaction was quenched with water (1.63 g, 91 mmol) followed immediately by the addition of 0.675 g (3.0 mmol, 1.2 equiv) of 3-H-1,2-benzodithiol-3-one. The reaction mix was poured into 500 ml of 0.25 M sodium bicarbonate and then extracted 2×500 ml with ethylaceate/diethylether (3:2). The organic layers were combined, dried (Na2SO4), and evaporated under vacuum. Toluene (3×10 ml) was added and evaporated to remove residual pyridine. The residue was applied to a silica column and eluted with a gradient of 0 to 10% of CH3OH in CH2Cl2 to give a total of 1.47 g containing mostly diastereomers 8b and 8c.

e) Deprotection of the Mixture of 8b and 8c with Concentrated Ammonium Hydroxide to Give 9b and 9c, and Separation Via Prep HPLC to Give 9b and 9c in Pure Form.

To 230 mg of a mixture of 8b and 8c in a glass pressure tube was added 16 ml methanol followed by 16 ml concentrated aqueous ammonia, and the resulting mixture was stirred at 50° C. for 16 hr. The reaction mixture was concentrated under vacuum and the residue washed with ethyl acetate (3×10 ml) to give 210 mg of a crude mixture of 9b and 9c. LC/MS in negative mode for 9b/9c mixture confirmed m/z (M-1) 917 (calcd for $C_{32}H_{51}N_{10}O_{10}P_2S_2Si_2^-$: 917.2.

Separation of the mixture of 9b/9c via prep HPLC. A 105 mg portion of the crude mix of 9b and 9c in 4 ml of 30% CH3CN in 10 mM triethylammonium acetate was applied to the prep HPLC column and eluted using a gradient of acetonitrile and 10 mM triethylammonium acetate (30→50% CH3CN over 20 minutes at 50 ml/min flow). HPLC fractions containing pure 9b were separated from those containing pure 9c. The pooled fractions were evaporated to remove CH3CN and lyophilized to remove remaining water and volatile buffer to give 18 mg of 9b and 14 mg of 9c as the bis-triethylammonium salts.

f) Deprotection of TBS Groups of 9b with Triethylamine Trihydrofluoride, Neutralization with TEAB, and Solid Phase Extraction (SPE) with a C-18 Sep-Pak to Give Pure 10b as the Bis-Triethylammonium Salt.

To 8 mg of 9b was added 0.4 ml of triethylamine trihydrofluoride. The mixture was put on a shaker for 16 h at which point an analytical HPLC of a 5 microliter sample neutralized with 100 microliter of 1 M triethylammonium bicarbonate (TEAB) indicated consumption of starting material and appearance of a single new product. The reaction mixture was then added dropwise with stifling to a ~10× volume of chilled 1 M triethylammonium bicarbonate. The neutralized solution was then loaded on a Waters C-18 Sep Pak, and after washing the column with 6 volumes of 10 mM triethylammmonium acetate, the product was eluted with CH3CN: 10 mM triethylammonium acetate (1:5). The CH3CN was removed via rotoevaporation and the aqueous sample was lyophilized to dryness to give 6 mg of 10b as the bis-triethylammonium salt. HRMS of 10b in negative mode confirms m/z (M-H) 689.0526 (calculated for $C_{20}H_{23}N_{10}O_{10}P_2S_2^-$: 689.0521). $^1$H NMR (D$_2$O) 35° C. δ8.39 (s, 2H), δ8.16 (s, 2H), δ6.16 (s, 2H), δ4.97-5.03 (m, 2H), δ4.78 (m, 2H), δ4.50-4.55 (m, 4H), δ4.04-4.08 (m, 2H), δ3.20 (q, j=7 Hz), δ1.27 (1, J=7 Hz). $^{31}$P NMR (D2O) 25° C. δ (ppm) 54.41.

g) Deprotection of TBS Groups of 9c with Triethylamine Trihydrofluoride, Neutralization with TEAB, and Solid Phase Extraction with a C-18 Sep-Pak to Give Pure 10c as the Bis-Triethylammonium Salt.

To 6 mg of 9c was added 0.3 ml of triethylamine trihydrofluoride. The mixture was put on a shaker for 16 h and a work-up of a small aliquot as in (f) indicated consumption of starting material and appearance of a single new product. The reaction mixture was then added dropwise with stifling to a ~10× volume of chilled 1 M triethylammonium bicarbonate. The neutralized solution was then loaded on a Waters C-18 Sep Pak, and after washing the column with 6 volumes of 10 mM triethylammmonium acetate, the product was eluted with CH3CN: 10 mM triethylammonium acetate (1:5). The CH3CN was removed via rotoevaporation and the aqueous sample was lyophilized to dryness to give 4 mg of 10c as the bis-triethylammonium salt. HRMS of 10c in negative mode confirms m/z (M-H) 689.0524 (calculated for $C_{20}H_{23}N_{10}O_{10}P_2S_2^-$: 689.0521). $^1$H NMR (D$_2$O) 35° C. δ (ppm) 8.50 (s, 2H), δ8.37 (s, 2H), δ8.20 (s, 2H), δ8.10 (s, 2H), δ6.17 (s, 2H), δ6.14 (s, 2H), δ5.06-5.07 (m, 2H), δ4.96-5.02 (m, 2H), δ4.87-4.93 (m, 2H), δ4.75 (m, 2H), δ4.34-4.56 (m, 10H), δ3.98-4.13 (m, 2H), δ3.20 (q, J=7 Hz), δ1.27 (1, J=7 Hz). $^{31}$P NMR (D2O) 25° C. δ (ppm) 54.54, 54.84, 55.92 (minor).

Example 4. Synthesis of (11a), (11b) and (11c)

11a, 11b and 11c were synthesized as described in Gaffney et al. with the addition of prep HPLC purification of the final product (exemplified below) instead of a recrystallization, in order to achieve purities of ≥97% for biological testing. Alternatively, the prep HPLC purification can be carried out after the cyclization and deprotection steps as described for the adenosine series in FIG. 6, Examples 2 and 3.

11a

A 100 mg portion of 11a in 3 ml 10 mM triethylammonium acetate was applied to the prep HPLC column and eluted using a gradient of acetonitrile and 10 mM triethylammonium acetate in water (0% to 10% CH3CN gradient over 22 minutes at 50 ml/min flow). HPLC fractions containing pure 11a were pooled and the CH3CN was removed via rotoevaporation and the remaining aqueous sample lyophilized to dryness to give 40 mg of pure 11a as the bis-triethylammonium salt. HRMS of 11a in negative mode as m/z (M-H) 689.0893 (calculated for $C_{20}H_{23}N_{10}O_{14}P_2^-$: 689.0876). $^1$H NMR ($D_2O$) 45° C. δ (ppm) 8.05 (s, 2H), 5.98 (s, 2H), 4.90 (m, 2H), 4.76 (m, 2H), 4.41 (m, 2H), 4.33 (m, 2H), 4.09 (m, 2H), 3.19 (q, J=7 Hz, 6H), 1.28 (t, J=7 Hz, 9H). 31P NMR (D2O) 25° C. δ (ppm) −1.24.

11b

A 100 mg portion of the enriched 11b in 3 ml 6% CH3CN in 10 mM triethylammonium acetate was applied to the prep HPLC column and eluted using a gradient of acetonitrile and 10 mM triethylammonium acetate in water (6% to 18% CH3CN gradient over 22 minutes at 50 ml/min flow). HPLC fractions containing the pure 11b were pooled and the CH3CN was removed via rotoevaporation and the remaining aqueous sample lyophilized to dryness to give 40 mg (40% yields) of pure 11b as the bis-triethylammonium salt. HRMS of 11b in negative mode confirmed m/z (M-H) 721.0446 (calculated for $C_{20}H_{23}N_{10}O_{12}P_2S_2^-$:721.0419). $^1$H NMR ($D_2O$) 45° C. δ 8.05 (s, 2H), 5.98 (s, 2H), 5.03 (m, 2H), 4.77 (m, 4H), 4.10 (m, 2H), 4.08 (m, 2H), 3.19 (q, j=7 Hz, 6H), 1.28 (t, J=7 Hz, 9H). $^{31}$P NMR (D2O) 25° C. δ 54.87.

11c 60 mg of the enriched 11c in 3 ml 6% CH3CN in 10 mM triethylammonium acetate was applied to the prep HPLC column and eluted with a gradient of acetonitrile and 10 mM triethylammonium acetate in water (6% to 18% CH3CN gradient over 22 minutes at 50 ml/min flow). HPLC fractions containing the pure 11c were pooled and the CH3CN was removed via rotoevaporation and the remaining aqueous sample lyophilized to dryness to give 30 mg (50% yield) of pure 11c as the bis-triethylammonium salt. HRMS of 11c in negative mode confirmed m/z (M-2H) 360.0171 (calculated for $C_{20}H_{22}N_{10}O_{12}P_2S_2^{-2}$: 360.0173). $^1$H NMR ($D_2O$) 55° C. δ (ppm) 8.13 (s, 2H), 8.03 (s, 2H), 5.97 (m, 2H), 5.06-5.12 (br, 4H), 4.98-5.00 (m, 2H), 4.81-4.83 (m, 2H), 4.04-4.08 (m, 4H), 3.20 (q, j=7 Hz), 1.27 (t, J=7 Hz). 31P NMR (D2O) 25° C. δ (ppm) 54.77, 56.00.

Example 5. Interferon Induction by CDNs

To determine the relative level of IFN-β in antigen presenting cells induced by each of the Rp, Rp dithio c-di-GMP derivative molecules relative to the unmodified c-di-GMP molecules as a signature of adjuvant potency, $1 \times 10^5$ DC2.4 cells, a mouse-derived H-2b-restricted mouse dendritic cell line, were incubated with 5, 20, and 100 μM of c-di-GMP, Rp, Rp and Rp, or Sp dithio-diphosphate c-di-GMP, as well as c-di-AMP, Rp, Rp or Rp, Sp dithio-diphosphate c-di-AMP molecules or HBSS for 30 minutes at 37° C. with 5% CO2. After 30 minutes, cells were washed and replaced with RPMI media containing 10% FBS. To measure the level of induced IFN-β, cell culture fluids from each sample were collected after 4 hours, and 10 μL was added to $5 \times 10^4$ L929-ISRE luciferase reporter cells cultured in RPMI media+10% FBS. The relative level of IFN-β production was determined by measuring relative light units (RLU) after 4 hours of incubation.

Figure 7:
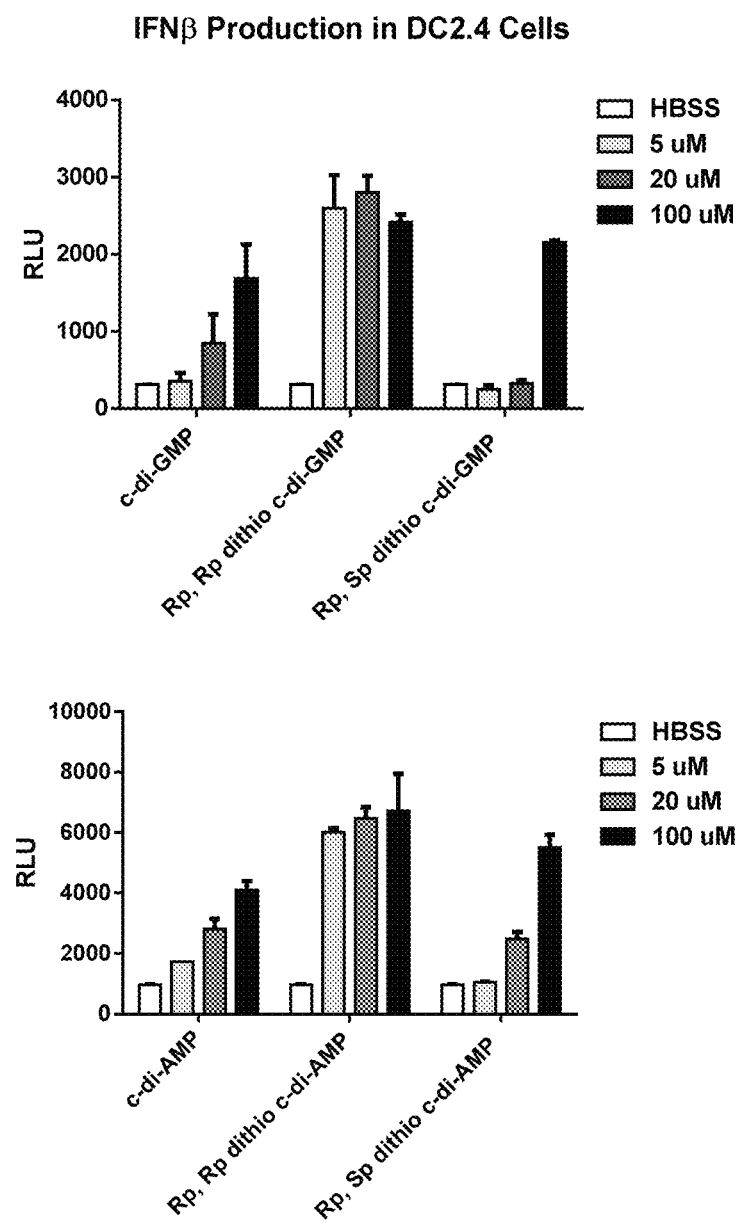
FIG. 7 depicts IFN-β induction in antigen presenting cells by parent CDNs and diatereomers of the corresponding dithio derivative molecules.

As shown in FIG. 7, the Rp, Rp dithio c-di-GMP and the Rp, Rp dithio c-di-AMP diastereomers induced significantly higher levels of IFN-β than either the c-di-GMP or c-di-AMP unmodified cyclic dinucleotide molecules. Further, the level of IFN-β induced by the Rp, Sp dithio c-di-GMP and the Rp, Sp dithio c-di-AMP diastereomers was lower than the level induced by both the Rp, Rp dithio c-di-GMP and the Rp, Rp dithio c-di-AMP diastereomers as well as the native c-di-GMP and c-di-AMP molecules. These results demonstrate that purified preparations of Rp, Rp dithio c-di-GMP and the Rp, Rp dithio c-di-AMP diastereomers more profoundly activate the innate immune response than the unmodified c-di-GMP and c-di-AMP molecules as well as the Rp, Sp dithio derivatives. The Rp, Sp thio derivatives of both c-di-GMP and c-di-AMP poorly activated the innate immune response. It will be apparent to the skilled artisan that preferred embodiments for adjuvants are Rp, Rp dithio-diphosphate c-di-GMP or Rp, Rp dithio-diphosphate c-di-AMP cyclic dinucleotides, due to their properties of increased activation of the innate immune response, as shown by magnitude of induced IFN-β expression, as compared to either Rp, Sp dithio-diphosphate c-di-GMP or Rp, Sp dithio-diphosphate c-di-AMP or c-di-GMP or c-di-AMP molecules.

Example 6. Degradation of CDNs by Phospohodiesterases

One mechanism for the increased potency of the Rp, Rp dithio-diphosphate c-di-GMP and c-di-AMP derivatives as compared to unmodified native c-di-GMP and c-di-AMP may be the resistance of the dithio-modified derivatives to degradation by host cell phosphodiesterases. As a test for this mechanism, Rp, Rp dithio c-di-GMP, unmodified c-di-GMP and also Rp, Rp dithio c-di-AMP and c-di-AMP molecules were incubated with and without 1 mg of snake venom phosphodiesterase (SVPD) overnight at 37° C. Following this incubation period, SVPD enzyme in the reactions was inactivated and removed by incubation at 100° C. for 10 minutes and the samples were then centrifuged at 14,000 rpm for 5 minutes. To test the relative capacity of the samples to activate innate immunity, measured by the level of IFN-β expression, $1 \times 10^5$ DC2.4 cells were incubated with 100 μM of Rp, Rp dithio-diphosphate c-di-GMP and c-di-AMP derivatives and unmodified native c-di-GMP and c-di-AMP processed from samples incubated with these cyclic dinucleotide preparations for 30 minutes at 37° C. with 5% CO2. After 30 minutes, the cells were washed and replaced with RPMI media containing 10% FBS and incubated for another 4 hrs. The culture fluids were then harvested, and 10 μL of these fluids were added to 5×104 L929-ISRE luciferase reporter cells grown in RPMI media containing 10% FBS. The relative level of IFN-β expression was determined by measuring relative light units (RLU) after 4 hours incubation in the reporter cell line.

Figure 8:
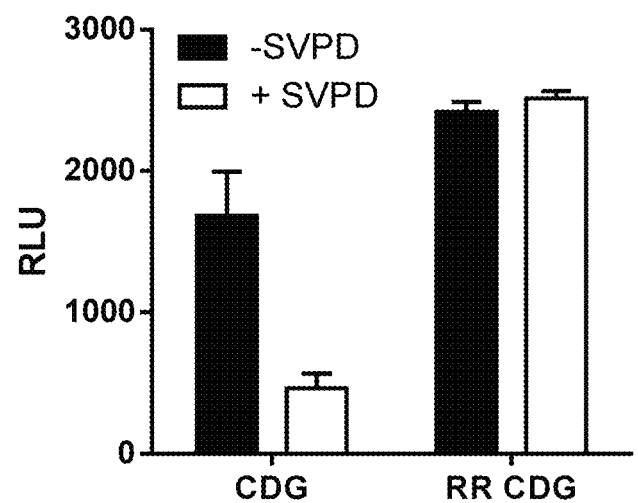
FIG. 8 depicts IFN-β induction in antigen presenting cells by CDN diatereomers following treatment with snake venom phosphodiesterase
Figure 8:
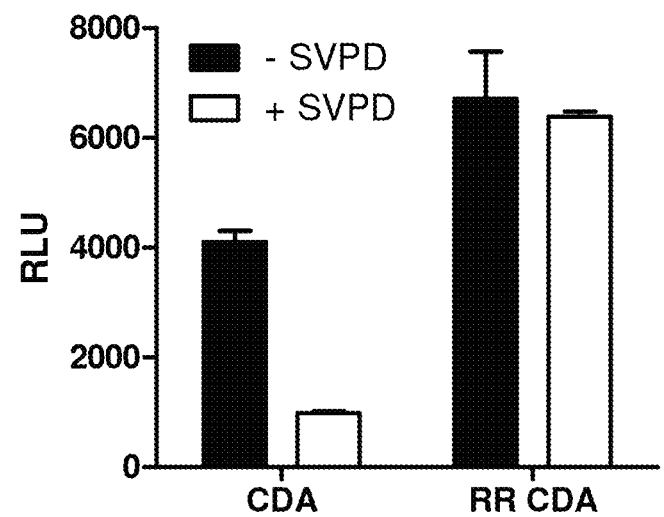

As shown in FIG. 8, the level of IFN-β expression in cells containing Rp, Rp dithio-diphosphate c-di-GMP ("RR-CDG") or Rp, Rp dithio-diphosphate c-di-AMP ("RR-CDA") was equivalent, regardless of whether the cyclic dinucleotides were incubated with SVPD. In contrast, the level of IFN-β expression was significantly lower in cultures containing c-di-GMP ("CDG") or c-di-AMP ("CDA") that had been previously incubated with SVPD, as compared to cultures containing c-di-GMP or c-di-AMP that had not been incubated with this enzyme. Furthermore, in cultures containing cyclic dinucleotides not incubated with SVPD, the level of IFN-β expression was greater with Rp, Rp dithio-diphosphate c-di-GMP or Rp, Rp dithio-diphosphate c-di-AMP as compared to c-di-GMP or c-di-AMP. These data are further supportive of the increased potency of Rp, Rp dithio-diphosphate c-di-GMP or Rp, Rp dithio-diphosphate c-di-AMP as compared to c-di-GMP or c-di-AMP.

Example 7. Immune Response Induction by CDNs

To test the enhanced in vivo immunogenicity of Rp, Rp dithio c-di-GMP relative to unmodified c-di-GMP molecules, OVA-specific CD4+ and CD8+ T cell responses were measured in PBMCs at 10 days post vaccination in conjunction with CDN treatment. Vaccines were prepared by combining 10 µg of OVA protein (EndoFit OVA, InVivogen) and Addavax (2% squalene final) with either 25 µg or 5 µg of cyclic dinucleotide, in a total volume of 100 µL. Groups of five female C57BL/6 mice (H-2b) were immunized once subcutaneously (s.c) in the base of the tail with the vaccine preparations, and the OVA-specific CD4+ and CD8+ T cell responses in the peripheral blood mononuclear cell (PBMC) compartment were determined by ELISpot analysis 10 days later. $1 \times 10^5$ PBMCs and $1 \times 10^5$ splenocyte feeder cells isolated from aged-matched naïve C57BL/6 mice were un-stimulated or stimulated with 1 µM of MHC class II peptide (OVA265-280 TEWTSSNVMEERKIKV) or MHC class I (OVA257-264 SIINFEKL) peptide overnight and IFN-γ spot forming cells were measured, as described previously.

Figure 9:
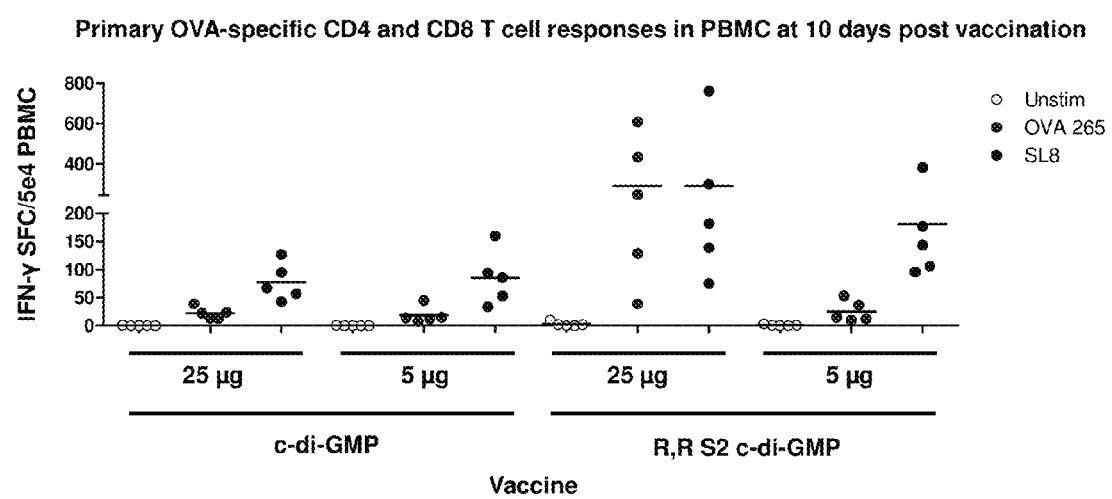
FIG. 9 depicts OVA-specific CD4 and CD8 T cell responses measured in PBMC at 10 days post vaccination in conjunction with CDN treatment.

As shown in FIG. 9, the CD4+ and CD8+ OVA-specific T cell responses were of greater magnitude in mice immunized with vaccines containing Rp, Rp dithio c-di-GMP as compared to unmodified c-di-GMP, in formulations containing the same amount of cyclic dinucleotide adjuvant. Furthermore, the magnitude of antigen-specific CD8+ T cell responses were greater in mice immunized with vaccine formulations containing 5 µg of Rp, Rp dithio c-di-GMP, as compared to mice immunized with vaccine formulations containing either 5 µg or 25 µg of unmodified c-di-GMP.

Example 8. T-Cell Response Induction by CDNs

To further assess the immunogenicity of Rp, Rp dithio c-di-GMP relative to unmodified c-di-GMP molecules, SIV gag-specific CD8+ and CD4+ T cell responses were measured. Five C57BL/6 mice per group were immunized subcutaneously twice with either 1 ug Rp, Rp dithio c-di-GMP or saline control formulated in 2% squalene-in-water with 10 ug SIV gag protein. Vaccinations were separated by 20 days, and spleens were harvested six days after the second vaccination. Immune responses were measured to SIV gag-specific CD8 (AL11, SIV $gag_{312-322}$, A) and CD4 (DD13, SIV $gag_{300-312}$, B) T cell epitopes by IFNγ ELISpot assay. Plates were scanned and spot forming cells (SFC) per well were enumerated using an ImmunoSpot analyzer (CTL).

Figure 10:
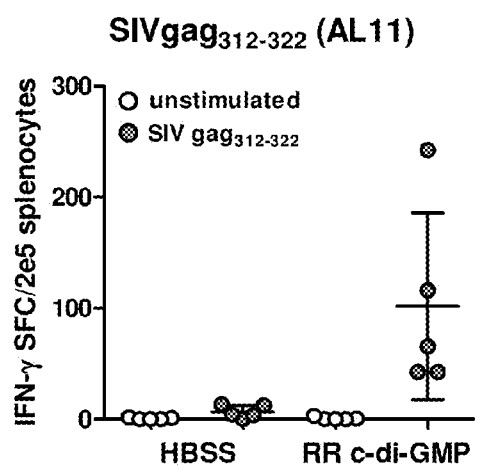
FIG. 10 depicts SIVgag-specific CD4 and CD8 T cell responses measured in PBMC post vaccination in conjunction with CDN treatment.
Figure 10:
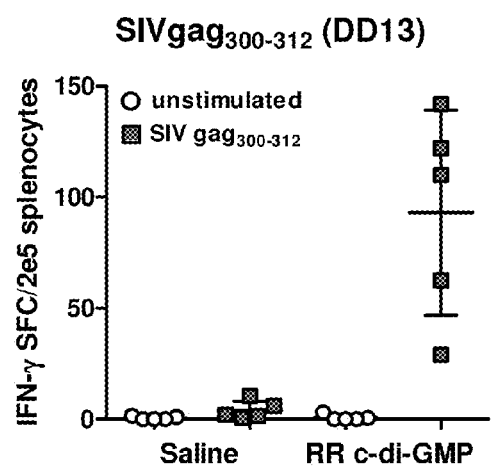

As shown in FIG. 10, animals immunized with RR c-di-GMP induced significantly higher SIV gag-specific CD8 and CD4 T cell responses compared to the animals that received the saline control. These results demonstrate that the vaccine formulations with the RR c-di-GMP derivative can induce SIV gag-specific CD4 and CD8 T cell responses in vivo. The skilled artisan will recognized that vaccine formulations containing Rp, Rp dithiophosphate c-di-GMP or Rp, Rp dithiophosphate c-di-AMP are preferred, since such cylic dinucleotides have increased potency as shown by higher magnitude of vaccine-induced immune responses, and also higher magnitude of vaccine-induced immune responses with comparatively lower dose levels of adjuvant.

Example 9. Induction of Protective Immunity by CDNs

To establish the enhanced immunogenicity and accompanying protective immunity induced by Rp, Rp dithio c-di-GMP relative to unmodified c-di-GMP, OVA-specific CD8 T cell responses measured in PBMC and protective immunity assessed against lethal bacterial challenge. Vaccines were prepared by combining 10 µg of OVA protein (EndoFit OVA, InVivogen) and Addavax (2% squalene final) with 25 µg of cyclic dinucleotide, in a total volume of 100 µL. Groups of five female C57BL/6 mice (H-$2^b$) were immunized twice subcutaneously (s.c) in the base of the tail with the vaccine preparations. The interval between the prime and boost immunizations was 36 days. The magnitude of both the memory and expansion phases of the $OVA_{257}$-specific CD8 T cell responses in PBMC were quantified by intracellular cytokine staining (ICS) analysis at both 27 days post-boost vaccination and at 3 days post challenge with a 2× lethal dose $(LD)_{50}$ dose ($1 \times 10^5$ colony forming units; CFU) of OVA-expressing wild-type *Listeria monocytogenes* (WT Lm-OVA). For ICS analysis, $1 \times 10^5$ PBMCs from test mice combined with $1 \times 10^5$ splenocyte feeder cells isolated from aged-matched naïve C57BL/6 mice were un-stimulated or stimulated with 1 µM of MHC class I peptide ($OVA_{257-264}$ SIINFEKL) for 5 hrs. in the presence of Brefeldin A, and IFN-γ production was measured by flow cytometry on a BD FACSVerse.

As shown in FIG. 11A, mice immunized with vaccines adjuvanted with Rp, Rp dithio-diphosphate c-di-GMP generated a higher magnitude of OVA-specific CD8 T cell memory, as compared to mice immunized with vaccines adjuvanted with unmodified c-di-GMP. The OVA-specific memory CD8 T cells induced by immunization with Rp, Rp dithio-diphosphate c-di-GMP adjuvanted vaccines expanded to a higher magnitude following challenge with pathogen expressing the cognate OVA antigen, as compared to the level of expansion of OVA-specific memory CD8 T cells in mice immunized with vaccines adjuvanted with unmodified c-di-GMP. The FACS plot shown in FIG. 11B demonstrates that the magnitude of OVA-specific CD8 T cell memory approached 30% of the total CD8 T cell population in PBMC from mice immunized with Rp, Rp dithio-diphosphate c-di-GMP adjuvanted vaccines. The gold standard for effective immunization is to test whether a vaccine candidate can confer protection against subsequent challenge with a virulent pathogen. To test the relative effectiveness of Rp, Rp dithio c-di-GMP and unmodified c-di-GMP adjuvanted vaccines, mice were challenged with an intravenous injection of a $2 \times LD_{50}$ dose ($1 \times 10^5$ CFU) of OVA-expressing wild-type *Listeria monocytogenes* (WT Lm-OVA) at 27 days post boost immunization. Three days later, protective immunity was determined by plating dilutions of homogenates of spleens harvested from test mice at 3 days post WT Lm-OVA challenge on brain-heart infusion agar media, and quantifying the number of colonies following overnight incubation at 37° C. FIG. 11C shows that immunization of mice with Rp, Rp dithio-diphosphate c-di-GMP adjuvanted vaccines afforded complete protection (below the limit of detection, LOD) against virulent pathogen challenge. It will be apparent to the skilled artisan that preferred embodiments for adjuvants are Rp, Rp dithio-diphosphate c-di-GMP or Rp, Rp dithio-diphosphate c-di-AMP cyclic dinucleotides, due to their properties of conferring profound vaccine potency, as shown by induction of high magnitude CD8 T cell memory pool which expands upon challenge with the cognate antigen and provides complete protection against virulent pathogen challenge.

Example 10. Induction of Effective Anti-Tumor Immunity by CDNs

The relative in vivo anti-tumor efficacy of the Rp, Rp dithio c-di-AMP and unmodified c-di-AMP derivatives were evaluated in a subcutaneous mouse model of prostate cancer. The derivative molecules were formulated with $1 \times 10^6$ irradiated whole TRAMP-C2 murine prostate tumor cells expressing GM-CSF (GVAX). Groups of 5 male C57BL/6 mice were implanted with $1 \times 10^5$ TRAMP-C2 tumor cells subcutaneous in the footpad. On days 4 and 11 post tumor implantation, mice were administered vaccinations subcutaneous in the flank of either GVAX alone, or GVAX formulated with RR-CDA or CDA, and compared to HBSS control. Tumor growth was monitored by calipers, and tumor volume was calculated.

As shown in FIG. 12, by day 52 post tumor implantation, the mice vaccinated with GVAX+RR-CDA demonstrated significant tumor growth inhibition as compared to HBSS control, with increased anti-tumor efficacy as compared to GVAX alone or GVAX formulated with the unmodified c-di-AMP derivative. These date demonstrate the increased anti-tumor potency of the Rp, Rp dithio c-di-AMP derivative molecule as compared to the unmodified c-di-AMP molecule in a murine prostate cancer model.

Example 11. Prodrug Forms of CDNs

Figure 13:
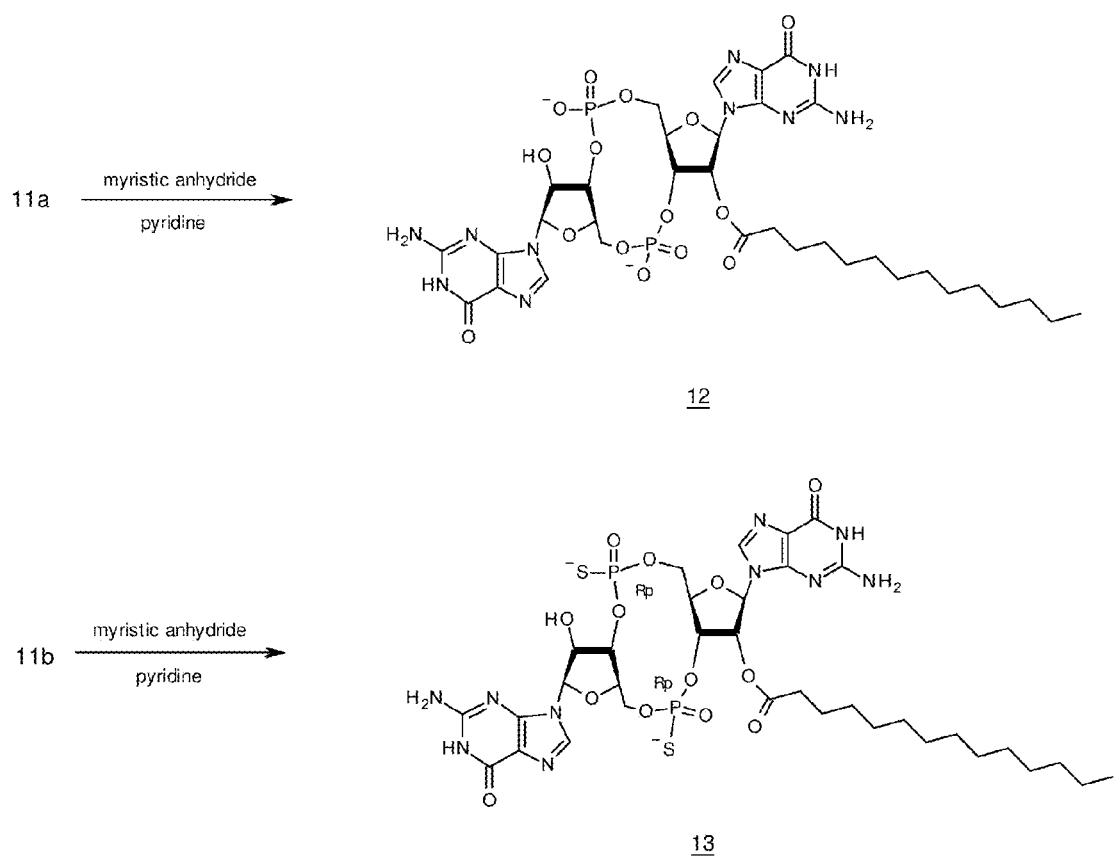
FIG. 13 depicts 2'-O-substituent prodrug analogs of CDNs of the present invention.

Prodrug strategies provide an attractive method for facilitating partitioning into the bilayer of cells or delivery liposomes. Acylation of the ribose 2'-OH of c-di-GMP, c-di-AMP and dithio-analogs with C-12 to C-18 carboxylic acids could serve as a valuable prodrug. Two examples are shown in FIG. 13 and described in the example.

(a) Synthesis of Mono-2'-O-Myristoyl c-Di-GMP 12 from 11a.

To the bistriethylamine salt of 11a (8 mg, 9.0 micromoles) was added 0.3 ml DMF, 30 microliters of pyridine and 15 mg of myristic anhydride (34 micromoles). The reaction mixture was stirred at room temp for 48 h and then heated at 60° C. for 0.5 h. The mass of major product 12 was confirmed by LC/MS in negative mode, with m/z (M-1) 889 (calcd for $C_{34}H_{49}N_{10}O_{15}P_2$-: 899.3). After evaporation the residue was taken in up in 30% CH3CN in 10 mM TEAA, filtered, and purified on a 20 mm prep C-18 HPLC column with gradient elution (30 to 60% CH3CN in 10 mM TEAA over 20 min at a flow of 20 ml/min). The fractions containing desired product were combined, rotoevaporated and lyophilized to give 3 mg of mono-2'-O-myristoyl c-di-GMP (M. HRMS of 12 in negative mode confirms m/z (M-2) 449.1389 (calculated for $C_{34}H_{48}N_{10}O_{15}P_2^{-2}$: 449.1393). $^1$H NMR (DMSO+1% D2O) 25° C. δ (ppm) 7.98 (s, 2H), 5.98 (s, 1H), 5.73 (d, 1H), 5.66 (s, 1H), 4.74 (d, 2H), 4.54 (s, 1H), 4.23 (s, 1H), 3.81-3.99 (br, 4H), 2.55 (s, 2H), 1.44 (s, 2H), 0.85 (t, 3H). (NMR peaks at 10.61, 7.33 and 6.55 in neat DMSO were exchanged on addition of 1% D$_2$O). Methylenes of the myristoyl group were obscured by DMSO and upfield triethylammonium acetate peaks. The NMR is consistent with monoacylation at 2'-OH. $^{31}$P NMR (D$_2$O) 25° C. δ (ppm) −1.37, −2.06.

(b) Synthesis of Mono-2'-O-Myristoyl [Rp,Rp] Dithiophosphate c-Di-GMP (13) from 11b.

To the bistriethylamine salt of 11b (12 mg, 13.0 micromoles) was added 0.3 ml DMF, 30 microliters of pyridine, 15 mg of myristic anhydride (34 micromoles) and catalytic DMAP. The reaction mixture was stirred at room temp for 24 h and then heated at 60° C. for 2 h. The solvent was removed by rotoevaporation and the residue taken up in 50% MeOH in 10 mM TEAA, filtered, and purified on a 20 mm prep C-18 HPLC column (50% MeOH in 10 mM TEAA isocratic for 5 min followed by gradient to 100% MeOH for 10 min and then 100% MeOH for 10 min). The desired product eluted late in this methanolic system. The fractions containing desired product were combined, rotoevaporated, and then lyophilized to give 4 mg of mono-2'-O-myristoyl [Rp,Rp] dithiophosphate c-di-GMP (13). HRMS of 13 in negative mode confirms m/z (M-2) 465.1148 (calculated for $C_{34}H_{48}N_{10}O_{13}P_2S_2^{-2}$: 465.1165). $^1$H NMR (DMSO+1% D$_2$O) 25° C. δ (ppm) 8.01 (s, 2H), 5.97 (d, 1H), 5.73 (d, 2H), 5.71 (m, 2H), 5.00 (m, 1H), 4.85 (m, 1H), 4.56 (m, 1H), 4.10-4.18 (m, 4H), 3.97 (m, 2H), 3.84-3.87 (m, 1H), 3.16 (s, 1H), 3.05 (d, 2H), 1.47 (br, 2H), 0.85 (t, 3H). (NMR peaks at 10.60, 7.53, 6.90 and 6.63 in neat DMSO were exchanged on addition of 1% D$_2$O). Methylenes of the myristoyl group were obscured by DMSO and upfield triethylammonium acetate peaks. The NMR is consistent with monoacylation at 2'-OH. $^{31}$P NMR (CD$_3$OD) 25° C. δ (ppm) 56.66, 55.46.

Figure 14:
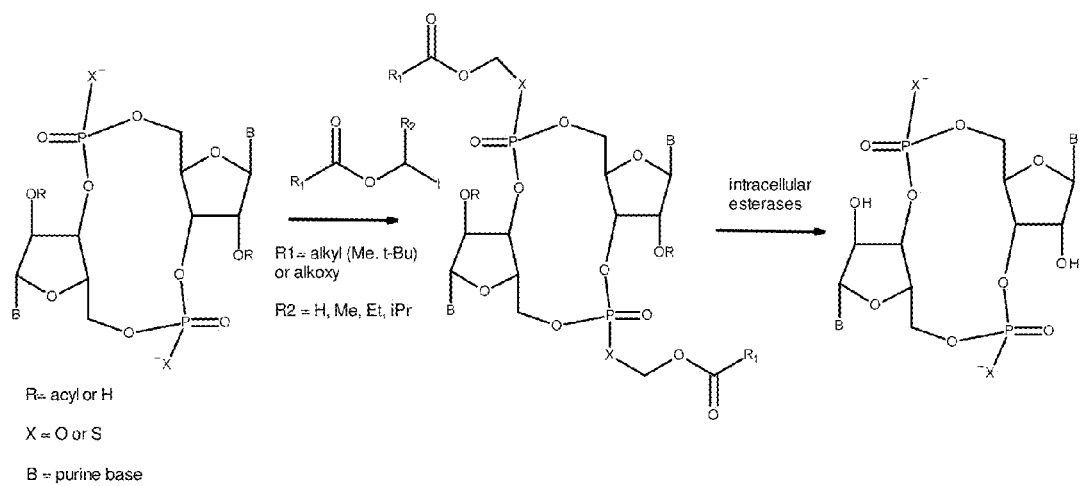
FIG. 14 depicts synthesis of O- or S-substituent prodrug analog of CDNs of the present invention.

A similar prodrug approach using acyloxyalkyl derivatization of sulfur or oxygen on CDN thiophosphates and phosphates, respectively, may also be used. The acyloxyalkyl structures in FIG. 14 are similar to Adefovir, an effective nucleoside analog pro-drug that is used to treat HIV and HBV infection. Once inside the cell intracellular esterases will cleave the acyl or acyloxyalky groups present on 2'-OH or phosphate (thiophosphate) and regenerate the underivatized cyclic dinucleotide.

Example 12. Pharmacological Activity of CDN Prodrugs

To determine the relative potency of the prodrug form of c-di-GMP to activate the innate immune response, relative levels of IFN-β induced in a human monocyte cell line were assessed. For these experiments, 4×105 THP1-Blue human monocytes were transfected with an IRF-inducible secreted embryonic alkaline phosphatase reporter gene (Invivogen), and incubated with 100 μM of c-di-GMP, mono-2'-O-myristoyl c-di-GMP or HBSS for 30 minutes at 37° C. with 5% CO2. After 30 minutes, cells were washed and plated in 96-well dish in RPMI media containing 10% FBS, and incubated at 37° C. with 5% CO2. Cell culture supernatants from each sample were collected after 4 hours. 10 μL of the cell culture supernatants was added to QUANTI-Blue reagent (Invivogen) and incubated for 15-30 minutes. Absorbance at 655 nm was measured using a Model 680 spectrophotometer (BioRad).

Figure 15:
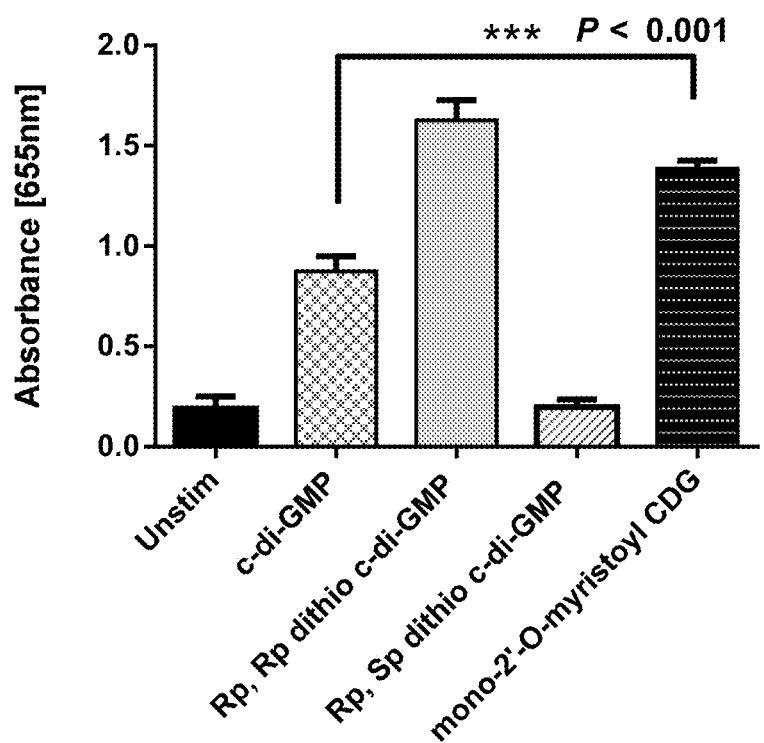
FIG. 15 depicts IFN-β induction in a human monocytic cell line following administration of a mono-2'-O-myristoyl c-di-GMP prodrug form of c-di-GMP.

As shown in FIG. 15, the mono-2'-O-myristoyl c-di-GMP ("mono-2'-O-myristoyl CDG") derivative induced significantly higher levels of IFN-β over the c-di-GMP unmodified cyclic dinucleotide molecule, and over background (HBSS) levels in a human monocyte cell line. Additionally, these data demonstrate in a human monocyte cell line, the superior induction of the Rp, Rp dithio c-di-GMP derivative molecules over the Rp, Sp dithio c-di-GMP and c-di-GMP unmodified molecules. These results demonstrate that purified preparations of mono-2'-O-myristoyl c-di-GMP derivatives can activate the innate immune response in a human cell line.

Example 13. Induction of Immune Responses by CDN Prodrugs

To assess the ability of the mono-2'-O-myristoyl c-di-GMP ("mono-2'-O-myristoyl CDG") derivative to induce in vivo immune responses, OVA-specific CD8 T cell responses were measured in splenocytes at 7 days post second vaccination in conjunction with CDN treatment. To test the ability of mono-2'-O-myristoyl c-di-GMP relative to stimulate an OVA-specific immune responses, vaccines were prepared by combining 10 μg of OVA protein (EndoFit OVA, Invivogen) and Addavax (2% squalene final) with either 0 (Control) or 5 μg of mono-2'-O-myristoyl c-di-GMP derivative ("mono-2'-O-myristoyl CDG"), in a total volume of 100 μL. Groups of five female C57BL/6 mice (H-2b) were immunized twice subcutaneously (s.c) in the base of the tail with the vaccine preparations, and the OVA-specific CD8+ T cell responses in the spleens were determined by intracellular cytokine staining 7 days later. 1×106 splenocytes were unstimulated or stimulated with 1 μM of MHC class I (OVA257-264 SIINFEKL; SL8) peptide overnight and IFN-γ production was measured by flow cytometer on a BD FACSVerse.

Figure 16:
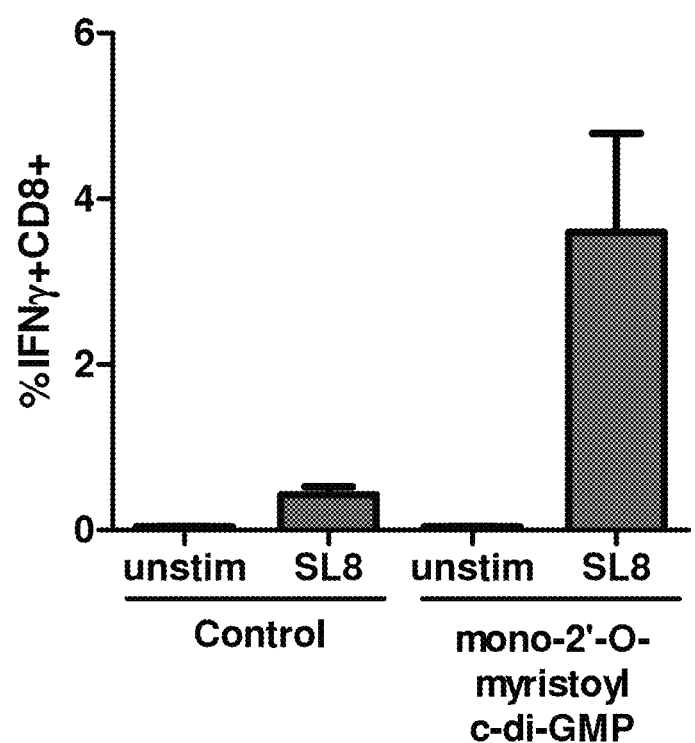
FIG. 16 depicts OVA-specific CD8 T cell responses following vaccination with a mono-2'-O-myristoyl c-di-GMP prodrug form of c-di-GMP.

As shown in FIG. 16, vaccines that contained the mono-2'-O-myristoyl c-di-GMP derivative induced greater immune responses compared to Control vaccines. These results demonstrate that a vaccine containing the mono-2'-O-myristoyl c-di-GMP derivative can stimulate highly potent adaptive immune responses in an animal model.

One skilled in the art readily appreciates that the present invention is well adapted to carry out the objects and obtain the ends and advantages mentioned, as well as those inherent therein. The examples provided herein are representative of preferred embodiments, are exemplary, and are not intended as limitations on the scope of the invention.

It is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

While the invention has been described and exemplified in sufficient detail for those skilled in this art to make and use it, various alternatives, modifications, and improvements should be apparent without departing from the spirit and scope of the invention. The examples provided herein are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

Other embodiments are set forth within the following claims.

We claim:

1. A method of inducing an immune response to a cancer in an individual, or inducing an immune response to a pathogen in an individual, comprising:
   parenterally administering to the individual in need thereof a composition comprising one or more cyclic purine dinucleotides or pharmaceutically acceptable salts thereof which induce STING-dependent TBK1 activation, wherein the cyclic purine dinucloetides present in the composition are thiophosphate cyclic purine dinucloetides that are substantially pure Rp,Rp diastereomers, or pharmaceutically acceptable salts thereof, wherein the 2'-OH substituent of either or both ribose moieties of the one or more cyclic purine dinucleotides is replaced with a substituent selected from the group consisting of fluorine, chlorine, bromine and iodine.

2. The method according to claim 1, wherein the composition comprises an inactivated tumor cell or a mixture of different tumor cells type-matched to the individual's cancer.

3. The method according to claim 2, wherein the tumor cell is selected from the group consisting of a colorectal cancer cell, an aero-digestive squamous cancer cell, a lung cancer cell, a brain cancer cell, a liver cancer cell, a stomach cancer cell, a sarcoma cell, a leukemia cell, a lymphoma cell, a multiple myeloma cell, an ovarian cancer cell, a uterine cancer cell, a breast cancer cell, a melanoma cell, a prostate cancer cell, a pancreatic carcinoma cell, and a renal carcinoma cell.

4. The method according to claim 1, wherein the thiophosphate cyclic purine dinucleotide is formulated with one or more lipids.

5. The method according to claim 4, wherein the one or more lipids comprise digitonin.

6. The method according to claim 4, wherein the one or more lipids form a liposome.

7. The method according to claim 1, wherein the thiophosphate cyclic purine dinucleotide is formulated with one or more adjuvants.

8. The method according to claim 7, wherein the one or more adjuvants comprise CpG and/or monophosphoryl lipid A.

9. The method according to claim 1, further comprising administering one or more vaccines to the individual, wherein the vaccine(s) comprises one or more antigens selected to stimulate an immune response to a pathogen expressing one or more of the antigens.

10. The method according to claim 9, wherein the vaccine(s) comprise inactivated or attenuated bacteria or viruses comprising the antigen of interest, purified antigens, live viral or bacterial delivery vectors recombinantly engineered to express and/or secrete the antigens, antigen presenting cell (APC) vectors comprising cells that are loaded with the antigens or transfected with a composition comprising a nucleic acid encoding the antigens, liposomal delivery vehicles comprising the antigens, or naked nucleic acid vectors encoding the antigens.

11. The method according to claim 1, wherein the one or more thiophosphate cyclic purine dinucleotides is formulated as a nanoparticle.

* * * * *